US008287820B2

(12) United States Patent
Williams et al.

(10) Patent No.: US 8,287,820 B2
(45) Date of Patent: Oct. 16, 2012

(54) AUTOMATED PIPETTING APPARATUS HAVING A COMBINED LIQUID PUMP AND PIPETTE HEAD SYSTEM

(75) Inventors: Jeff Williams, Chelsea, MI (US); Kerry Wilson, Elkhart, IN (US)

(73) Assignee: HandyLab, Inc., Franklin Lakes, NJ (US)

( * ) Notice: Subject to any disclaimer, the term of this patent is extended or adjusted under 35 U.S.C. 154(b) by 517 days.

(21) Appl. No.: 12/212,403

(22) Filed: Sep. 17, 2008

(65) Prior Publication Data

US 2009/0155123 A1    Jun. 18, 2009

Related U.S. Application Data

(63) Continuation-in-part of application No. 12/173,023, filed on Jul. 14, 2008, and a continuation-in-part of application No. 12/218,498, filed on Jul. 14, 2008.

(60) Provisional application No. 60/959,437, filed on Jul. 13, 2007, provisional application No. 60/959,437, filed on Jul. 13, 2007.

(51) Int. Cl.
*B01L 3/02* (2006.01)

(52) U.S. Cl. ....... 422/509; 422/500; 422/501; 422/68.1; 422/50; 422/81; 222/52; 222/55; 222/56; 222/71; 222/204

(58) Field of Classification Search ............... 222/52, 222/55, 56, 71, 204; 137/150–159; 422/50, 422/67, 68.1, 81, 500, 501, 509, 521, 522, 422/53; 436/6.1, 6.12, 287.2

See application file for complete search history.

(56) References Cited

U.S. PATENT DOCUMENTS

| | | | |
|---|---|---|---|
| 1,434,314 | A | 10/1922 | Raich |
| 1,616,419 | A | 2/1927 | Wilson |
| 1,733,401 | A | 8/1930 | Lovekin |
| 3,528,449 | A | 9/1970 | Witte et al. |
| 3,985,649 | A | 10/1976 | Eddelman |
| 4,018,089 | A | 4/1977 | Dzula et al. |

(Continued)

FOREIGN PATENT DOCUMENTS

CA    2294819    1/1999

(Continued)

OTHER PUBLICATIONS

Brahmasandra et al., On-chip DNA detection in microfabricated separation systems, SPIE Conference on Microfuidic Devices and Systems, 1998, vol. 3515, pp. 242-251, Santa Clara, CA.

(Continued)

*Primary Examiner* — In Suk Bullock
*Assistant Examiner* — Sharon Pregler
(74) *Attorney, Agent, or Firm* — Knobbe Martens Olson & Bear LLP

(57) ABSTRACT

The technology described herein generally relates to systems for extracting polynucleotides from multiple samples, particularly from biological samples, and additionally to systems that subsequently amplify and detect the extracted polynucleotides. The technology more particularly relates to microfluidic systems that carry out PCR on multiple samples of nucleotides of interest within microfluidic channels, and detect those nucleotides. The technology still more particularly relates to automated devices for carrying out pipetting operations, particularly on samples in parallel, consistent with sample preparation and delivery of PCR-ready nucleotide extracts to a cartridge wherein PCR is run.

20 Claims, 26 Drawing Sheets

U.S. PATENT DOCUMENTS

| | | | |
|---|---|---|---|
| 4,018,652 A | 4/1977 | Lanham et al. | |
| 4,038,192 A | 7/1977 | Serur | |
| 4,055,395 A | 10/1977 | Honkawa et al. | |
| D249,706 S | 9/1978 | Adamski | |
| 4,139,005 A | 2/1979 | Dickey | |
| D252,157 S | 6/1979 | Kronish et al. | |
| D252,341 S | 7/1979 | Thomas | |
| D254,687 S | 4/1980 | Fadler et al. | |
| 4,212,744 A | 7/1980 | Oota | |
| D261,033 S | 9/1981 | Armbruster | |
| D261,173 S | 10/1981 | Armbruster | |
| 4,301,412 A | 11/1981 | Hill et al. | |
| 4,439,526 A | 3/1984 | Columbus | |
| 4,457,329 A | 7/1984 | Werley et al. | |
| 4,466,740 A | 8/1984 | Kano et al. | |
| 4,504,582 A | 3/1985 | Swann | |
| 4,522,786 A | 6/1985 | Ebersole | |
| D279,817 S | 7/1985 | Chen et al. | |
| 4,599,315 A | 7/1986 | Teraski et al. | |
| 4,612,873 A | 9/1986 | Eberle | |
| 4,612,959 A | 9/1986 | Costello | |
| D288,478 S | 2/1987 | Carlson et al. | |
| 4,654,127 A | 3/1987 | Baker et al. | |
| 4,673,657 A | 6/1987 | Christian | |
| 4,683,195 A | 7/1987 | Mullis et al. | |
| 4,683,202 A | 7/1987 | Mullis | |
| D292,735 S | 11/1987 | Lovborg | |
| 4,720,374 A | 1/1988 | Ramachandran | |
| 4,798,693 A | 1/1989 | Mase et al. | |
| 4,800,022 A | 1/1989 | Leonard | |
| 4,841,786 A * | 6/1989 | Schulz | 73/864.25 |
| D302,294 S | 7/1989 | Hillman | |
| 4,871,779 A | 10/1989 | Killat et al. | |
| 4,895,650 A | 1/1990 | Wang | |
| 4,919,829 A | 4/1990 | Gates et al. | |
| 4,921,809 A | 5/1990 | Schiff et al. | |
| 4,935,342 A | 6/1990 | Seligson et al. | |
| 4,946,562 A | 8/1990 | Guruswamy | |
| 4,949,742 A | 8/1990 | Rando et al. | |
| D310,413 S | 9/1990 | Bigler et al. | |
| 4,963,498 A | 10/1990 | Hillman | |
| 4,967,950 A | 11/1990 | Legg et al. | |
| 4,978,502 A | 12/1990 | Dole et al. | |
| 4,978,622 A | 12/1990 | Mishell et al. | |
| 4,989,626 A | 2/1991 | Takagi et al. | |
| 5,001,417 A | 3/1991 | Pumphrey et al. | |
| 5,004,583 A | 4/1991 | Guruswamy et al. | |
| 5,048,554 A | 9/1991 | Kremer | |
| 5,053,199 A | 10/1991 | Keiser et al. | |
| 5,060,823 A | 10/1991 | Perlman | |
| 5,061,336 A | 10/1991 | Soane | |
| 5,064,618 A | 11/1991 | Baker et al. | |
| 5,071,531 A | 12/1991 | Soane | |
| 5,091,328 A | 2/1992 | Miller | |
| D324,426 S | 3/1992 | Fan et al. | |
| 5,096,669 A | 3/1992 | Lauks et al. | |
| 5,126,002 A | 6/1992 | Iwata et al. | |
| 5,126,022 A | 6/1992 | Soane et al. | |
| D328,135 S | 7/1992 | Fan et al. | |
| D328,794 S | 8/1992 | Frenkel et al. | |
| 5,135,627 A | 8/1992 | Soane | |
| 5,135,872 A | 8/1992 | Pouletty et al. | |
| 5,147,606 A | 9/1992 | Charlton et al. | |
| 5,169,512 A | 12/1992 | Wiedenmann et al. | |
| D333,522 S | 2/1993 | Gianino | |
| 5,186,339 A | 2/1993 | Heissler | |
| 5,192,507 A | 3/1993 | Taylor et al. | |
| 5,208,163 A | 5/1993 | Charlton et al. | |
| 5,223,226 A | 6/1993 | Wittmer et al. | |
| D338,275 S | 8/1993 | Fischer et al. | |
| 5,250,263 A | 10/1993 | Manz | |
| 5,252,743 A | 10/1993 | Barrett et al. | |
| 5,256,376 A | 10/1993 | Callan et al. | |
| 5,275,787 A | 1/1994 | Yuguchi et al. | |
| 5,282,950 A | 2/1994 | Dietze et al. | |
| 5,296,375 A | 3/1994 | Kricka et al. | |
| 5,304,477 A | 4/1994 | Nagoh et al. | |
| 5,304,487 A | 4/1994 | Wilding et al. | |
| D347,478 S | 5/1994 | Pinkney | |
| 5,311,896 A | 5/1994 | Kaartinen | |
| 5,311,996 A | 5/1994 | Duffy et al. | |
| 5,316,727 A | 5/1994 | Suzuki et al. | |
| 5,327,038 A | 7/1994 | Culp | |
| 5,339,486 A | 8/1994 | Persic, Jr. | |
| D351,475 S | 10/1994 | Gerber | |
| D351,913 S | 10/1994 | Hieb et al. | |
| 5,364,591 A | 11/1994 | Green et al. | |
| 5,372,946 A | 12/1994 | Cusak et al. | |
| 5,374,395 A | 12/1994 | Robinson | |
| 5,389,339 A | 2/1995 | Petschek et al. | |
| 5,397,709 A | 3/1995 | Berndt | |
| 5,401,465 A | 3/1995 | Smethers et al. | |
| 5,411,708 A | 5/1995 | Moscetta et al. | |
| 5,414,245 A | 5/1995 | Hackleman | |
| 5,416,000 A | 5/1995 | Allen et al. | |
| 5,422,271 A | 6/1995 | Chen et al. | |
| 5,422,284 A | 6/1995 | Lau | |
| 5,427,946 A | 6/1995 | Kricka et al. | |
| 5,474,796 A | 12/1995 | Brennan | |
| D366,116 S | 1/1996 | Biskupski | |
| 5,486,335 A | 1/1996 | Wilding et al. | |
| 5,494,639 A | 2/1996 | Grzegorzewski | |
| 5,498,392 A | 3/1996 | Wilding et al. | |
| 5,503,803 A | 4/1996 | Brown | |
| 5,516,410 A | 5/1996 | Schneider et al. | |
| 5,519,635 A | 5/1996 | Miyake et al. | |
| 5,529,677 A | 6/1996 | Schneider et al. | |
| 5,559,432 A | 9/1996 | Logue | |
| 5,565,171 A | 10/1996 | Dovichi et al. | |
| 5,569,364 A | 10/1996 | Hooper et al. | |
| 5,578,818 A | 11/1996 | Kain et al. | |
| 5,579,928 A | 12/1996 | Anukwuem | |
| 5,580,523 A | 12/1996 | Bard | |
| 5,582,884 A | 12/1996 | Ball et al. | |
| 5,585,069 A | 12/1996 | Zanucchi et al. | |
| 5,585,089 A | 12/1996 | Queen et al. | |
| 5,585,242 A | 12/1996 | Bouma et al. | |
| 5,587,128 A | 12/1996 | Wilding et al. | |
| 5,589,136 A | 12/1996 | Northrup et al. | |
| 5,593,838 A | 1/1997 | Zanzucchi et al. | |
| 5,595,708 A | 1/1997 | Berndt | |
| 5,599,432 A | 2/1997 | Manz et al. | |
| 5,599,503 A | 2/1997 | Manz et al. | |
| 5,599,667 A | 2/1997 | Arnold, Jr. et al. | |
| 5,601,727 A | 2/1997 | Bormann et al. | |
| 5,603,351 A | 2/1997 | Cherukuri et al. | |
| 5,605,662 A | 2/1997 | Heller et al. | |
| D378,782 S | 4/1997 | LaBarbera et al. | |
| 5,628,890 A | 5/1997 | Carter et al. | |
| 5,630,920 A | 5/1997 | Friese et al. | |
| 5,631,337 A | 5/1997 | Sassi et al. | |
| 5,632,876 A | 5/1997 | Zanzucchi et al. | |
| 5,632,957 A | 5/1997 | Heller et al. | |
| 5,635,358 A | 6/1997 | Wilding et al. | |
| 5,637,469 A | 6/1997 | Wilding et al. | |
| 5,639,423 A | 6/1997 | Northrup et al. | |
| 5,643,738 A | 7/1997 | Zanzucchi et al. | |
| 5,646,039 A | 7/1997 | Northrup et al. | |
| 5,647,994 A | 7/1997 | Tuunanen et al. | |
| 5,651,839 A | 7/1997 | Rauf | |
| 5,652,149 A | 7/1997 | Mileaf et al. | |
| D382,346 S | 8/1997 | Buhler et al. | |
| D382,647 S | 8/1997 | Staples et al. | |
| 5,667,976 A | 9/1997 | Van Ness et al. | |
| 5,671,303 A | 9/1997 | Shieh et al. | |
| 5,674,394 A | 10/1997 | Whitmore | |
| 5,674,742 A | 10/1997 | Northrup et al. | |
| 5,681,484 A | 10/1997 | Zanzucchi et al. | |
| 5,681,529 A | 10/1997 | Taguchi et al. | |
| 5,683,657 A | 11/1997 | Mian | |
| 5,699,157 A | 12/1997 | Parce | |
| 5,700,637 A | 12/1997 | Southern | |
| 5,705,813 A | 1/1998 | Apffel et al. | |
| 5,726,026 A | 3/1998 | Wilding et al. | |
| 5,726,404 A | 3/1998 | Brody | |
| 5,726,944 A | 3/1998 | Taft et al. | |
| 5,731,212 A | 3/1998 | Gavin et al. | |

| | | | | | | |
|---|---|---|---|---|---|---|
| 5,744,366 A | 4/1998 | Kricka et al. | | 5,980,719 A | 11/1999 | Cherukuri et al. |
| 5,747,666 A | 5/1998 | Willis | | 5,981,735 A | 11/1999 | Thatcher et al. |
| 5,750,015 A | 5/1998 | Soane et al. | | 5,989,402 A | 11/1999 | Chow et al. |
| 5,755,942 A | 5/1998 | Zanzucchi et al. | | 5,992,820 A | 11/1999 | Fare et al. |
| 5,763,262 A | 6/1998 | Wong et al. | | 5,993,611 A | 11/1999 | Moroney, III et al. |
| 5,770,029 A | 6/1998 | Nelson et al. | | 5,993,750 A | 11/1999 | Ghosh et al. |
| 5,770,388 A | 6/1998 | Vorpahl | | 5,997,708 A | 12/1999 | Craig |
| 5,772,966 A | 6/1998 | Maracas et al. | | 6,001,229 A | 12/1999 | Ramsey |
| 5,779,868 A | 7/1998 | Parce et al. | | 6,001,231 A | 12/1999 | Kopf-Sill |
| 5,787,032 A | 7/1998 | Heller et al. | | 6,001,307 A | 12/1999 | Naka et al. |
| 5,788,814 A | 8/1998 | Sun et al. | | 6,004,515 A | 12/1999 | Parce et al. |
| 5,800,600 A | 9/1998 | Lima-Marques et al. | | 6,007,690 A | 12/1999 | Nelson et al. |
| 5,800,690 A | 9/1998 | Chow et al. | | 6,010,607 A | 1/2000 | Ramsey |
| 5,804,436 A | 9/1998 | Okun et al. | | 6,010,608 A | 1/2000 | Ramsey |
| D399,959 S | 10/1998 | Prokop et al. | | 6,010,627 A | 1/2000 | Hood, III |
| 5,827,481 A | 10/1998 | Bente et al. | | 6,012,902 A | 1/2000 | Parce |
| 5,842,106 A | 11/1998 | Thaler et al. | | D420,747 S | 2/2000 | Dumitrescu et al. |
| 5,842,787 A | 12/1998 | Kopf-Sill et al. | | D421,130 S | 2/2000 | Cohen et al. |
| 5,846,396 A | 12/1998 | Zanzucchi et al. | | 6,024,920 A | 2/2000 | Cunanan |
| 5,849,208 A | 12/1998 | Hayes et al. | | D421,653 S | 3/2000 | Purcell |
| 5,849,486 A | 12/1998 | Heller et al. | | 6,033,546 A | 3/2000 | Ramsey |
| 5,849,489 A | 12/1998 | Heller | | 6,043,080 A | 3/2000 | Lipshutz et al. |
| 5,849,598 A | 12/1998 | Wilson et al. | | 6,046,056 A | 4/2000 | Parce et al. |
| 5,852,495 A | 12/1998 | Parce | | 6,048,734 A | 4/2000 | Burns et al. |
| 5,856,174 A | 1/1999 | Lipshutz et al. | | 6,054,034 A | 4/2000 | Soane et al. |
| 5,858,187 A | 1/1999 | Ramsey et al. | | 6,054,277 A | 4/2000 | Furcht et al. |
| 5,858,188 A | 1/1999 | Soane et al. | | 6,056,860 A | 5/2000 | Amigo et al. |
| 5,863,502 A | 1/1999 | Southgate et al. | | 6,057,149 A | 5/2000 | Burns et al. |
| 5,863,708 A | 1/1999 | Zanzucchi et al. | | 6,062,261 A | 5/2000 | Jacobson et al. |
| 5,863,801 A | 1/1999 | Southgate et al. | | 6,063,341 A | 5/2000 | Fassbind et al. |
| 5,866,345 A | 2/1999 | Wilding et al. | | 6,063,589 A | 5/2000 | Kellogg et al. |
| 5,869,004 A | 2/1999 | Parce et al. | | 6,068,752 A | 5/2000 | Dubrow et al. |
| 5,869,244 A | 2/1999 | Martin et al. | | 6,071,478 A | 6/2000 | Chow |
| 5,872,010 A | 2/1999 | Karger et al. | | 6,074,725 A | 6/2000 | Kennedy |
| 5,872,623 A | 2/1999 | Stabile et al. | | 6,074,827 A | 6/2000 | Nelson et al. |
| 5,874,046 A | 2/1999 | Megerle | | D428,497 S | 7/2000 | Lapeus et al. |
| 5,876,675 A | 3/1999 | Kennedy | | 6,086,740 A | 7/2000 | Kennedy |
| 5,880,071 A | 3/1999 | Parce et al. | | 6,096,509 A | 8/2000 | Okun et al. |
| 5,882,465 A | 3/1999 | McReynolds | | 6,100,541 A | 8/2000 | Nagle et al. |
| 5,883,211 A | 3/1999 | Sassi et al. | | 6,102,897 A | 8/2000 | Lang |
| 5,885,432 A | 3/1999 | Hooper et al. | | 6,103,537 A | 8/2000 | Ullman et al. |
| 5,885,470 A | 3/1999 | Parce et al. | | 6,106,685 A | 8/2000 | McBride et al. |
| 5,895,762 A | 4/1999 | Greenfield et al. | | 6,110,343 A | 8/2000 | Ramsey et al. |
| 5,900,130 A | 5/1999 | Benregnu et al. | | 6,123,205 A | 9/2000 | Dumitrescu et al. |
| 5,912,124 A | 6/1999 | Kumar | | 6,123,798 A | 9/2000 | Gandhi et al. |
| 5,912,134 A | 6/1999 | Shartle | | 6,130,098 A | 10/2000 | Handique et al. |
| 5,916,522 A | 6/1999 | Boyd et al. | | 6,132,580 A | 10/2000 | Mathies et al. |
| 5,916,776 A | 6/1999 | Kumar | | 6,132,684 A | 10/2000 | Marino |
| 5,919,646 A | 7/1999 | Okun et al. | | 6,133,436 A | 10/2000 | Koster et al. |
| 5,919,711 A | 7/1999 | Boyd et al. | | D433,759 S | 11/2000 | Mathis et al. |
| 5,922,591 A | 7/1999 | Anderson et al. | | 6,143,250 A | 11/2000 | Tajima |
| 5,927,547 A | 7/1999 | Papen et al. | | 6,149,787 A | 11/2000 | Chow et al. |
| 5,928,880 A | 7/1999 | Wilding et al. | | 6,156,199 A | 12/2000 | Zuk, Jr. |
| 5,929,208 A | 7/1999 | Heller et al. | | 6,158,269 A * | 12/2000 | Dorenkott et al. ............ 422/562 |
| D413,391 S | 8/1999 | Lapeus et al. | | 6,167,910 B1 | 1/2001 | Chow |
| 5,932,799 A | 8/1999 | Moles | | 6,168,948 B1 | 1/2001 | Anderson et al. |
| 5,935,401 A | 8/1999 | Amigo | | 6,171,850 B1 | 1/2001 | Nagle et al. |
| 5,939,291 A | 8/1999 | Loewy et al. | | 6,174,675 B1 | 1/2001 | Chow et al. |
| 5,942,443 A | 8/1999 | Parce et al. | | D438,311 S | 2/2001 | Yamanishi et al. |
| D413,677 S | 9/1999 | Dumitrescu et al. | | 6,190,619 B1 | 2/2001 | Kilcoin et al. |
| 5,948,227 A | 9/1999 | Dubrow | | D438,632 S | 3/2001 | Miller |
| 5,955,028 A | 9/1999 | Chow | | D438,633 S | 3/2001 | Miller |
| 5,955,029 A | 9/1999 | Wilding et al. | | 6,197,595 B1 | 3/2001 | Anderson et al. |
| 5,957,579 A | 9/1999 | Kopf-Sill et al. | | 6,211,989 B1 | 4/2001 | Wulf et al. |
| 5,958,203 A | 9/1999 | Parce et al. | | 6,213,151 B1 | 4/2001 | Jacobson et al. |
| 5,958,694 A | 9/1999 | Nikiforov | | 6,221,600 B1 | 4/2001 | MacLeod et al. |
| 5,959,221 A | 9/1999 | Boyd et al. | | 6,228,635 B1 | 5/2001 | Armstrong et al. |
| 5,959,291 A | 9/1999 | Jensen | | 6,232,072 B1 | 5/2001 | Fisher |
| 5,964,995 A | 10/1999 | Nikiforov et al. | | 6,235,175 B1 | 5/2001 | Dubrow et al. |
| 5,964,997 A | 10/1999 | McBride | | 6,235,313 B1 | 5/2001 | Mathiowitz et al. |
| 5,965,001 A | 10/1999 | Chow et al. | | 6,235,471 B1 | 5/2001 | Knapp et al. |
| 5,965,410 A | 10/1999 | Chow et al. | | 6,236,581 B1 | 5/2001 | Lines et al. |
| 5,965,886 A | 10/1999 | Sauer et al. | | 6,251,343 B1 | 6/2001 | Dubrow et al. |
| 5,968,745 A | 10/1999 | Thorp et al. | | 6,254,826 B1 | 7/2001 | Acosta et al. |
| 5,972,187 A | 10/1999 | Parce et al. | | 6,259,635 B1 | 7/2001 | Torelli et al. |
| 5,973,138 A | 10/1999 | Collis | | 6,261,431 B1 | 7/2001 | Mathies et al. |
| D417,009 S | 11/1999 | Boyd | | 6,267,858 B1 | 7/2001 | Parce et al. |
| 5,976,336 A | 11/1999 | Dubrow et al. | | D446,306 S | 8/2001 | Ochi et al. |
| 5,980,704 A | 11/1999 | Cherukuri et al. | | 6,271,021 B1 | 8/2001 | Burns et al. |

| Patent | Date | Inventor |
|---|---|---|
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Kikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,871 B1 | 4/2002 | Christel et al. |
| 6,370,206 B1 | 4/2002 | Schenk |
| 6,375,185 B1 * | 4/2002 | Lin ............... 271/177 |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Majer et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | Mcreynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | Mcreynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| D482,796 S | 11/2003 | Oyama et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |

| Patent/Pub No. | Date | Name |
|---|---|---|
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Shinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | Mcreynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,330 B2 | 10/2007 | Chow et al. |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |
| D598,566 S | 8/2009 | Allaer |
| D599,234 S | 9/2009 | Ito |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,867,776 B2 | 1/2011 | Kennedy et al. |
| 7,892,819 B2 | 2/2011 | Wilding et al. |
| 7,998,708 B2 | 8/2011 | Handique et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0055765 A1 | 12/2001 | O'Keefe et al. |
| 2002/0001848 A1 | 1/2002 | Bedingham et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0049833 A1 | 3/2003 | Chen et al. |
| 2003/0064507 A1 | 4/2003 | Gallagher et al. |
| 2003/0070677 A1 | 4/2003 | Handique et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0199081 A1 | 10/2003 | Wilding et al. |
| 2003/0211517 A1 | 11/2003 | Carulli et al. |
| 2004/0014238 A1* | 1/2004 | Krug et al. .................. 422/100 |
| 2004/0029258 A1 | 2/2004 | Heaney et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0240097 A1 | 12/2004 | Evans |
| 2005/0009174 A1 | 1/2005 | Nikiforov et al. |
| 2005/0041525 A1 | 2/2005 | Pugia et al. |
| 2005/0048540 A1 | 3/2005 | Inami et al. |

| | | |
|---|---|---|
| 2005/0058574 A1 | 3/2005 | Bysouth et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0133370 A1 | 6/2005 | Park et al. |
| 2005/0135655 A1 | 6/2005 | Kopf-sill et al. |
| 2005/0152808 A1 | 7/2005 | Ganesan |
| 2005/0170362 A1 | 8/2005 | Wada et al. |
| 2005/0186585 A1 | 8/2005 | Juncosa et al. |
| 2005/0202470 A1 | 9/2005 | Sundberg et al. |
| 2005/0202504 A1 | 9/2005 | Anderson et al. |
| 2005/0208676 A1* | 9/2005 | Kahatt ............................ 422/100 |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1* | 6/2006 | Tajima et al. ................. 422/100 |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique et al. |
| 2006/0207944 A1 | 9/2006 | Siddiqi |
| 2006/0246493 A1 | 11/2006 | Jensen et al. |
| 2006/0246533 A1 | 11/2006 | Fathollahi et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0050804 A1 | 2/2008 | Handique et al. |
| 2008/0056948 A1 | 3/2008 | Dale et al. |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0182301 A1 | 7/2008 | Handique et al. |
| 2008/0192254 A1 | 8/2008 | Kim et al. |
| 2008/0247914 A1 | 10/2008 | Edens et al. |
| 2008/0262213 A1 | 10/2008 | Wu et al. |
| 2009/0047713 A1 | 2/2009 | Handique |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0221059 A1 | 9/2009 | Handique et al. |
| 2009/0223925 A1 | 9/2009 | Morse et al. |
| 2010/0009351 A1 | 1/2010 | Brahmasandra et al. |
| 2010/0173393 A1 | 7/2010 | Handique et al. |
| 2011/0027151 A1 | 2/2011 | Handique et al. |
| 2011/0207140 A1 | 8/2011 | Handique et al. |
| 2011/0210257 A9 | 9/2011 | Handique et al. |

FOREIGN PATENT DOCUMENTS

| | | |
|---|---|---|
| DE | 19929734 | 12/1999 |
| EP | 0766256 | 4/1997 |
| FR | 2672301 | 8/1992 |
| FR | 2795426 | 12/2000 |
| JP | 58212921 A | 12/1983 |
| JP | H07-290706 | 11/1995 |
| JP | 2001-515216 | 9/2001 |
| JP | A-2001-527220 | 12/2001 |
| JP | A-2003-500674 | 1/2003 |
| JP | 2005-514718 | 5/2005 |
| JP | A-2005-204661 | 8/2005 |
| WO | WO 88/06633 | 9/1988 |
| WO | WO 92/05443 | 4/1992 |
| WO | WO 98/00231 | 1/1998 |
| WO | WO 98/22625 | 5/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 2004/007081 | 1/2004 |
| WO | WO 2004074848 A1 * | 9/2004 |
| WO | WO 2005/011867 | 2/2005 |
| WO | WO 2005/108620 | 11/2005 |
| WO | WO 2006/079082 | 7/2006 |
| WO | WO 2008/060604 | 5/2008 |
| WO | WO 2009/012185 | 1/2009 |

OTHER PUBLICATIONS

Handique et al., 2001, Mathematical modeling of drop mixing in a split-type microchannel, J. Micromech Microeng, 11:548-554.
International Search Report and Written Opinion dated Apr. 4, 2008 for PCT/US07/07513.
International Search Report and Written Opinion for PCT/US07/024022 dated Jan. 5, 2009.
Bollet, C. et al., "A simple method for the isolation of chromosomal DNA from Gram positive or acid-fast bacteria", Nucleic Acids Research, vol. 19, No. 8 (1991), p. 1955.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Broyles, et al., "Sample Filtration, Concentration, and Separation Integrated on Microfluidic Devices" Analytical Chemistry (American Chemical Society), vol. 75 No. 11: pp. 2761-2767.
Burns et al., "An Integrated Nanoliter DNA Analysis Device", Science 282:484-487 (1998).
Carlen et al., "Paraffin Actuated Surface Micromachined Valve," in IEEE MEMS 2000 Conference, p. 381-385, Miyazaki, Japan, Jan. 2000.
Chung, Y. et al., "Microfluidic chip for high efficiency DNA extraction", Miniaturisation for Chemistry, Biology & Bioengineering, vol. 4, No. 2 (Apr. 2004), pp. 141-147.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, vol. 70, No. 9, pp. 2013-2017.

Khandurina, et al., Microfabricated Porous Membrane Structure for Sample Concentraction and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule DNA Amplification and Analysis in an Integrated Microfluidic Device, Analytical Chemistry, American Chemical Society, 2001, vol. 73, No. 3 pp. 565-570.

Livache, T. et al., "Polypyrrole DNA chip on a Silicon Device: Example of Hepatitis C Virus Genotyping", Analytical Biochemistry, vol. 255 (1998), pp. 188-194.

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Orchid BioSciences, Inc., www.orchid.com, Jul. 6, 2001.

Roche, et al. "Ectodermal commitment of insulin-producing cells derived from mouse embryonic stem cells" Faseb J (2005) 19: 1341-1343.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Yoza, Brandon et al., DNA extraction using bacterial magnetic particles modified with hyperbranched polyamidoamine dendrimer, Mar. 20, 2003, vol. 101, No. 3, 219-228.

Yoza, et al., "Fully Automated DNA Extraction fro Blood Using Magnetic Particles Modified with a Hyperbranched Polyamidomine Dendrimer", Journal of Bioscience and Bioengineering, 95(1):21-26, 2003.

Mascini et al., "DNA electrochemical biosensors", Fresenius J. Anal. Chem., 369: 15-22, (2001).

Nakagawa et al., Fabrication of amino silane-coated microchip for DNA extraction from whole blood, J of Biotechnology, Mar. 2, 2005, vol. 116, pp. 105-111.

Plambeck et al., "Electrochemical Studies of Antitumor Antibiotics", J. Electrochem Soc.: Electrochemical Science and Technology (1984), 131(11): 2556-2563.

Wang, "Survey and Summary, from DNA Biosensors to Gene Chips", Nucleic Acids Research, 28(16):3011-3016, (2000).

* cited by examiner

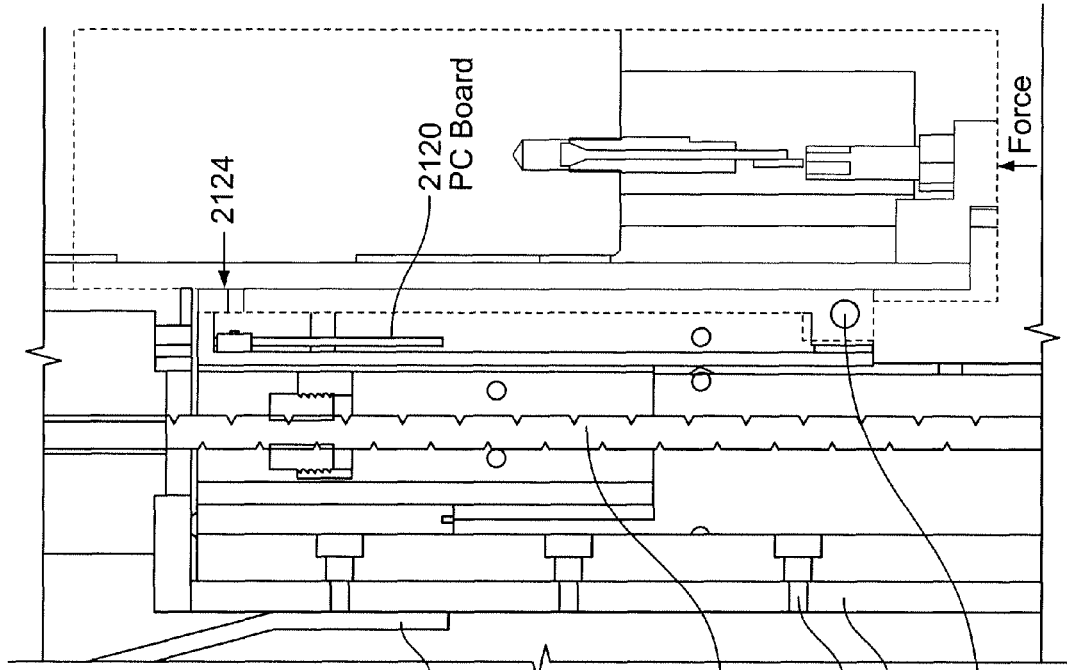
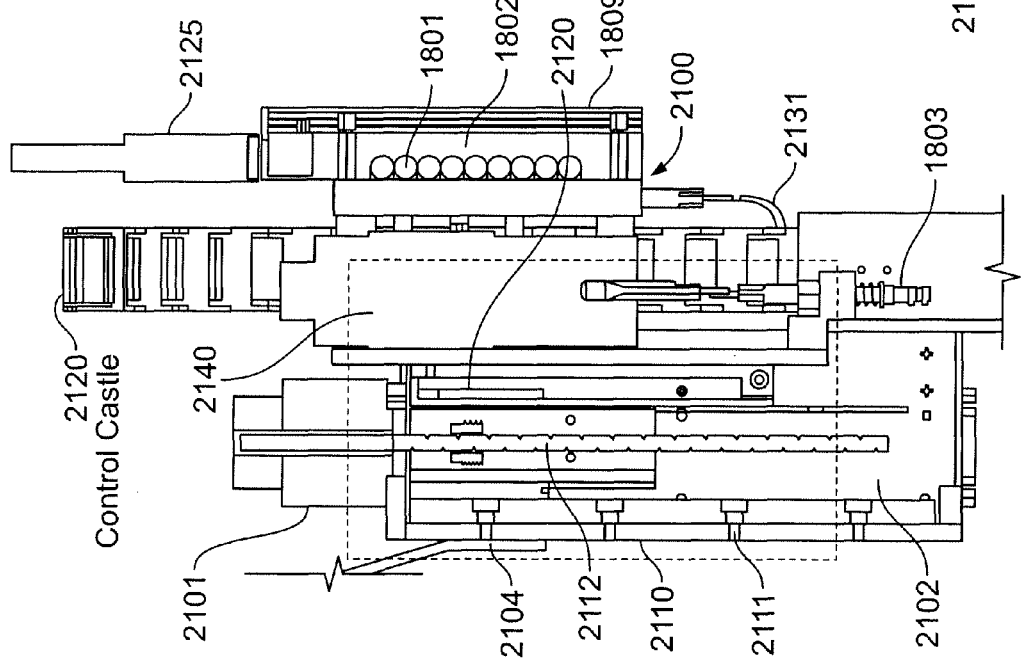
FIG. 13B
FIG. 13A

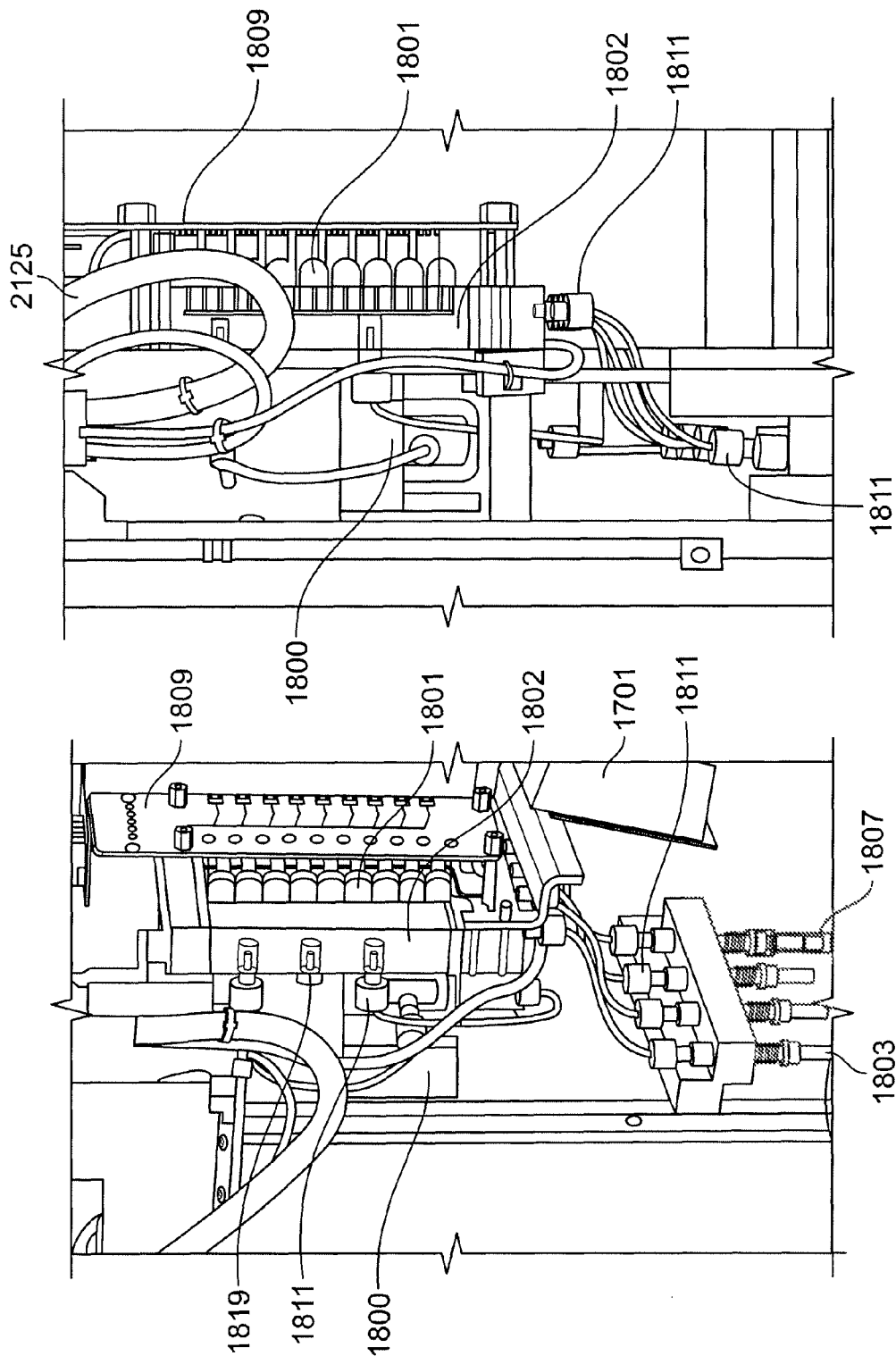

AUTOMATED PIPETTING APPARATUS HAVING A COMBINED LIQUID PUMP AND PIPETTE HEAD SYSTEM

RELATED APPLICATIONS

This application is a continuation-in-part of U.S. patent application Ser. No. 12/173,023, filed on Jul. 14, 2008, and is a continuation-in-part of U.S. patent application Ser. No. 12/218,498 filed on Jul. 14, 2008, both of which claim benefit of priority to U.S. provisional patent application Ser. No. 60/959,437, filed Jul. 13, 2007, all of which are incorporated herein by reference in their entireties.

TECHNICAL FIELD

The technology described herein generally relates to systems and methods for controlling fluid processing operations associated with extracting polynucleotides from samples, particularly multiple biological samples in parallel. The technology more particularly relates to automated pipetting systems that operate in conjunction with reagent containers and carry out various suck and dispense operations on various reagents in the containers, thereby bringing about mixing or disposal of those reagents.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss or mishandling. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Preparing samples for PCR is currently a time-consuming and labor intensive step, though not one requiring specialist skills, and could usefully be automated. By contrast, steps such as PCR and nucleotide detection have customarily only been within the compass of specially trained individuals having access to specialist equipment.

Sample preparation is labor intensive in part because of the number of reagents required, and the need for multiple liquid transfer (e.g., pipetting) operations. Thus, there is a need for an automated pipetting apparatus, particularly one that can operate on multiple samples in parallel.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The technology herein includes a liquid dispenser, comprising: one or more sensors; a manifold; one or more pumps in fluid communication with the manifold; one or more dispense heads in fluid communication with the manifold; and electrical connections that accept electrical signals from an external controller, wherein the liquid dispenser has no inlet or outlet for fluids, other than through the one or more pumps. The liquid dispenser further has a number of dispense heads, wherein each head is configured to accept a pipette tip.

The technology herein further includes an automated pipetting system that includes a liquid dispenser, the dispenser comprising: one or more sensors; a manifold; one or more pumps in fluid communication with the manifold; one or more dispense heads in fluid communication with the manifold; and electrical connections that accept electrical signals from an external controller, wherein the liquid dispenser has no inlet or outlet for fluids, other than through the one or more pumps.

The technology herein further includes an apparatus for carrying out sample preparation on multiple samples in parallel, the apparatus including an automated pipetting system configured to carry out liquid handling steps associated with sample preparation. The pipetting system includes a liquid dispenser, the dispenser comprising: one or more sensors; a manifold; one or more pumps in fluid communication with the manifold; one or more dispense heads in fluid communication with the manifold; and electrical connections that accept electrical signals from an external controller, wherein the liquid dispenser has no inlet or outlet for fluids, other than through the one or more pumps. The apparatus may further carry out diagnostic analysis on nucleotides put into form ready for amplification after sample preparation, where the automated pipetting system is configured to transfer those samples to a device that can amplify those samples and provide detectable quantities of amplified samples.

The technology herein further includes methods of sample preparation, comprising liquid handling steps that are performed on multiple samples in parallel by an automated pipetting system that includes a liquid dispenser as further described herein.

BRIEF DESCRIPTION OF THE DRAWINGS

FIGS. 13A and 13B show views of a liquid dispenser.

FIGS. 14A-14C show views of a liquid dispense head.

FIG. 15 shows an exemplary distribution manifold.

Like reference numerals in the various drawings indicate like elements.

DETAILED DESCRIPTION

The automated pipetting apparatus described herein is typically configured for use in a method and apparatus for carrying out sample preparation on biological samples in parallel, with or without PCR and detection on the prepared samples, and preferably with high throughput.

Figure 1:
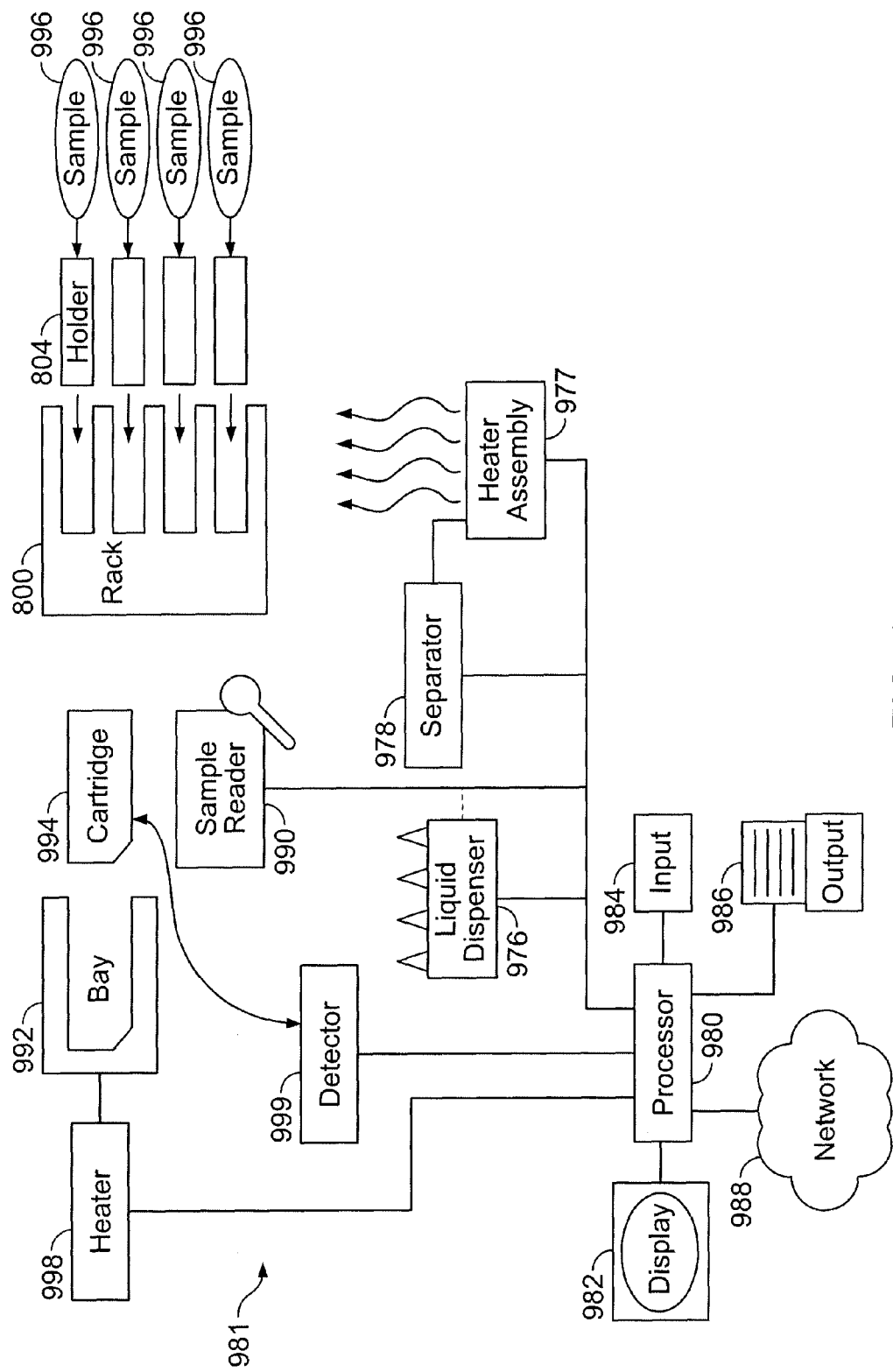
FIG. 1 shows a schematic of an automated apparatus configured to carry out sample preparation using a liquid dispenser as described herein.

Overview of a Preparatory or Diagnostic Apparatus that Incorporates a Liquid Dispenser A schematic overview of an apparatus 981 for carrying out automated sample preparation on multiple samples in parallel, according to steps exemplified elsewhere herein, is shown in FIG. 1. The geometric arrangement of the components of system 981 is exemplary and not intended to be limiting.

A processor 980, such as a microprocessor, is configured to control functions of various components of the system as shown, and is thereby in communication with each such component requiring control, for example via a bus. It is to be understood that many such control functions can optionally be carried out manually, and not under control of the processor. Furthermore, the order in which the various functions are described, in the following, is not limiting upon the order in which the processor executes instructions when the apparatus is operating. A suitable processor 980 can be designed and manufactured according to, respectively, design principles and semiconductor processing methods known in the art.

Processor 980 can be configured to accept user instructions from an input device 984, where such instructions may include instructions to start analyzing the sample, and choices of operating conditions. Processor 980 can be also configured to communicate with a display 982, so that, for example, information about an analysis is transmitted to the display and thereby communicated to a user of the system. Such information includes but is not limited to one or more of: the current status of the apparatus; progress of PCR thermocycling; and a warning message in case of malfunction of either system or cartridge. Additionally, processor 980 may transmit one or more questions to be displayed on display 982 that prompt a user to provide input in response thereto. Thus, in certain embodiments, input 984 and display 982 are integrated with one another.

Processor 980 can be optionally further configured to transmit results of an analysis to an output device 986 such as a printer, a visual display such as display 982 or a second display, a display that utilizes a holographic projection, or a speaker, or a combination thereof. Processor 980 can be still further optionally connected via a communication interface such as a network interface to a computer network 988.

Processor 980 can be further configured to control various aspects of sample preparation and diagnosis, as follows in overview. In FIG. 1, the apparatus 981 is configured to operate in conjunction with a complementary rack 970. Apparatus 981 may be capable of receiving multiple racks, such as 1, 2, 3, 4, or 6 racks.

Embodiments of rack 970 are further described in U.S. patent application Ser. No. 12/173,023, filed by ExpressMail on Jul. 14, 2008 (and entitled "Integrated Apparatus for Performing Nucleic Acid Extraction and Diagnostic Testing on Multiple Biological Samples", in the name of Williams, et al.), and Ser. No. 12/178,584, filed on Jul. 23, 2008, and entitled "Rack For Sample Tubes And Reagent Holders", in the name of Duffy, et al., both of which are incorporated herein by reference in their entireties. A rack 970 is itself configured to receive a number of biological samples 996, such as nucleic-acid containing samples, in a form suitable for work-up and subsequent diagnostic analysis, and a number of holders 972—as further described herein, such as in connection with FIG. 2—that are equipped with various reagents, pipette tips and receptacles. The rack is configured so that, during sample work-up, samples are processed in the respective holders, the processing including being subjected, individually, to heating and cooling via heater assembly 977.

The heating functions of the heater assembly 977 can be controlled by the processor 980. Heater assembly 977 operates in conjunction with a separator 978, such as a magnetic separator, that also can be controlled by processor 980 to move into and out of close proximity to one or more processing chambers associated with the holders 972, wherein particles such as magnetic particles are present. Assembly 977 and separator 978 are further described in U.S. patent application Ser. No. 12/178,586, filed on Jul. 23, 2008, and entitled "Integrated Heater and Magnetic Separator", in the name of Handique, which is incorporated herein by reference in its entirety.

Processor 980 can be configured to receive data about a sample to be analyzed, e.g., from a sample reader 990, which may be a barcode reader, an optical character reader, or an RFID scanner (radio frequency tag reader). Thus, sample reader 990 is configured to transmit identifying indicia about the sample, and in some instances the holder, to processor 980. In some embodiments, the sample reader is movable from one sample position to another. In some embodiments a sample reader is attached to the liquid dispenser 976 and can thereby read indicia about a sample above which the liquid dispenser is situated. In other embodiments the sample reader is not attached to the liquid dispenser and is independently movable, under control of the processor.

Liquid dispenser 976, which similarly can be controlled by processor 980 and is further described herein, is configured to automatically carry out various pipetting (e.g., suck and dispense) operations on respective samples in rack 970, and fluids and reagents in the holders 972, to achieve extraction of nucleic acid from the samples. Liquid dispenser 976 can carry out such operations on multiple holders simultaneously, and is further described herein.

Liquid dispenser 976 is also configured to take aliquots of fluid containing nucleic acid extracted from one or more samples and direct them to a storage area (not shown in FIG. 1), which may comprise a cooler or coolers. Such a storage area may contain, for example, a PCR tube corresponding to each sample and which can contain solutions of extracted nucleic acids dispensed by the liquid dispenser.

In the embodiment of a diagnostic apparatus shown in FIG. 1, a cartridge 994 is received in bay 992. The receiving bay is in communication with a heater 998 that itself can be controlled by processor 980 in such a way that specific regions of the cartridge 994 are heated at specific times during analysis. Liquid dispenser 976 is thus configured to take aliquots of fluid containing nucleic acid extracted from one or more samples and direct them to one or more respective inlets in cartridge 994. Cartridge 994 is configured to amplify, such as by providing chambers for carrying out PCR on, the respective nucleic acids. Exemplary cartridges are found described in U.S. patent application Ser. No. 12/173,023, filed Jul. 14, 2008, and incorporated herein by reference. The processor is also configured to control and receive data from a detector 999 that receives an indication of a diagnosis from the cartridge 994. The diagnosis can be transmitted to the output device 986 and/or the display 982, as described hereinabove.

Embodiments of the apparatus shown in outline in FIG. 1, as with other exemplary embodiments described herein, are advantageous because they do not require locations within the apparatus suitably configured for storage of reagents. Therefore, the apparatus in FIG. 1 is self-contained and operates in conjunction with holders 972, wherein the holders are prepackaged with reagents, such as in locations within it dedicated to reagent storage.

The apparatus of FIG. 1 may be configured to carry out operation in a single location, such as a laboratory setting, or may be portable so that they can accompany, e.g., a physician, or other healthcare professional, who may visit patients at different locations. The apparatus is typically provided with a power-cord so that it can accept AC power from a mains supply or generator. The apparatus may also be configured to operate by using one or more batteries and therefore is also typically equipped with a battery recharging system, and various warning devices that alert a user if battery power is becoming too low to reliably initiate or complete a diagnostic analysis.

The apparatus of FIG. 1 may further be configured, in other embodiments, for multiplexed sample analysis and/or analysis of multiple batches of samples, where, e.g., a single rack holds a single batch of samples. Each component shown in FIG. 1 may therefore be independently present as many times as there are batches of samples (or some fraction thereof), though the various components may be configured in a common housing.

In various embodiments, preparation of a PCR-ready sample for use in subsequent diagnosis using the apparatus as further described herein can include one or more of the following steps: contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid); in some embodiments, the PCR reagent mixture can be in the form of one or more lyophilized pellets, as stored in a receptacle on a holder, and the method can further include reconstituting the PCR pellet with liquid to create a PCR reagent mixture solution.

The apparatuses as described herein find application to analyzing any nucleic acid containing sample for any purpose, including but not limited to genetic testing, and clinical testing for various infectious diseases in humans.

The apparatus herein can be configured to run on a laboratory benchtop, or similar environment, and can test approximately 45 samples per hour when run continuously throughout a normal working day. Results from individual raw samples are typically available in less than 1 hour.

Figure 2A:
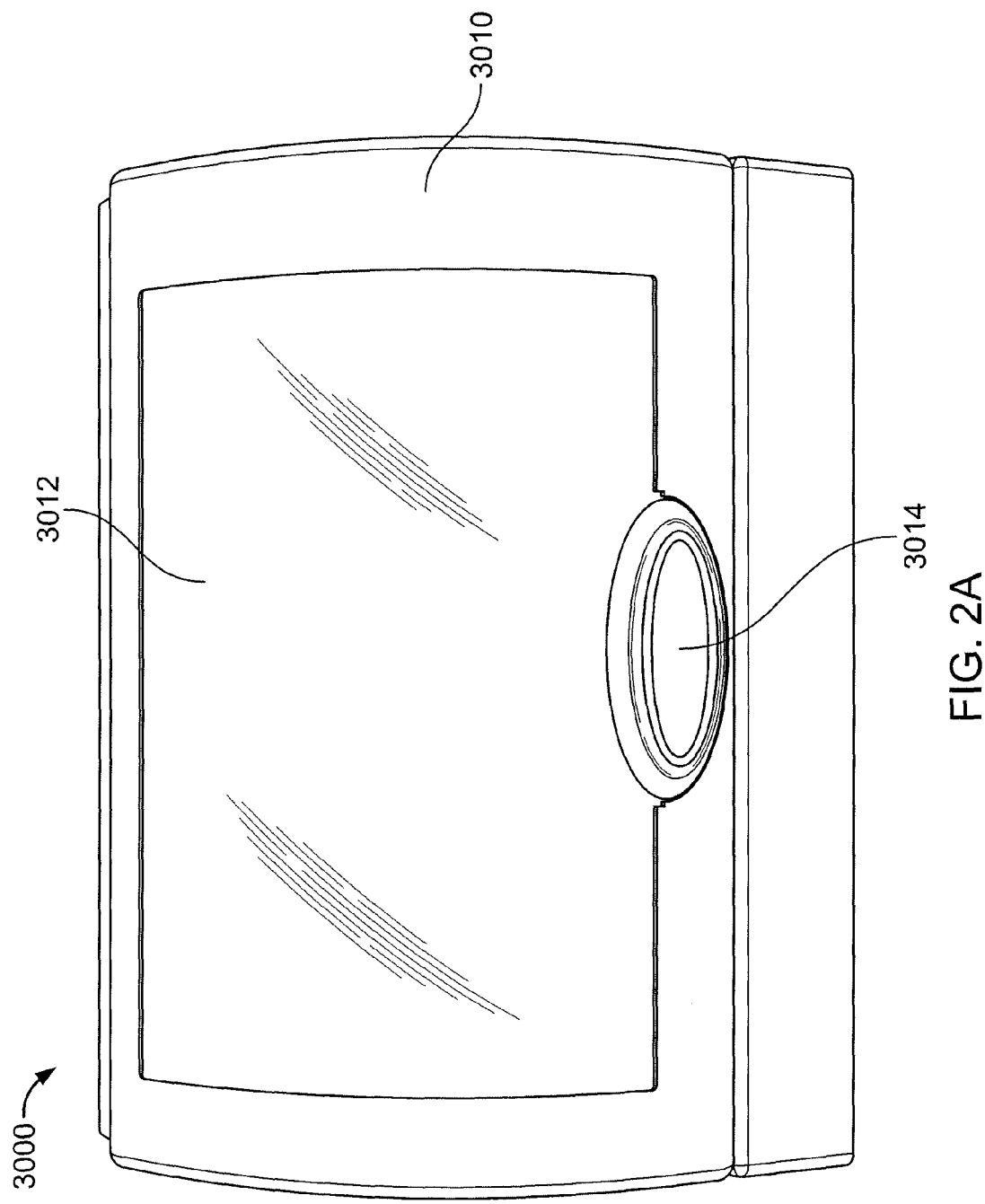
FIGS. 2A and 2B show views of the exterior and interior of an exemplary diagnostic apparatus.
Figure 2B:
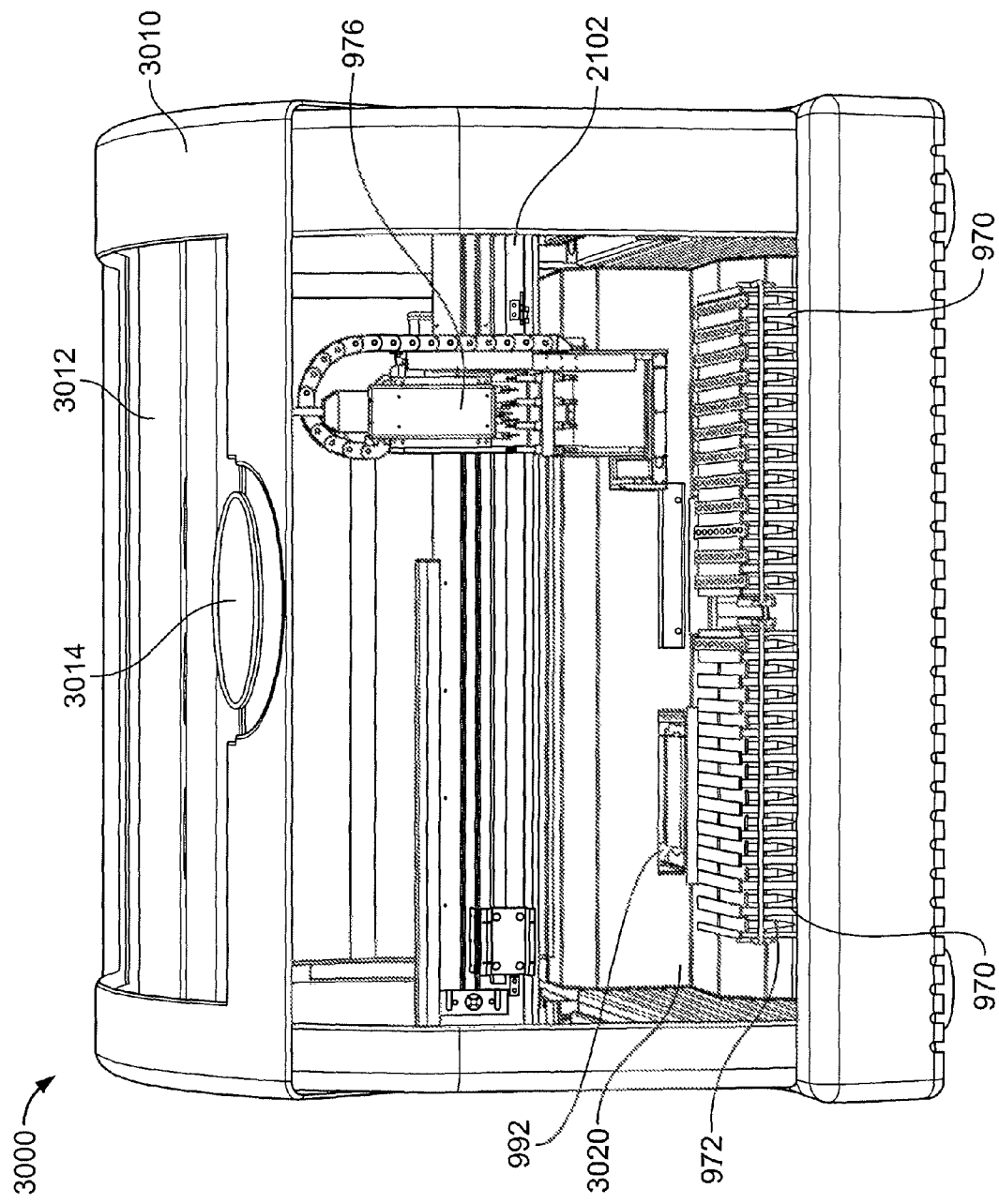

FIGS. 2A and 2B show views of an exemplary diagnostic apparatus 3000 incorporating various elements of FIG. 1. Shown in FIG. 2A, a front plan view of apparatus 3000 has a hinged cover 3010, shown in a closed position, bearing an optional clear window 3012 (that provides a user with an at-a-glance indication of the operational state of the apparatus), and a handle 3014 that facilitates opening and closing of the cover.

Shown in FIG. 2B is a front plan view of apparatus 3000 with cover 3010 moved to an open position revealing certain elements of the interior 3020 of the apparatus. Aspects of the interior of the apparatus that are visible in the view of FIG. 2B include: two removable racks 970, each bearing 12 holders 972, and a liquid dispenser 976, mounted on a gantry that can move along horizontal sliding rails 2102, as further described herein.

Reagent Holders

The automated diagnostic apparatus described herein is configured to carry out sample preparation on multiple samples by accessing more than one sample tube, and more than one reagent holder, simultaneously. Thus, the liquid dispense head, further described herein, is configured to extract and dispense volumes of liquid from various positions in one or more reagent holders, the holders being disposed in a suitably configured rack, as also described elsewhere herein.

Described herein are reagent holders for holding and transporting reagents for various purposes, in particular sample preparation in a clinical context, and configured to be received by a rack as described elsewhere herein. The reagent holders also typically provide a container, such as a process tube, in which various reagents can be mixed one with another and/or with a sample, and subjected to heating.

Exemplary reagent holders are further described in copending application Ser. No. 12/218,416, filed by Express-Mail on Jul. 14, 2008 (and entitled "Reagent Tube, Reagent Holder, and Kits Containing Same", in the name of Wilson, et al.) and incorporated herein by reference.

Figure 3A:
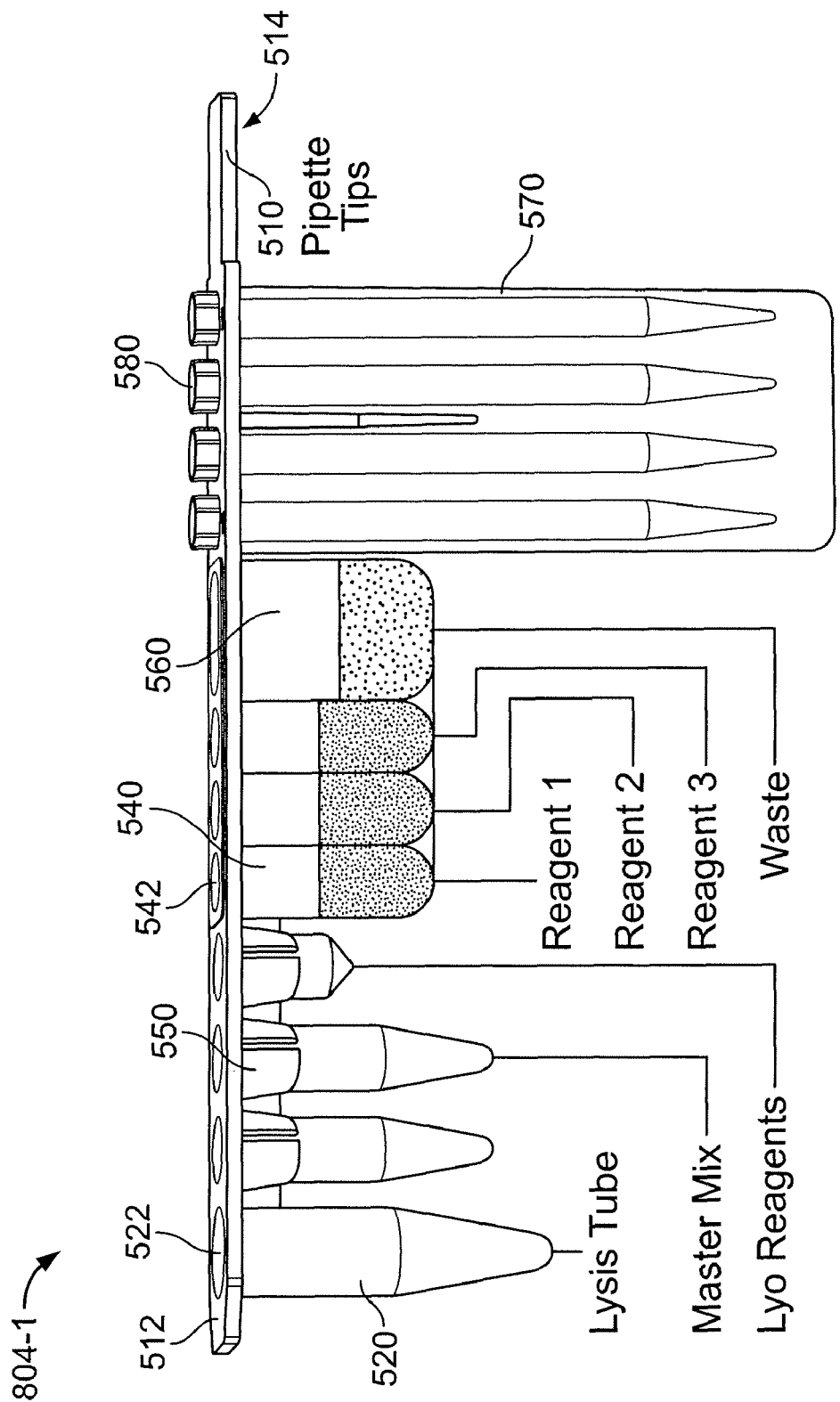
FIGS. 3A and 3B show an exemplary embodiment of a reagent holder, in side plan, and perspective, views.
Figure 3B:
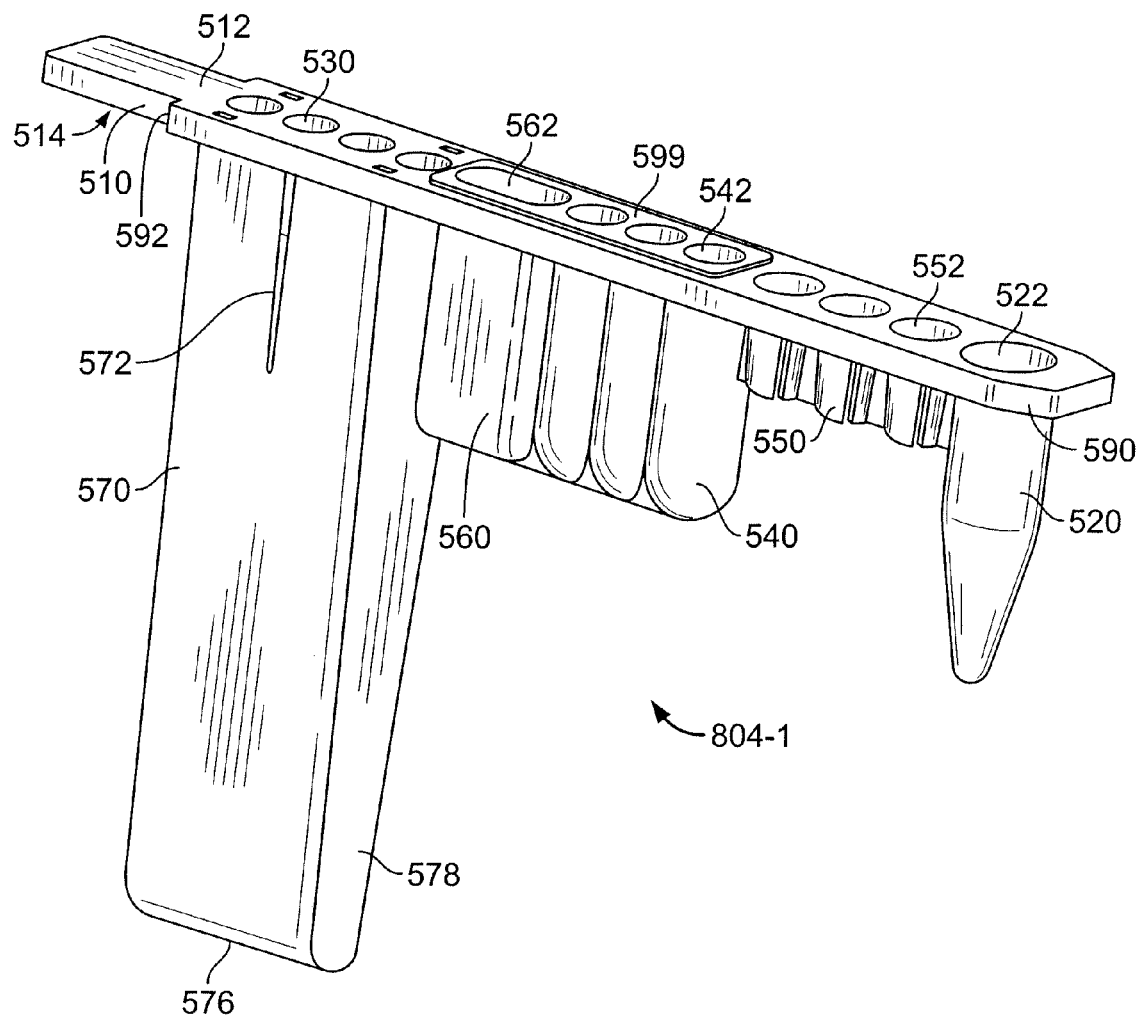
Figure 4:
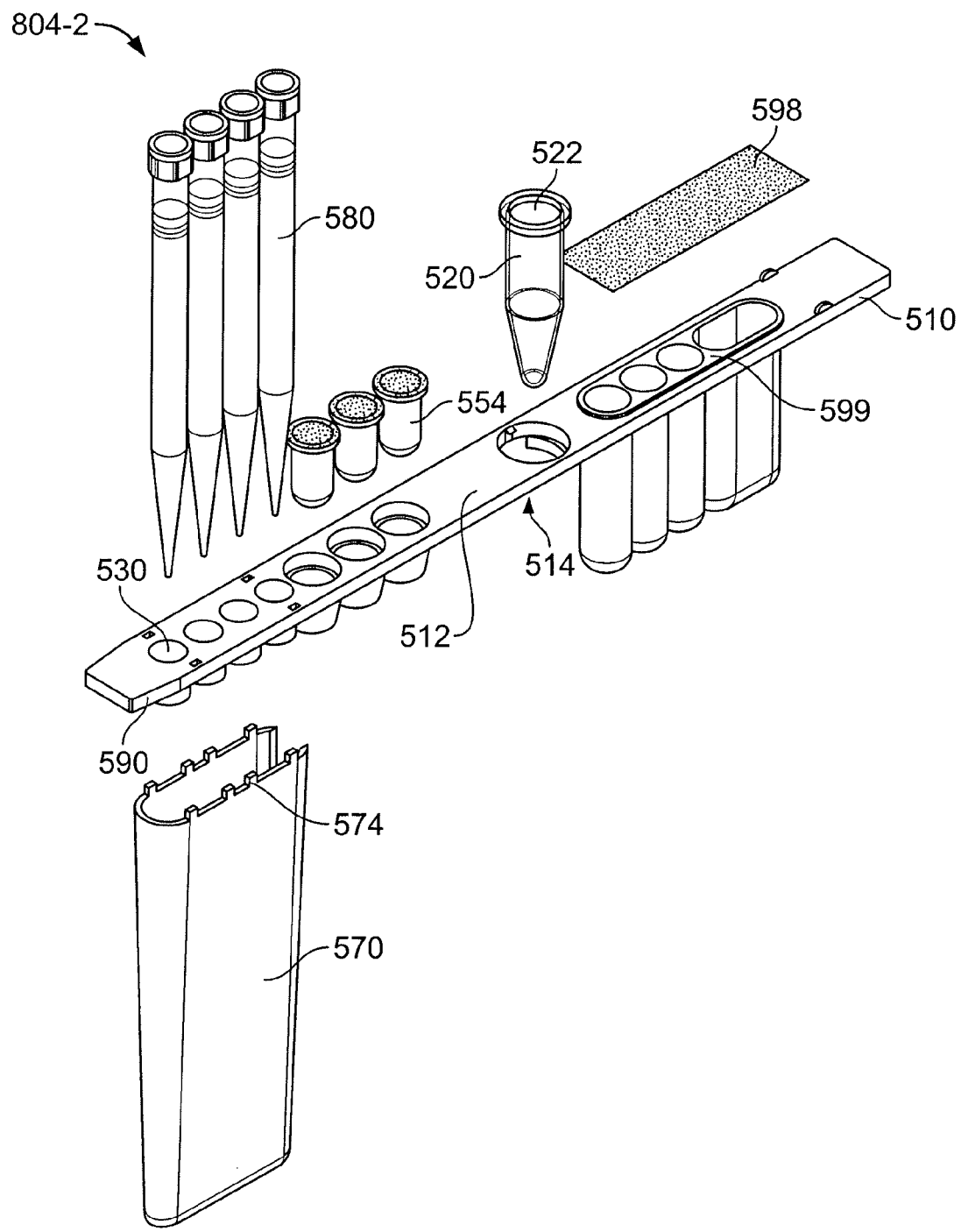
FIG. 4 shows a perspective view of a second exemplary embodiment of a reagent holder, in perspective view.

FIG. 3A shows a side plan view, and FIG. 3B shows a perspective view, of an exemplary holder 804-1 as further described herein. This exemplary holder, as well as others consistent with the written description herein though not shown as specific embodiments, are now described. FIG. 4 shows a second embodiment of a reagent holder 804-2, in perspective view, the holder having a different configuration of containers from that in FIGS. 3A and 3B. Like reference numerals in FIGS. 3A, 3B, and 4 refer to like elements in those respective figures. Holder embodiments 804-1 and 804-2 may be referred to collectively, herein as holder 804.

The exemplary holders of FIGS. 3A, 3B, and 4 comprise a connecting member 510 having one or more characteristics as follows. Connecting member 510 serves to connect various components of the holder together. Connecting member 510 has an upper side 512 and, opposed to the upper side, an underside 514.

The reagent holder of FIGS. 3A, 3B, and 4 are configured to comprise: a process tube 520 affixed to the connecting member and having an aperture 522 located in the connecting member; at least one socket 530, located in the connecting member, the socket configured to accept a disposable pipette tip 580; an optional pipette sheath 570 as further described herein; two or more reagent tubes 540 disposed on the underside of the connecting member, each of the reagent tubes having an inlet aperture 542 located in the connecting member; and one or more receptacles 550, located in the connecting member, wherein the one or more receptacles are each configured to receive a complementary container such as a reagent tube (not shown in FIG. 3B) inserted from the upper side 512 of the connecting member. Each of the apertures, and the corresponding openings of various complementary containers, is configured to accept a pipette tip, such as a standard laboratory pipette tip, during various pipetting operations such as dispensing fluid into, or sucking fluid out of, the one or more containers.

The one or more receptacles 550 are configured to accept container 554 that contain, respectively, sufficient quantities of one or more reagents typically in solid form, such as in lyophilized form, for carrying out extraction of nucleic acids from a sample that is associated with the holder. The receptacles can be all of the same size and shape, or may be of different sizes and shapes from one another. Preferably the receptacles 550 are configured to accept commonly used containers in the field of laboratory analysis, or containers suitably configured for use with the holder herein. The containers may be snap-in reagent tubes that maintain a steady position in the holder during pipetting operations thereon.

The containers that contain solid reagents such as lyophilized reagents, can be sealed across their tops by a metal foil, such as a single layer of an aluminum foil, with no plastic lining layer, as further described herein.

The containers containing different reagents may be of different colors, or color-coded for easy identification by the user. For example they may be made of different color material, such as tinted plastic, or may have some kind of identifying tag on them, such as a color stripe or dot. They may also have a label printed on the side, and/or may have an identifier such as a 1-D or a 2-D barcode on the sealing layer on the top, or on the side of the tube. Such a code is useful for identifying the composition of the reagents stored within, and/or a batch number for the preparation thereof, and/or an expiry date. The code may be printed on with, for example, an inkjet or transfer printer.

In one embodiment, the containers 554 containing lyophilized reagents, disposed in the receptacles 550, are 0.3 ml tubes that have been further configured to have a star-shaped pattern on their respective bottom interior surfaces. This is so that when a fluid has been added to the lyophilized reagents (which are dry in the initial package), a pipette tip can be bottomed out in the tube and still be able to withdraw almost the entire fluid from the tube. The design of the star-pattern is further described elsewhere in U.S. patent application Ser. No. 12/178,557, filed on Jul. 23, 2008, and entitled "Reagent Tube", in the name of Handique et al., which application is incorporated herein by reference. Still other containers used in conjunction with the holder herein may be similarly configured with a start-shaped pattern to increase pipetting efficiency.

The embodiments of reagent holders 804 are shown configured with a waste chamber 560, having an inlet aperture 562 in the upper side of the connecting member. Waste chamber 560 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed.

The embodiments of reagent holders 804 are shown having a pipette sheath 570. This is an optional component of the holders described herein. It may be permanently or removably affixed to connecting member 510, or may be formed, e.g., moulded, as a part of a single piece assembly for the holder. Pipette sheath 570 is typically configured to surround the at least one socket and a tip and lower portion of a pipette tip when the pipette tip is stationed in the at least one socket. In some embodiments, the at least one socket comprises four sockets. In some embodiments the at least one socket comprises two, three, five, or six sockets. The sheath and sockets are large enough to accommodate a variety of sizes of pipette tips, such as those having volumes as small as 10 µl to as large as 1 ml.

Pipette sheath 570 typically is configured to have a bottom 576 and a walled portion 578 disposed between the bottom and the connecting member. Pipette sheath 570 may additionally and optionally have one or more cut-out portions 572 in the wall 578, or in the bottom 576. In embodiments of the reagent holder having a pipette sheath, a purpose of the sheath is to catch drips from used pipette tips, and thereby to prevent cross-sample contamination, from use of one holder to another in a similar location, and/or to any supporting rack in which the holder is situated. Typically, then, the bottom 576 is solid and bowl-shaped (concave) so that drips are retained within it. An embodiment having no pipette sheath, could utilize, e.g., a drip tray or a drainage outlet, suitably placed beneath pipette tips located in the one or more sockets, for the same purpose and located under or in the bottom of the rack, as described herein.

Process tube 520 (sometimes referred to as a lysis tube) can also be a snap-in tube, rather than being part of an integrated piece. Process tube 520 is typically used for various mixing and reacting processes that occur during sample preparation. For example, cell lysis can occur in process tube 520, as can extraction of nucleic acids, such as DNA or RNA of a patient, or DNA or RNA of a pathogen. Process tube 520 is then advantageously positioned in a location that minimizes, overall, pipette head moving operations involved with transferring liquids to process tube 520. Process tube 520 is also located in the holder in such a position that, when the holder is inserted in a rack as further described herein, the process tube is exposed and accessible to a heater and separator, as further described herein. The process tube is typically configured to accept a pipette tip during multiple pipetting operations.

The process tube also may have a low binding surface, and allows magnetic beads to slide up and down the inside wall easily without sticking to it. Moreover, it has a hydrophobic surface coating enabling low stiction of fluid and hence low binding of nucleic acids and other molecules.

Some of the reagents contained in the holder are provided as liquids, and others may be provided as solids from which a solution is re-generated, in situ, by adding liquid from a pipette tip. In some embodiments, a different type of container or tube is used to store liquids from those that store the solids.

Reagent tubes 540 are typically configured to hold liquid reagents, one per tube. For example, in reagent holder embodiment 501, three reagent tubes are shown, containing respectively wash buffer, release buffer, and neutralization buffer, each of which is used in a sample preparation protocol, carried out with multiple pipetting operations controlled by, e.g., a pipette head as further described herein.

Reagent tubes 540 that hold liquids or liquid reagents can be sealed with a laminate structure 598. The laminate structure typically has a heat seal layer, a plastic layer such as a layer of polypropylene, and a layer of metal such as aluminum foil, wherein the heat seal layer is adjacent the one or more reagent tubes. The additional plastic film that is used in a laminate for receptacles that contain liquid reagents is typically to prevent liquid from contacting the aluminum.

Figure 5:
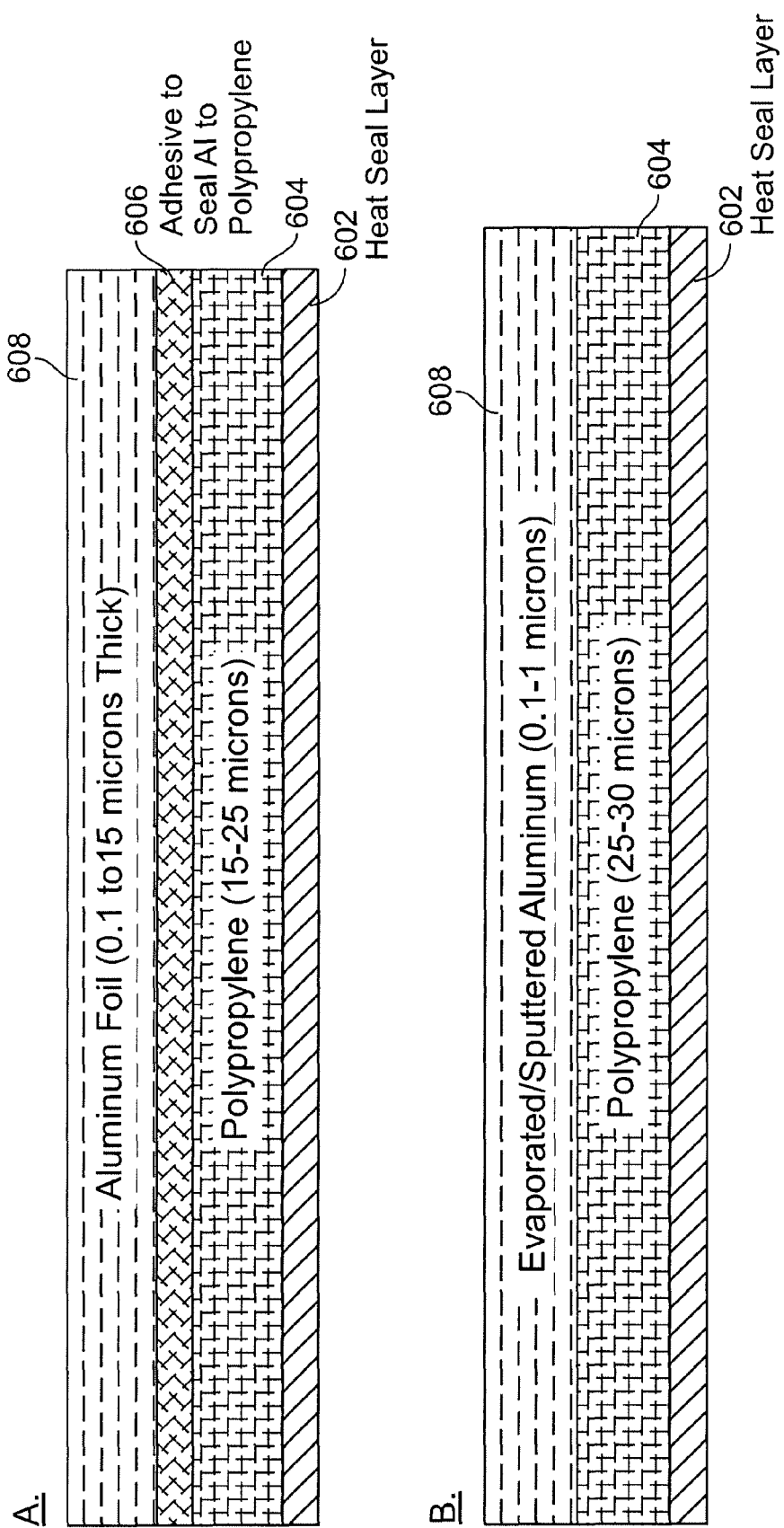
FIG. 5 shows embodiments of a laminated structures used to seal liquid containing tubes.

Two embodiments of a laminate structure, differing in their layer structures, are shown in FIG. 5. In both embodiments, the heat seal layer 602, for example made of a laquer or other such polymer with a low melting point, is at the bottom, adjacent to the top of the holder, when so applied. The plastic layer 604 is typically on top of the heat seal layer, and is typically made of polypropylene, having a thickness in the range 10-50 microns. The metal layer 608 is typically on top of the plastic layer and, in one embodiment, may be a layer of Al foil bonded to the plastic layer with a layer of adhesive 606, as in panel A of FIG. 5, or, in another embodiment, may be a layer of metal that is evaporated or sputtered into place directly on to the plastic layer (panel B of FIG. 5). Exemplary thicknesses for the respective layers are shown in FIG. 5, where it is to be understood that variations of up to a factor of 2 in thickness are consistent with the technology herein. In particular, the aluminum foil is 0.1-15 microns thick, and the polymer layer is 15-25 microns thick in one embodiment. In another embodiment, the aluminum is 0.1-1 microns thick, and the polymer layer is 25-30 microns thick.

The laminates deployed herein make longer term storage of reagents easier because the holder includes both sealed lyophilized reagents and liquids sealed in close proximity, which is normally hard to achieve.

In one embodiment, the tops of the reagent tubes have beveled edges so that when an aluminum foil is heat bonded to the top, the plastic melt does not extend beyond the rim of the tube. This is advantageous because, if the plastic melt reduces the inner diameter of the tube, it will cause interference with the pipette tip during operation. In other embodiments, a raised flat portion 599 on holders 804 facilitates application and removal of laminate 598. Raised surface 599, on the upper side of the connecting member, and surrounding the inlet apertures to the reagent tubes and, optionally, the waste chamber, is an optional feature of the holder.

Figure 6:
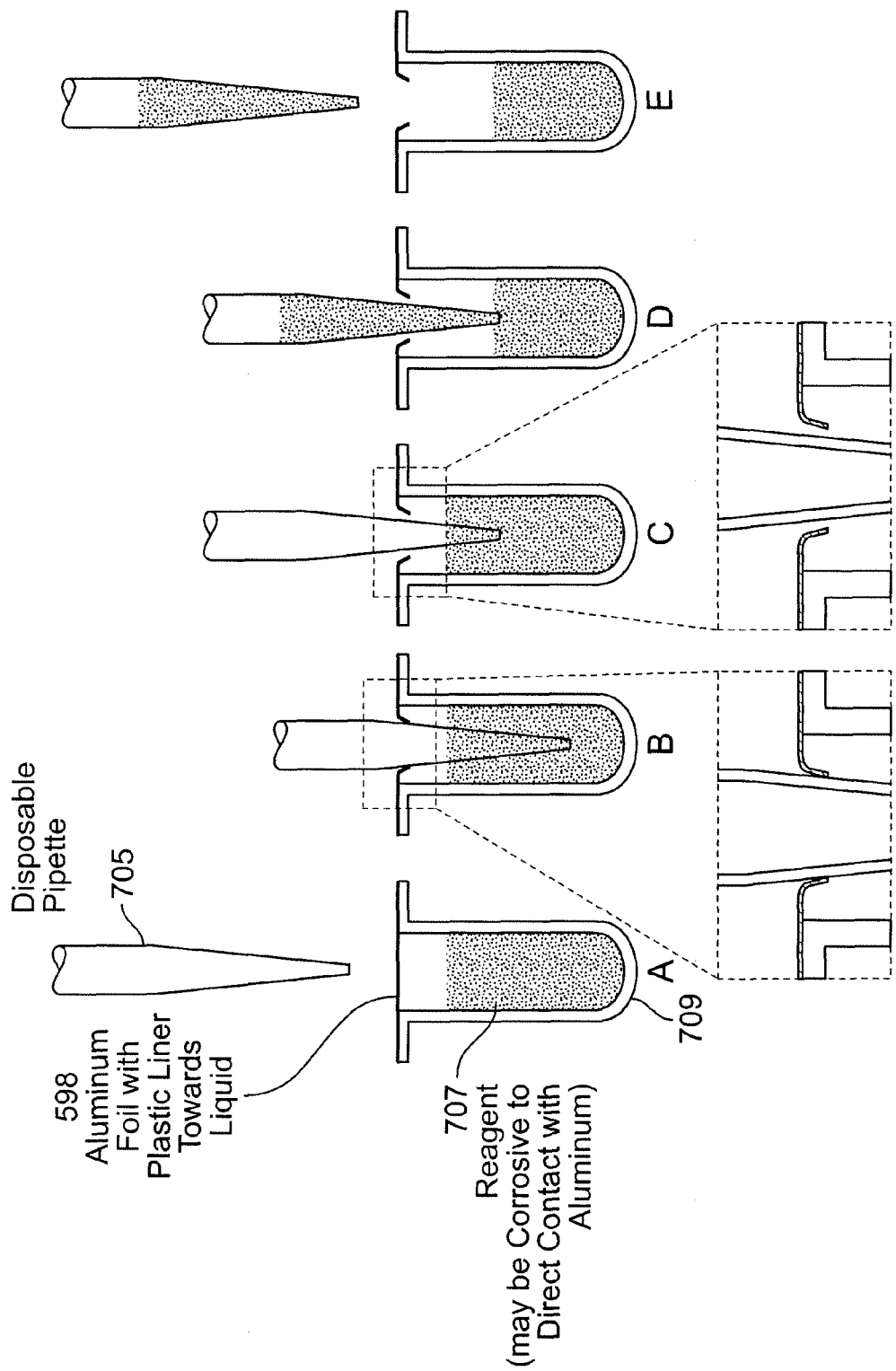
FIG. 6 shows a sequence of pipetting operations in conjunction with a laminated layer, as in FIG. 5.

The manner in which liquid is pipetted out is such that a pipette tip piercing through the foil rips through without creating a seal around the pipette tip, as illustrated in FIG. 6. Such a seal around the tip during pipetting would be disadvantageous because a certain amount of air flow is desirable for the pipetting operation. In this instance, a seal is not created because the laminate structure causes the pierced foil to stay in the position initially adopted when it is pierced. The upper five panels in FIG. 6 illustrate, in sequence, the pipetting of a reagent 707 (which may be corrosive to direct contact with Aluminum) out from a reagent tube 709 sealed with a laminate 598 as further described herein. At A, the pipette tip is positioned approximately centrally above the reagent tube that contains reagent 707. At B, the pipette tip 705 is lowered, usually controllably lowered, into the reagent tube, and in so doing pierces the laminate 598. The exploded view of this area shows the edge of the pierced laminate to be in contact with the pipette tip at the widest portion at which it penetrates the reagent tube. At C, the pipette tip is withdrawn slightly, maintaining the tip within the bulk of the reagent 707. The exploded view shows that the pierced foil has retained the configuration that it adopted when it was pierced and the pipette tip descended to its deepest position within the reagent tube. At D, the pipette tip sucks up reagent 707, possibly altering its height (without bottoming out) as more reagent is removed from the tube. At E, the pipette tip is removed entirely from the reagent tube.

The reagent holder of embodiments 804 has a connecting member 510 that is configured so that the at least one socket, the one or more receptacles, and the respective apertures of the process tube, and the two or more reagent tubes, are all arranged linearly with respect to one another (i.e., their midpoints lie on the same axis). However, the holders herein are not limited to particular configurations of receptacles, process tube, sockets, reagent tubes, and waste chamber if present. For example, a holder may be made shorter, if some apertures are staggered with respect to one another and occupy 'off-axis' positions. The various receptacles, etc., also do not need to occupy positions with respect to one another that are the same as those shown in FIG. 3A, 3B, or 4. Thus, in FIGS. 3A and 3B, the process tube is on one end of the connecting member, and the pipette sheath is at the other end, adjacent to, in an interior position, a waste chamber and two or more reagent tubes. Still other dispositions are possible, such as mounting the process tube on one end of the holder, mounting the process tube adjacent the pipette tips and pipette tip sheath, and mounting the waste tube adjacent the process tube (see FIG. 4). It would be understood that alternative configurations of the various parts of the holder give rise only to variations of form and can be accommodated within other variations of the apparatus as described, including but not limited to alternative instruction sets for a liquid dispensing pipette head, heater assembly, and magnetic separator, as further described herein. Each such configuration of the reagent holder can be accommodated by a corresponding variation in form of the rack described herein that receives one or more such holders.

In some embodiments, the holder comprises a registration member such as a mechanical key. Typically such a key is part of the connecting member 510. A mechanical key ensures that the holder is accepted by a complementary member in, for example, a supporting rack as described herein or a receiving bay of an apparatus that controls pipetting operations on reagents in the holder. Thus, embodiment 501 has a mechanical key 592 that comprises a pair of rectangular-shaped cutouts on one end of the connecting member. This feature as shown additionally provides for a tab by which a user may gain a suitable purchase when inserting and removing the holder into a rack or another apparatus. Embodiment 501 also has a mechanical key 590 at the other end of connecting member 510. Key 590 is an angled cutout that eases insertion of the holder into a rack, as well as ensures a good registration therein when abutting a complementary angled cut out in a recessed area configured to receive the holder.

In some embodiments, not shown in FIG. 3A, 3B, or 4, the holder further comprises an identifier affixed to the connecting member. The identifier may be a label, such as a writable label, a bar-code, a 2-dimensional bar-code, or an RFID tag. The identifier can be, e.g., for the purpose of revealing quickly what combination of reagents is present in the holder and, thus, for what type of sample preparation protocol it is intended. The identifier may also indicate the batch from which the holder was made, for quality control or record-keeping purposes. The identifier may also permit a user to match a particular holder with a particular sample.

It should also be considered consistent with the description herein that a holder additionally can be configured to accept a sample, such as in a sample tube. Thus, in embodiments described elsewhere herein, a rack accepts a number of sample tubes and a number of corresponding holders in such a manner that the sample tubes and holders can be separately and independently loaded from one another. Nevertheless, in other embodiments, a holder can be configured to also accept a sample, for example in a sample tube. And thus, a complementary rack is configured to accept a number of holders, wherein each holder has a sample as well as reagents and other items. In such an embodiment, the holder is configured so that the sample in a suitably marked tube or container is accessible to a sample identification verifier.

A reagent holder for use with a rack as described herein is typically made of a plastic such as polypropylene. The plastic is such that it has some flexibility to facilitate placement into a rack, as further described herein. The plastic is typically sufficiently rigid, however, so that the holder will not significantly sag or flex under its own weight and will not easily deform during routine handling and transport or pipetting operations as further described herein, and thus will not permit reagents to leak out from it.

The holder is typically such that the connecting member, process tube, the two or more reagent tubes, and the waste chamber (if present) are made from a single piece, made from a material such as polypropylene.

The materials of the various tubes and chambers may be configured to have at least an interior surface smoothness and surface coating to reduce binding of DNA and other macromolecules thereto. Binding of DNA is unwanted because of the reduced sensitivity that is likely to result in subsequent detection and analysis of the DNA that is not trapped on the surface of the holder.

Rack

The apparatus outlined herein, and also described in U.S. patent application Ser. No. 12/173,023, filed by ExpressMail on Jul. 14, 2008 (and entitled "Integrated Apparatus for Performing Nucleic Acid Extraction and Diagnostic Testing on Multiple Biological Samples", in the name of Williams, et al.), incorporated by reference herein, is configured to carry out various liquid transfer operations on samples and various reagents, in parallel. The samples and various reagents are typically held in one or more removable racks 970, positioned in the apparatus (such as one shown in FIG. 1, 2A, or 2B), while the various liquid transfer operations are carried out. Optionally, the operations can be carried out on the reagents, stored in holders located directly in the apparatus, without use of a removable rack.

The racks for use herein are typically configured to be insertable into, and removable from, a diagnostic or preparatory apparatus as further described herein (e.g., in connection with FIGS. 1, 2A and 2B), each of the racks being further configured to receive a plurality of reagent holders, and to receive a plurality of sample tubes, wherein the reagent holders are in one-to-one correspondence with the sample tubes, and wherein the reagent holders each contain sufficient reagents to extract polynucleotides from a sample and to place the polynucleotides into a PCR-ready form. Exemplary racks are further described in U.S. patent application Ser. No. 12/178,584, filed Jul. 23, 2008, to Duffy et al., incorporated herein by reference in its entirety.

Figure 7:
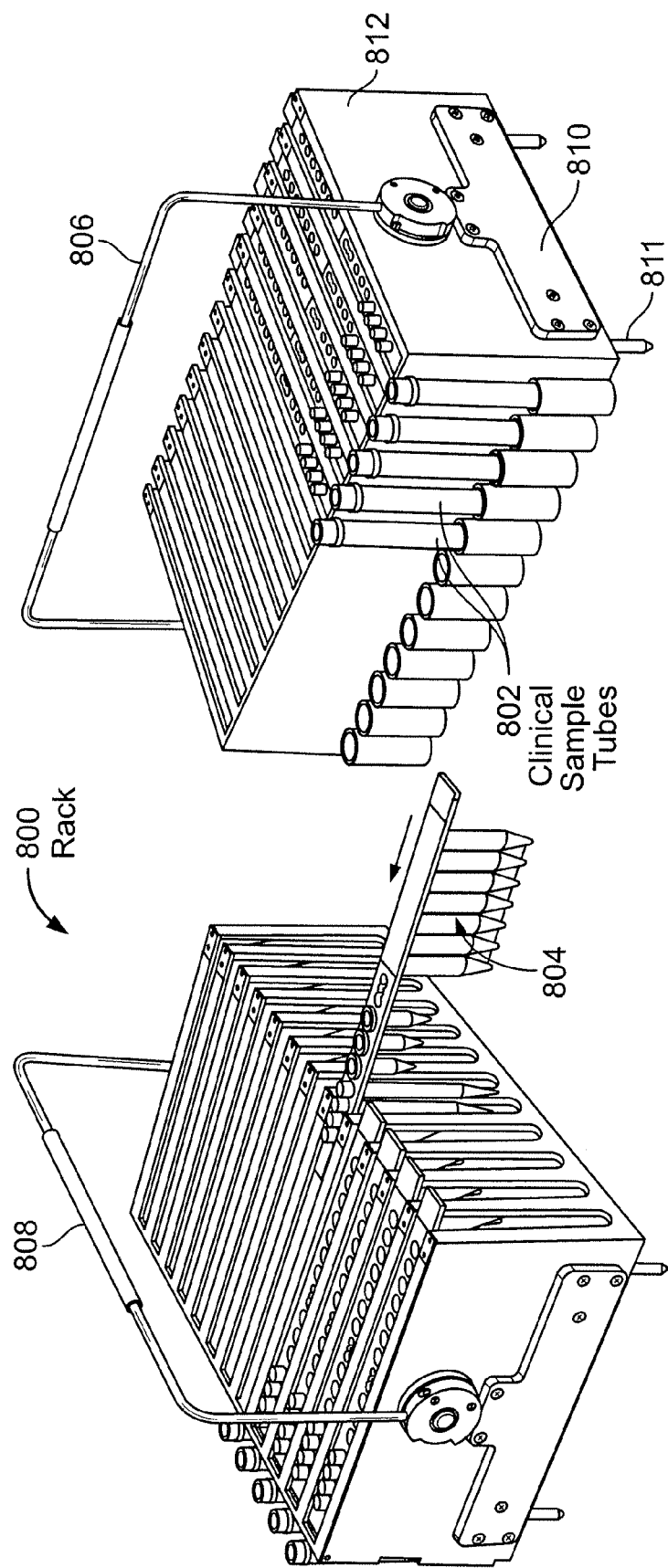
FIG. 7 shows perspective views of an exemplary rack for samples and reagent holders.
Figure 8:
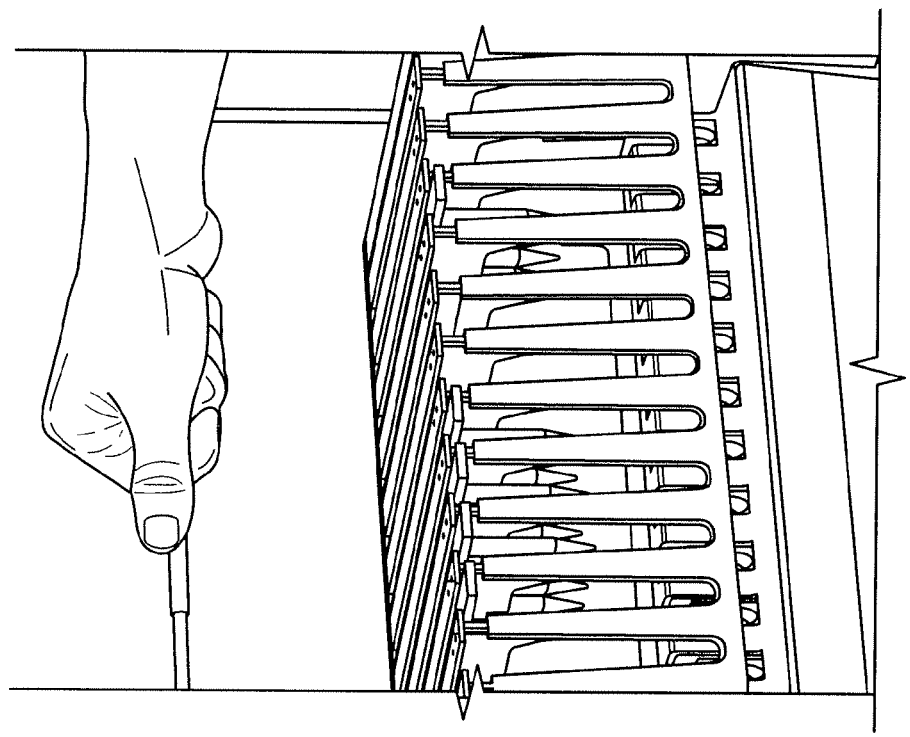
FIG. 8 shows perspective views of the rack of reagent holders and sample tubes of FIG. 7, in conjunction with a heater unit.
Figure 8:
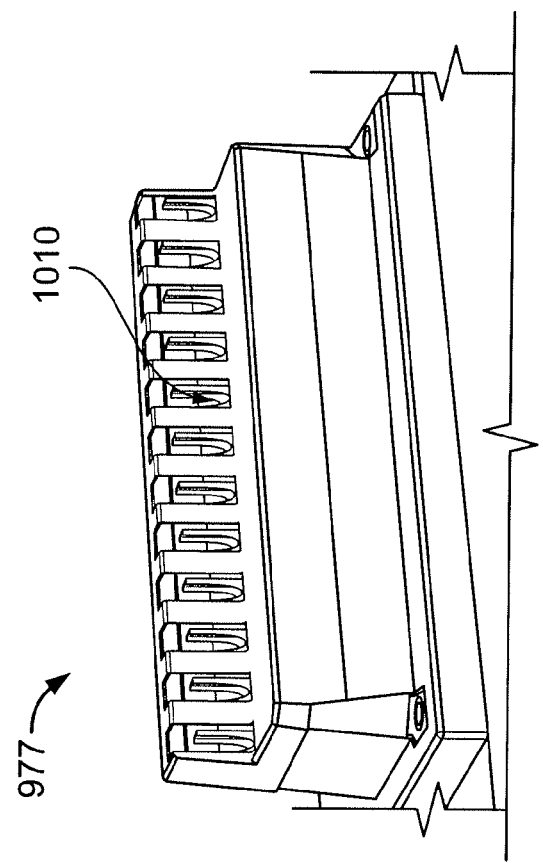

Two perspective views of an exemplary rack 800, configured to accept 12 sample tubes and 12 corresponding reagent holders, in 12 lanes, are shown in FIG. 7. A lane, as used herein in the context of a rack, is a dedicated region of the rack designed to receive a sample tube and corresponding reagent holder. A perspective view of the same exemplary rack, in conjunction with a heater unit, as further described herein, is shown in FIG. 8. The lanes of the rack described herein are designed to have sufficient depth and width to accommodate the various reagent tubes, receptacles, process tube, and pipette sheath of a given reagent holder as described elsewhere herein, and to position the process tube in communication with a heater/separator unit.

A rack may accept 2, 4, 6, 8, 10, 12, 16, or 20 samples such as in sample tubes 802, and a corresponding number of reagent holders 804. Thus the embodiment of FIG. 8, configured to receive 12 samples in sample tubes 802, and 12 corresponding reagent holders 804, is exemplary.

Rack 800 is shown with a handle 806, having optionally a hand-grip 808, to facilitate transport, and removal from the apparatus. Rack 800 is also shown with positioning feet 811 that can help stabilize the rack during loading and when resting on, e.g., a bench-top, outside of the apparatus. Rack 800 is also shown as having a structural member 810, typically made of steel, that provides strength and rigidity for the rack, and also ensures that the rack fits tightly into an appropriately configured receiving area of the apparatus. Rack 800 is also shown as having a body 812 configured with a number of slots that accept the reagent holders.

As described elsewhere herein, the holders each comprise a process tube in which reactions, e.g., between reagents and sample, take place, typically with some heating, or cyclical heating and cooling. The location of the reagent holders in the rack typically ensures that the process tubes are effectively located in proximity to the heater units, as shown in FIG. 8.

Heater Assembly & Magnetic Separator

The racks as described herein are configured such that the reagent holders placed in the racks are positioned so that the process tubes in the holders are heated by a dedicated heating assembly 977, as may be situated in an apparatus for carrying out sample preparation and analysis on multiple samples in parallel, such as shown in FIG. 1, 2A or 2B. Typically such a heater assembly comprises one or more independently controllable heater units 1010, each of which comprises a heat block configured to heat a process tube in a reagent holder situated in the rack, as further described herein. In one embodiment, a heat element is a power resistor. The right hand panel of FIG. 8 shows how holders loaded in a rack can be positioned in close proximity to such a dedicated heating unit. The heating unit is configured to heat the process tube in each of one or more reagent holders positioned in the rack, without unduly heating other portions of the rack, or other containers associated with the reagent holders.

Yet additionally, the holders herein are configured so that each process tube is in close enough proximity to a magnetic assembly that separation of magnetic particles from reagents in solution in the process tubes can be accomplished. An exemplary magnetic separator is configured to move one or more magnets relative to the one or more process tubes. Typically, the magnet is mounted in such a way that it can be moved in proximity to the process tubes, either in an automated fashion such as under control of a processor, or manually. The magnet can be made of neodymium (e.g., from K&J Magnetics, Inc.) and can have a magnetic strength of 5,000-15,000 Gauss (Brmax). The poles of the magnets can be arranged such that one pole faces the heat blocks and the other faces away from the heat blocks.

Advantageously, the heater assembly and magnetic separator operate together to permit successive heating and separation operations to be performed on liquid materials in the one or more process tubes without transporting either the liquid materials or the process tubes to different locations to perform either heating or separation. An exemplary heater assembly and magnetic separator are further described in U.S. provisional Patent Application Ser. No. 60/959,437, filed Jul. 13, 2008, and U.S. patent application Ser. No. 12/173,023, filed Jul. 14, 2008, entitled "Integrated Apparatus for Performing Nucleic Acid Extraction and Diagnostic Testing on Multiple Biological Samples", in the name of Williams, et al., and Ser. No. 12/178,586, entitled "Integrated Heater and Magnetic Separator", in the name of Handique, filed on Jul. 23, 2008, all of which are incorporated herein by reference in their entirety.

The heater assembly and magnetic separator are also configured to operate in conjunction with the liquid dispenser further described herein so that, when appropriate quantities of liquid reagents and/or sample have been dispensed into the process tube adjacent the heater and separator, the heater and separator are controllably activated to accomplish the required heating and/or separating.

Pipetting Operations

Figure 9:
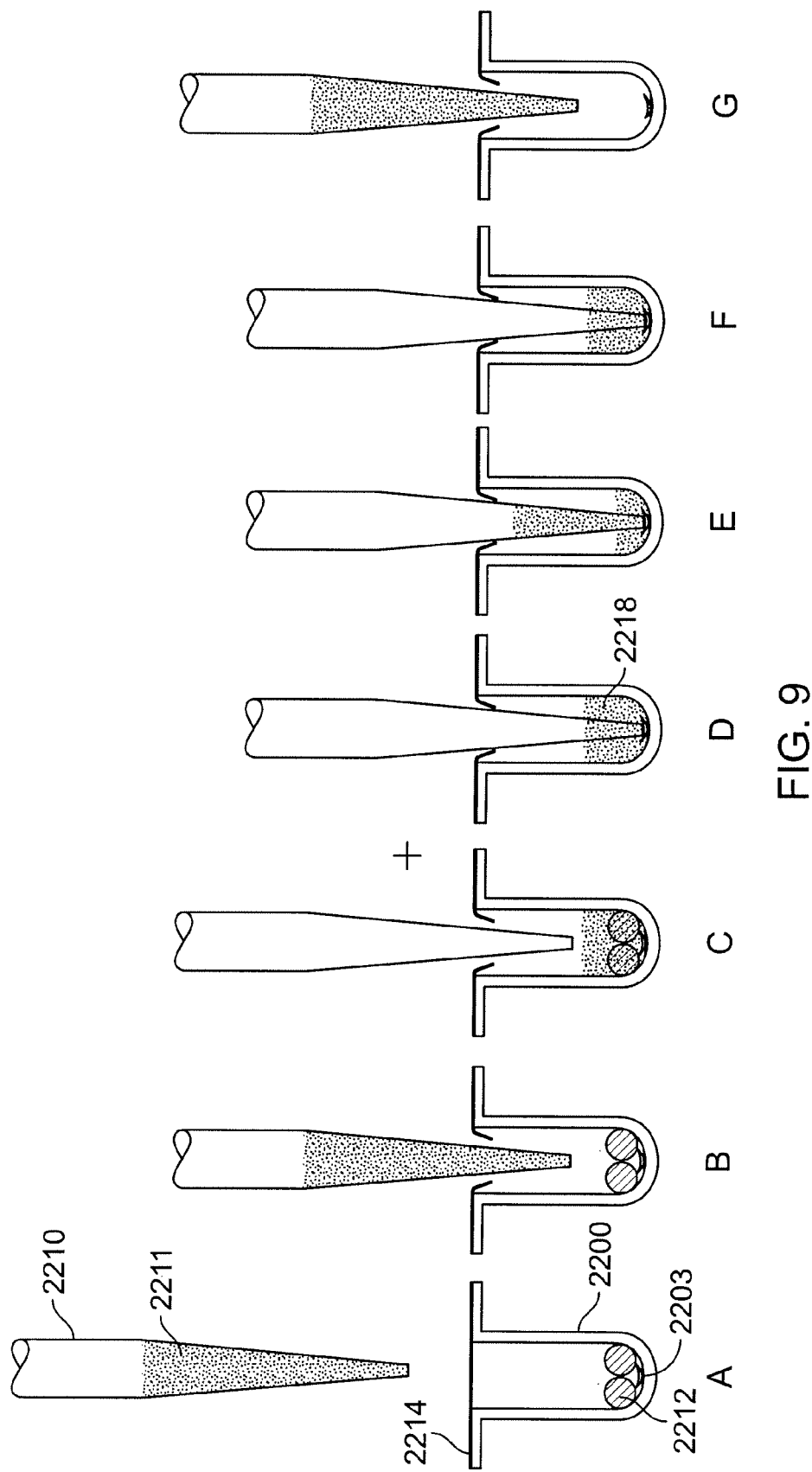
FIG. 9 shows a sequence of pipetting operations in conjunction with a reagent tube.

Basic pipetting operations, such as may be accomplished with the automated pipetting apparatus described herein, are now described, as follows. FIG. 9 has a number of panels, A-G, each representing, in sequence, a stage in an exemplary pipetting operation, such as may be carried out with a pipette head as described further herein and a process tube, as described elsewhere herein. At A, a pipette tip 2210, containing a liquid 2211 (such as a buffer solution), is positioned directly or approximately above the center of reagent tube 2200. The tube contains a number of lyophilized pellets 2212, and is sealed by a layer 2214, such as of foil. The foil may be heat-sealed on to the top of the tube. Although a laminate layer, as further described herein, can be placed on the reagent tube, typically a layer of aluminum foil is adequate, where the tube contents are solid, e.g., lyophilized, reagents. In some embodiments, the top of the reagent tube has chamfer edges to reduce expansion of the top rim of the tube during heat sealing of a foil on the top of the tube.

In various embodiments, preparation of a PCR-ready sample for use in subsequent diagnosis using the apparatus as further described herein, can include one or more of the following steps: contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid); in some embodiments, the PCR reagent mixture can be in the form of one or more lyophilized pellets, as stored in a receptacle on a holder, and the method can further include reconstituting the PCR pellet with liquid to create a PCR reagent mixture solution. Various, such as one or more, of the liquid transfer operations associated with the foregoing steps can be accomplished by one or more pipette heads on an automated pipetting apparatus that comprises a liquid dispenser, as further described herein.

Figure 10:
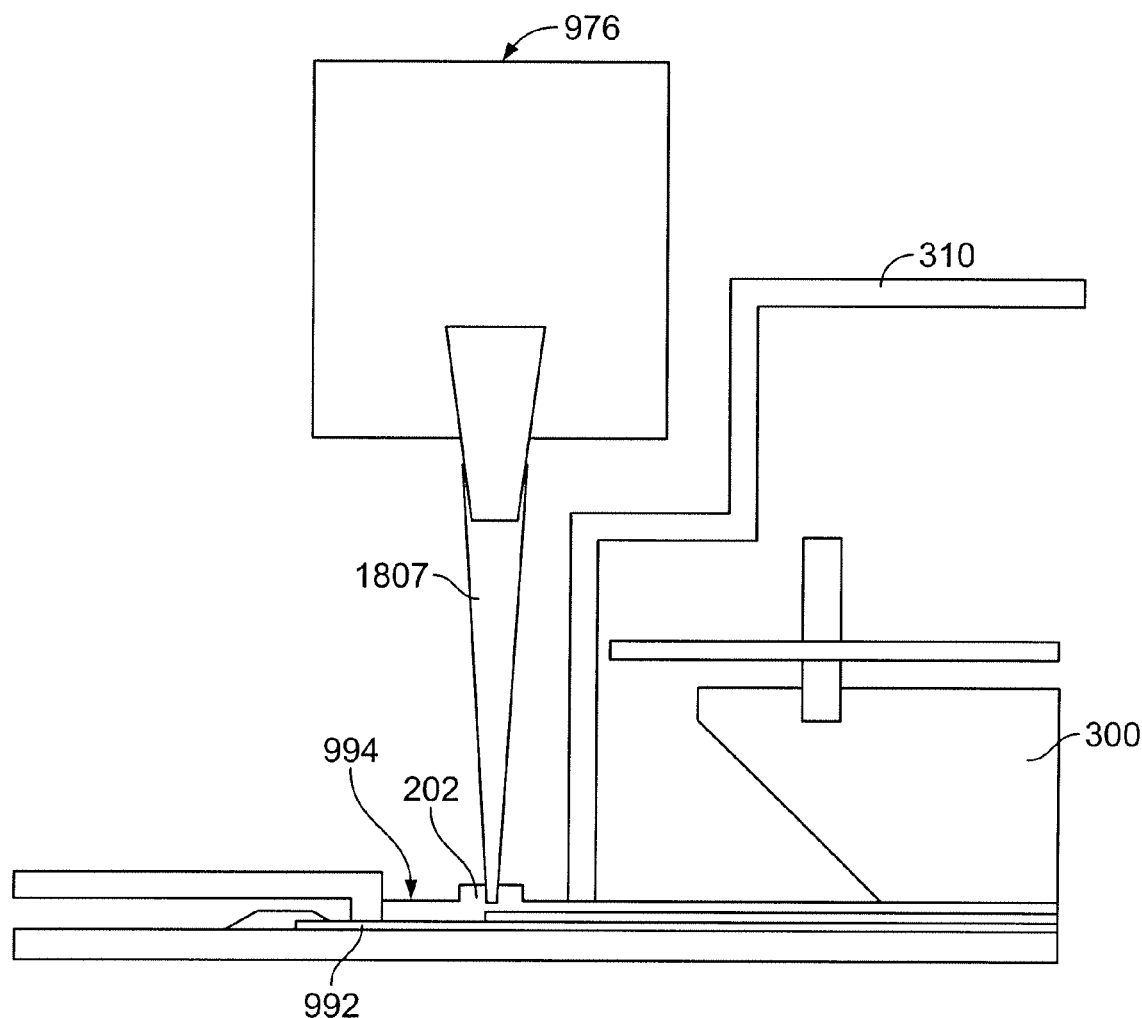
FIG. 10 shows a side schematic view of a pipette head in position to dispense liquid into a microfluidic cartridge.

The automated liquid dispenser can be further configured to dispense a solution (e.g., of a prepared sample, various PCR reagents, and detection tags) into a microfluidic cartridge. Thus, the liquid dispenser is configured to travel from a first set of positions above reagent holders having various containers that hold reagents, etc., to a second set of positions above the inlets of a microfluidic cartridge. The second set of positions is depicted schematically in FIG. 10, in side cross-sectional view. The travel of the liquid dispenser between the first set of positions and the second set of positions can be accomplished by motions in combinations of two orthogonal directions in a horizontal plane, for example, along supporting structures as further described herein, and under control of a microprocessor. Although not apparent from FIG. 10, it is consistent with the depiction that multiple, e.g., 4, pipette tips are dispensing fluid into different inlets of microfluidic cartridge 994 at any time. Liquid dispenser 976 has attached a pipette tip 1807 that is positioned so that its tip is inserted into an inlet 202 of a microfluidic cartridge 994. The cartridge is situated in a receiving bay 992. An optional cover 310 is configured to shut out ambient light from the remainder of cartridge 994, where, e.g., a target polynucleotide is detected after PCR, so that detector 300 can be as effective as possible. Suitable detectors are described in, e.g., U.S. patent application Ser. No. 12/218,498, filed Jul. 14, 2008, and incorporated herein by reference in its entirety. Although it is to be understood that the liquid dispenser herein is typically configured for use with a microfluidic cartridge, it can equally be configured to deliver appropriate quantities of prepared polynucleotide in solution to other locations at which such polynucleotides can be amplified and detected.

Liquid Dispenser

The liquid dispenser, as further described herein, can be configured to carry out pipetting operations in parallel on samples and solutions stored in one or more holders, and in one or more sample tubes, in a rack, as described elsewhere herein. It would be understood, however, that the operation, design, and function of the liquid dispenser is not dependent upon the locations of the samples and various solutions, but that the liquid dispenser could perform similarly in connection with pipetting solutions disposed in other types of receptacles. Thus, a liquid dispenser, as described herein, is an assembly of components that together cooperate to carry out such pipetting operations on solutions. The liquid dispenser thus, typically, can pick up and drop off pipette tips as needed, as well as aspirate quantities of liquid up into, and deposit out those quantities of liquid from, such pipette tips. The motions and operation of the liquid dispenser is typically controlled by a processor such that pipetting operations can be automated.

Advantageously, the liquid dispenser can be configured so that the pumps, sensors (e.g., for pipette tip presence detection, and force sensing during pipetting), sample identification verifier, and other items, move with it, and therefore minimize the number of control lines that move across the instrument during use, and also reduces the likelihood that such control lines will become tangled during motion of the liquid dispenser, as would be the case where pipette dispense heads are the only items undergoing motion, and remain in communication with other components that are fixed at various points within a preparatory or diagnostic apparatus. In such apparatus, where only e.g., dispense heads undergo motion, the need to be able to move freely in three degrees of freedom becomes severely constrained by the need to move a number of cables independently of one another.

Advantageously, as further described herein, also, the dispenser can be configured to align pipette tips, e.g., with cartridge inlet holes, using a motorized alignment plate. Additionally, as also described elsewhere herein, the dispenser can be configured with a scanner that reads information from, e.g., a sample.

Figure 11:
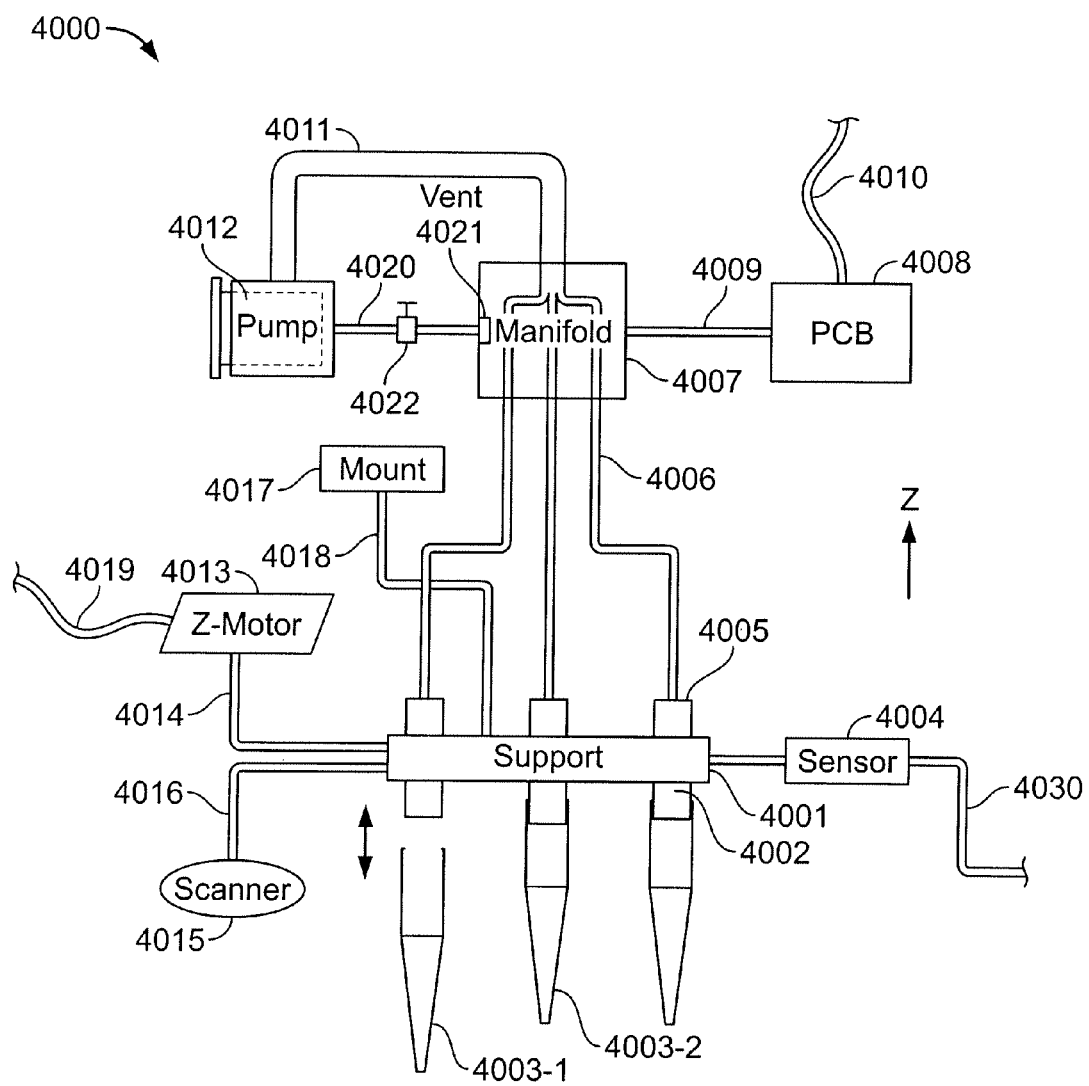
FIG. 11 shows a block diagram of a liquid dispenser, showing communication between various components thereof.

FIG. 11 shows, schematically, components of a liquid dispenser 4000 as further described herein. The layout of the components in FIG. 11 is for convenience only, and one of skill in the art would appreciate that other arrangements are possible, depending upon environment and other factors. A support 4001 has three dispense heads 4002 mounted to it. Other numbers of dispense heads, such as 1, 2, 4, 5, 6, 8, and 10, are consistent therewith. The dispense heads are configured to accept pipette tips 4003-1 (shown detached from its head), and 4003-2, shown mounted on the head. The support 4001 is movably attached via a connecting member to a mount 4017. The relative position of the support and the mount, in the z-direction as shown, can be controlled by Z-motor 4013, which is electrically coupled via connection 4014 to the support 4001. Z-motor receives instructions from a processor (not shown) via a connection 4019. In the embodiment shown, Z-motor is able to control the relative position of support 4001 and mount 4017 by moving support 4001. In other embodiments, Z-motor 4013 is coupled to mount 4017 and achieves similar relative motion of mount and support. Such relative motion can be accomplished by any suitable mechanical movement device, such as gearing, or a rack and pinion assembly, or a lead screw, the details of which are not shown in FIG. 11.

Also included within the liquid dispenser 4000 is a sensor 4004 configured to sense when vertical motion of the support or mount is obstructed, and to provide a suitable signal, e.g., via an electrical connection 4020, directly to a processor (not shown), or indirectly (not shown) via printed circuit board 4008. Thus sensor 4004 can be mounted on support 4001, as shown, or on mount 4017, depending on matters of design choice.

Optionally included within the liquid dispenser 4000 is a scanner 4015, connected to, e.g., support 4001 (or, alternatively, to mount 4017) via a connector, such as a mechanical attachment, 4016. Scanner 4015 can be configured to read, e.g., sample and patient information, from one or more of a sample tube, reagent holder, or microfluidic cartridge, as further described elsewhere herein. Scanner 4015 can be electrically connected directly (not shown) to a processor, or indirectly via printed circuit board 4008.

A valve 4005 is associated with each dispense head 4002, and serve to control operation of each dispense head such as by, for example, controlling when to reduce pressure, thereby causing a sucking operation, or to increase pressure, thereby causing a dispense operation. Each valve 4005 is connected to (including being in fluid communication with) manifold 4007 via a connecting tube 4006.

Manifold 4007 is connected to pump 4012 via an air-line 4011, and to valves 4005 via connecting tubes 4006. Manifold 4007 contains a number of independently controllable valves that selectably divert air from pump 4012 to various of valves 4005, and therefore to corresponding dispense heads 4002. In FIG. 11, a way to accomplish this is shown schematically: line 4011 is split into three separate lines each of which connects to one of lines 4006. In embodiments that service different numbers of dispense heads, such as 4 heads, line 4011 is similarly split into 4 corresponding lines.

Manifold 4007 is also typically connected to pump 4012 via a second line 4020 that is configured to permit equilibriation of air between manifold and pump. Line 4020 connects to a vent 4021 on the manifold, and is also controlled by a valve 4022.

Operation of manifold 4007 is typically controlled by printed circuit board (PCB) 4008 to which it is connected via an electrical connection 4009. PCB 4008 additionally can receive electrical input from connection 4010. Thus, the suck and dispense operations can be precisely controlled, by signals from the PCB, so that accurate volumetric control is achieved. In some embodiments, calibration of the liquid dispenser is required so that the amount of time to force or to suck air that is required to dispense or aspirate a desired volume of liquid is known. Thus, the time between, e.g., a valve opening and valve closing, as controlled by signals, is known and can be incorporated into the control software.

Pump 4012 typically also comprises a motor (not shown) controlling its action, e.g., motion of a plunger, which receives electrical signals as input, and an air supply (not shown).

FIGS. 12-21 (inclusive) show various views of an exemplary liquid dispenser, now various components of which are further described herein. It would be understood by one of ordinary skill in the art that such components, their relative configuration, number, and orientation, are exemplary, and that the degrees of freedom of motion, and accuracy of positioning and dispensing, consistent with the description herein may be achieved by other such configurations. For example, where one or more mounts are shown, other embodiments may have different numbers of mounts.

Figure 12:
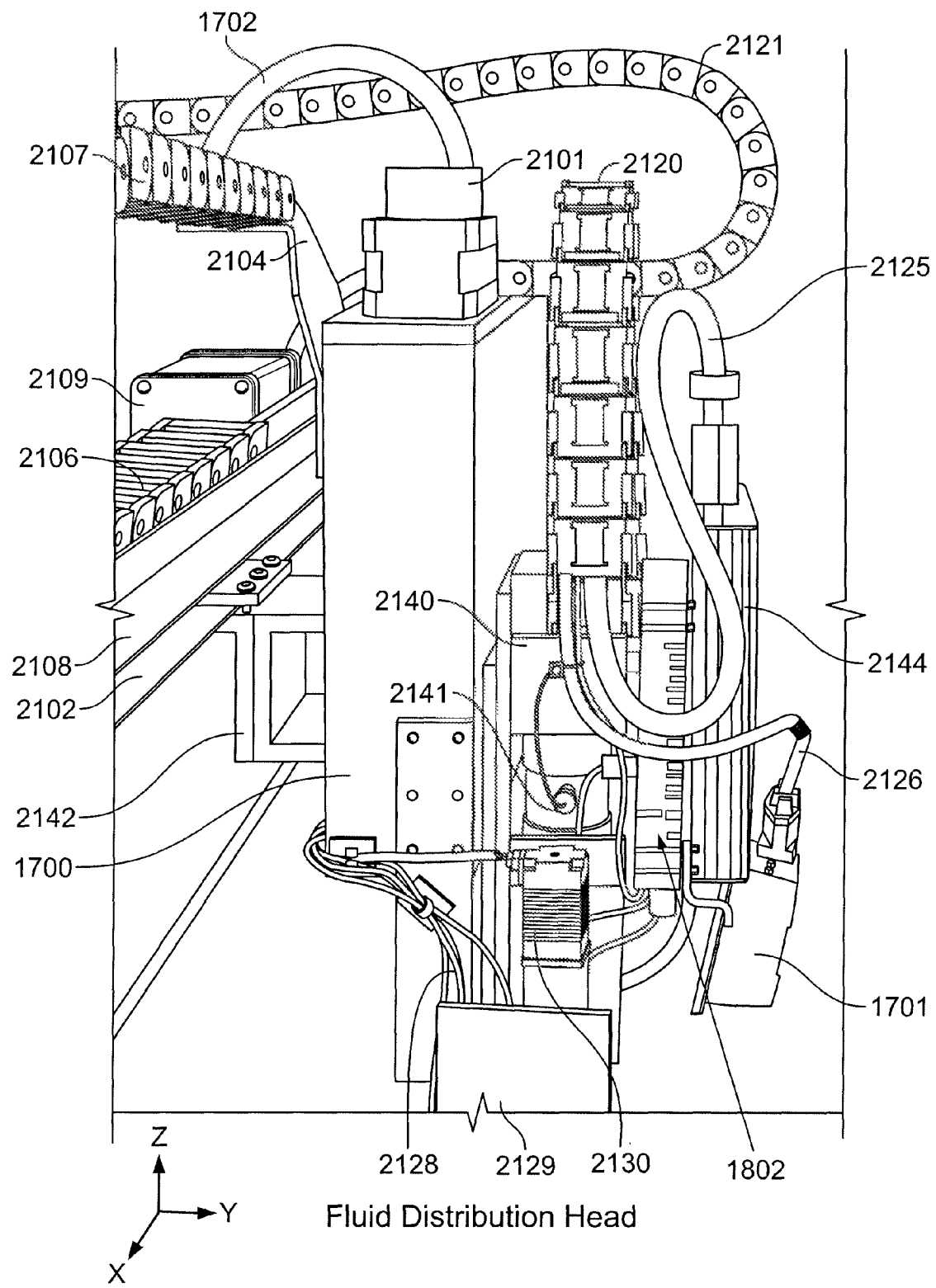
FIG. 12 shows a liquid dispense head.

A perspective side view of an exemplary liquid dispense head is shown in FIG. 12. The following items relate to control of movement of the liquid dispenser, and the housing of the liquid dispenser, are visible. Control belts 2120 and 2121 house electrical cables, are disposed orthogonally to one another, and permit motion of the liquid dispenser in two orthogonal directions: in a horizontal and a vertical plane. Control belts 2106 and 2107 hold further electrical cables, and are disposed to permit motion in a horizontal plane, orthogonal to belt 2121. Belts 2106, 2107, 2120, and 2121 permit easy motion of the liquid dispenser without entangling various electrical cables because the belts guide and house the cables while the dispenser is in motion. Electrical cable 2125 supplies control signals to assembly 2144, which houses electrical circuitry to control operation of manifold 1802 and a pump 2141 of the liquid dispenser. Manifold 1802, attached to pipette heads and other items as described herein, is thereby capable of moving up and down (z-axis), as well as in two horizontal directions. Electrical cable 1702 supplies control signals to assembly 2101, which is coupled to a motor for accomplishing vertical motion, and thereby permits such motion to be controlled. Assembly 1700 is a housing that holds the motor and the sliding head and is attached to one or more mounting plates 2104, 2142, which at least one of which is attached to a gantry 2108. A mounting assembly 2140 connects the liquid dispenser to the assembly 1700 that controls vertical motion. Mounting assembly 2140 can further comprise an air displacement/plunger pump for directing air to the dispense head. A further mounting 2129 serves as a shield for the pipette dispense heads.

The gantry 2108 comprises a horizontal rail 2102 to provide movement in the x-direction, controlled by controller 2109, which receives electrical input from cables (not shown). Also not shown is an orthogonally disposed rail to provide movement in the y-direction of the rail and the attached assemblies. The gantry permits, overall, three degrees of translational freedom of the liquid dispenser. (Further embodiments, not herein described, can comprise a gantry having fewer than three degrees of translational freedom.) A suitable gantry comprises three axes of belt-driven slides actuated by encoded stepper motors. The gantry slides can be mounted on a framework of structural angle aluminum or other equivalent material, particularly a metal or metal alloy. Slides aligned in x- and y-directions (directed out of and in the plane of FIG. 12 respectively) facilitate motion of the dispenser across an array of holders, and in a direction along a given holder, respectively. The z-axis of the gantry can be associated with a variable force sensor which can be configured to control the extent of vertical motion of the head during tip pick-up and fluid dispensing operations, as further described herein.

Assembly 1700 is shown only as an outer housing; internal parts are further shown in FIGS. 13A and 13B. A manifold 1802 is attached to an assembly 2140; the manifold controls suck and dispense operations performed by multiple pipette heads (not shown in FIG. 12). Assembly 2140 can undergo vertical movement, under suitable control, and is also further illustrated in FIGS. 13A and 13B. A detector 1701 is mounted indirectly to assembly 2140 and therefore can also move in a vertical direction. Detector 1701 typically permits positive detection of sample tubes, reagent disposables, and microfluidic cartridges. Electrical cable 2126 provides control signals to detector such as a scanner, or read-head 1701. A motor 2130 is a positioned to control motion of a stripper plate for stripping pipette tips, as further described herein. Electrical control of stripper motor 2130 can be provided by various electrical cables such as 2128 as shown in FIG. 12.

As shown in the various figures, the entire liquid dispenser that moves up and down the z-axis is a self-contained unit having only electrical connections to a processor or controller, and mechanical connections to the gantry. The translational motions in three dimensions of the liquid dispenser can be controlled by a microprocessor, such as processor 980. No fluid handling lines are associated with the dispenser. This design enables simplification of assembly of the instrument, minimizes contamination of the instrument and cross-contamination of samples between different instances of operation of the apparatus, increases efficiency of pumping (minimal dead volume) and enables easy maintenance and repair of the device. This arrangement also enables easy upgrading of features in the dispensing device, such as individual and independent pump control for each dispenser, individual pipette attachment or removal, ability to control the pitch of the pipettes, etc.

A suitable liquid dispenser for use with the apparatus herein comprises: one or more sensors (such as for sensing pipette tips, in FIGS. 17A-17C, and as further described herein); a manifold 1802; one or more pumps 2141 in fluid communication with the manifold; one or more dispense heads 1803 in fluid communication with the manifold; and electrical connections that accept electrical signals from an external controller, wherein the liquid dispenser has no inlet or outlet for fluids, other than through the one or more pumps. As described elsewhere herein, the liquid dispenser can be configured to carry out fluid transfer operations on two or more holders simultaneously, such as when operating under instructions received from one or more electrical controllers. Other sensors incorporated into the apparatus include: a sensor to sense when a pipette tip reaches the bottom of a sample tube (also called an encoder/stall sensor, as further described herein); and sensors that restrict motion of the stripper plate so that it moves back and forth between two limit switches.

A cross-sectional view of the exemplary liquid dispenser of FIG. 12 is shown in FIGS. 13A and 13B. FIG. 13B shows in close-up a portion (dashed-line box) of FIG. 13A. (Various items visible in FIG. 12, such as control cables, are omitted from FIGS. 13A and 13B, for clarity.) Liquid dispenser 2100, and ancillary items shown in FIGS. 13A and 13B, are mounted on a gantry (not shown) via a support 2104. The manner of mounting can be by a supporting member 2110, such as a plate, to which the dispenser is attached via a mechanical fastening such as one or more screws 2111. In the embodiment of FIG. 13A, a lead screw 2112 (shown in cross-section) couples the z-motor with the whole z-head and provides a mechanism that permits the z-head to move up and down vertically.

Typically, dispense heads 1803 are individually sprung. Shown in FIGS. 13A, 13B, for example, a dispense head 1803 can be mounted such that a force acting upwardly against the head, such as created when a pipette tip attached to the head meets the bottom of a container from which liquid is being sucked, can be sensed through a relative motion between the head and a force sensor. For example, when a tip attached to dispense head 1803 forces against a disposable holder in a rack below it, an upward force is transmitted causing head 1803 to torque around pivot point 2122, causing set screw 2124 to press against a force sensor. In turn, the force sensor is in communication with a processor or controller on PC board 2120 that controls at least the vertical motion of the liquid dispenser so that, thereby, the processor or controller can send instructions to arrest the vertical motion of the liquid dispenser upon receiving an appropriate signal from the force sensor. An exemplary force sensor suitable for use herein is available from Honeywell. The force sensor mechanism shown in FIGS. 13A and 13B is exemplary and one of many possible mechanisms capable of commanding the head during up pick-up and fluid dispensing operations. For example, as an alternative to a force sensor, a stall sensor that senses interruption in vertical motion of the one or more dispense heads upon contact with a sample tube or reagent holder may be used. In some embodiments, the stall sensing is performed by the encoder of the z-motor. The encoder is a sensor attached to the motor and it senses any angular steps performed by the motor. During stalling of the z-head, the encoder senses that the motor has stopped moving even though the motor was instructed to go beyond the position at which it stalled. Accordingly, as would be understood by one of ordinary skill in the art, the upward motion of the liquid dispenser as described herein is not limited to the specific mechanism shown in FIGS. 13A and 13B. A length of tubing 2131 is attached between the fluidic manifold 1802 and each of the pipette attachment nozzles.

Figures 14C, 15:
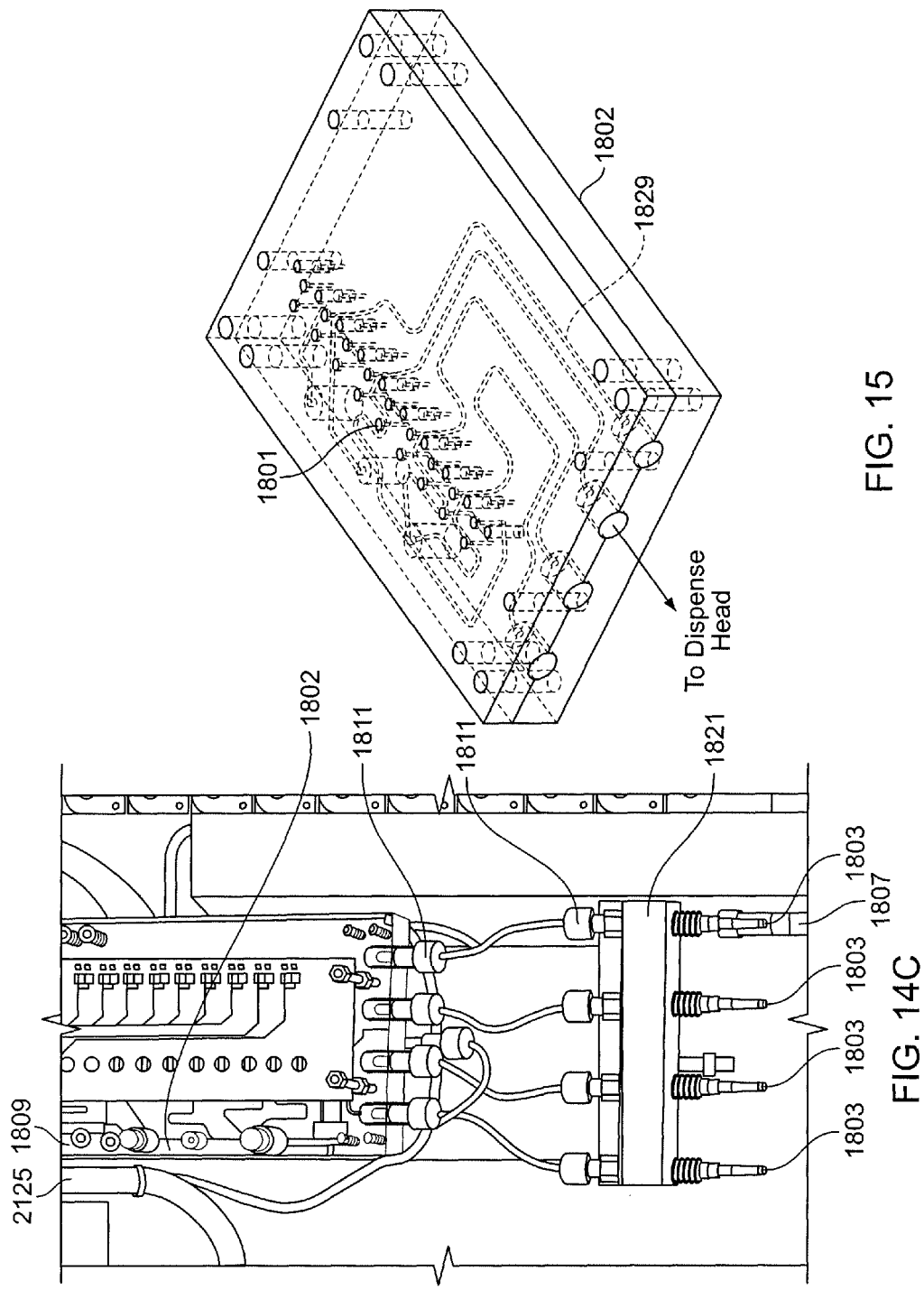

FIGS. 14A-14C show an exemplary liquid dispenser in close-up, in perspective (FIG. 14A), side (FIG. 14B, enlarged to show a portion of what is visible in the view of FIG. 14A), and front (FIG. 14C) views. The liquid dispenser comprises a number of individually sprung dispense heads 1803, wherein each head is configured to accept a pipette tip, such as from the one or more pipette tips in a holder as elsewhere described herein. Thus the spacing of the heads is calculated to be the same as the spacing of the holders in a rack, as further described herein. The rightmost head is shown with a pipette tip 1807 attached to it, visible in FIGS. 14A and 14C. The liquid dispenser can be further configured such that no two heads accept pipette tips from the same holder. The liquid dispenser can be used with, or be adapted to be used with pipette tips that have volumes as small as 10 µl to as large as 1 ml.

FIGS. 14A-C depict, for example, a "4- up" automated pipetting apparatus having four individually sprung dispense heads 1803, but it is to be understood that the dispenser is not limited to this number. For example, other numbers include 2, 3, 5, 6, 8, 10, or 12. Furthermore, the individually sprung dispense heads 1803 are shown arranged in a line in FIG. 14A, but may be configured in other arrangements, such as an array, or a circle.

The liquid dispenser can further comprise computer-controlled, motorized, pump 1800 connected to distribution manifold 1802 with related computer-controlled valving. The distribution manifold typically travels with the dispense head, rather than being positioned at a fixed location away from the dispense head while the dispense head moves from one pipetting location to another. Computer-control can be accomplished via a control board 1809, shown in the embodiment of FIGS. 14A-14C mounted on the front of the liquid dispenser. It would be understood that, in other embodiments, the control board could be mounted elsewhere, including at locations other than on the liquid dispenser if it is desired to run electric cables to the dispenser.

Also shown in FIGS. 14A-14C are a number of connectors 1811 for tubing that extends from the pump to the fluidic manifold. A mechanical structure 1821 maintains the four pipette nozzles at a fixed distance and location relative to the z-head.

The liquid dispenser is typically configured to aspirate or dispense fluid in connection with analysis or preparation of solutions of two or more samples. However, that is not to say that any of the features described herein could not also be applied in a device that operates on a single sample. The liquid dispenser is also configured to dispense liquid into a microfluidic cartridge. Typically, the liquid dispenser is configured to accept or dispense, in a single operation, an amount of 1.0 ml of fluid or less, such as an amount of fluid in the range 10 nl-1 ml.

The liquid dispenser is configured such that pump 1800 pumps air in and out of the distribution manifold. The pump can have an air supply and can be as simple in construction as having a plunger that moves back and forward compresses/expands air volume, under control of a motor, whose operation is in turn controlled by electrical signals from a processor. Air can be supplied to pump 1800 and is typically under pressure, such as at 0.1-10 psi. Thus the air supply may ultimately be provided by a compressed air cylinder, located outside of the apparatus. Typically the pump communicates with the manifold via two airways. A first airway, directs pressurized air from the pump to the manifold. A second airway can be for the purpose of equilibriating, where required, between various pipette operations, and connects with a vent on the manifold. When the pump draws air in, it is typical to close off the vents and valves in the manifold.

Further shown in FIG. 14A is a vent 1819, usually equipped with a filter (so that any airborne particles are trapped). Vent 1819 is usually closed unless it is necessary to prime the pump (such as when equilibriating the airways).

Fluid distribution manifold 1802, of which an exemplary embodiment is shown in FIG. 13, can comprise a number of valves, such as solenoid valves 1801, as are available from, e.g., the Lee Co., configured to control the flow of air through the pipette tips. Construction and design of such a manifold is within the capability of one skilled in the art. In an exemplary embodiment, there are two valves for each pipette, and one additional valve to vent the pump. Thus, for a liquid dispenser having four pipette heads, there are nine valves. In another embodiment there is only one valve for each pipette, and one additional valve to vent the pump. However, the distribution manifold is not limited to comprising exactly nine or exactly five solenoid valves.

The distribution manifold comprises a microfluidic network 1829 that distributes air evenly amongst the one or more valves that individually regulate air flow to the dispense heads. Thus, by controlling flow of air through the manifold and various valves, pressure above the pipette heads 1803 can be varied so that liquid is drawn up into or expelled from a pipette tip attached to the respective pipette heads. In this way it is not necessary to supply compressed air via an air hose to the liquid dispenser. Neither is it necessary to provide liquid lines to the dispense head. Furthermore, no liquid reagents or liquid samples from the holders enter any part of the liquid dispenser, including the manifold. The volume of liquid drawn into the pipette is less than the maximum volume of the pipette, and therefore overflows are avoided. This aspect reduces complications that would arise if air bubbles are introduced into samples or liquid reagents. An exemplary configuration of a microfluidic network in a distribution manifold is shown in dashed lines in FIG. 15. A microfluidic network is advantageous because it is lightweight and compact, and easy to manufacture.

Pipette Tip Stripper

The liquid dispenser can also operate in conjunction with a motorized plate configured to strip the pipettes and align the pipettes during dispensing of fluid from multiple pipette tips simultaneously, e.g., into a microfluidic cartridge, as further described herein. Such a device is found to be important because the tolerances for incorrect positioning of a pipette tip are very fine.

Figures 16A, 16B:
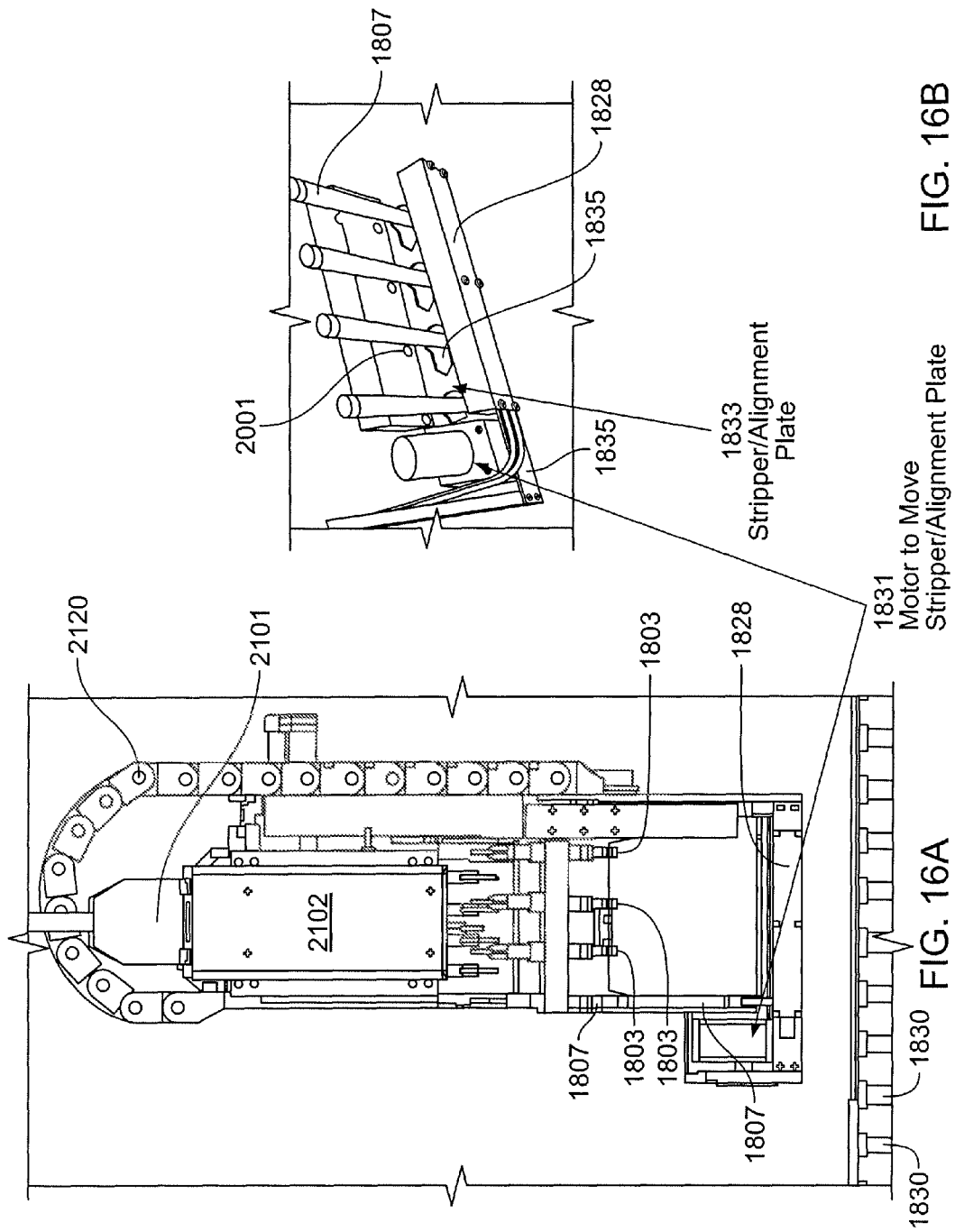
FIGS. 16A and 16B show an exemplary device for stripping pipette tips.

FIGS. 16A and 16B show operation of an exemplary device for stripping pipette tips from a liquid dispenser as further described herein. FIG. 16A is a front plan view of an embodiment of a dispense head, mounted on a gantry, as also shown in FIG. 12. A structure 1828 that holds 4 infra-red detectors for pipette sensing is shown. On the opposite side of structure 1828 (not shown) there are a number of infra-red LED's that send infra-red light towards the infra-red detectors. Typically the number of such LED's is the same as the number of detectors, in this case four. In the presence of pipette tips, an infra-red detector sees a loss of infra-red signal intensity. Also shown in FIG. 16A are sample tubes 1830, configured to accept pipette tips during various pipetting operations.

FIG. 16B shows a perspective view of a pipette stripper. The pipette tips 1807 are aligned, all at the same pitch, above respective sockets (e.g., over a pipette tip sheath) in a holder. A metal plate 1833 having one elongated hole 1835 per pipette tip lies over the sockets. Metal plate 1833 serves to play both alignment and stripping roles. Hole 1835 is configured so that it is wide enough to accommodate a pipette tip, but also has an angled elongated portion that can grip a pipette tip. Electrical connections 1839 to motor 1831, that controls sideways movement of plate 1833, are shown.

Figure 17A:
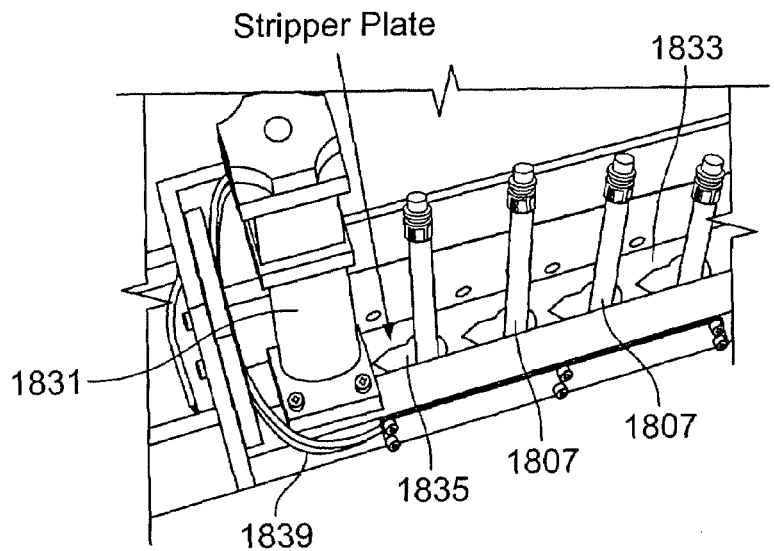
FIGS. 17A-17C show three positions of a stripper/alignment plate during operation of a pipette tip stripper.
Figure 17B:
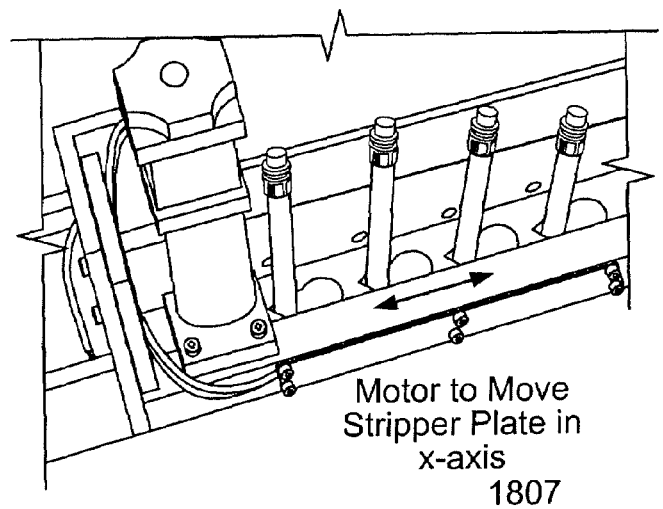

In a stripping role, as illustrated in FIGS. 17A-17B, the pipette tips (attached to the dispense head) are inserted part way down into the sheath through the elongated holes, for example under control of the liquid dispenser herein, and the metal plate is moved sideways, such as under control of a motor 1831, in such a manner that the pipette tips are clamped by the elongated portion of the holes. When the liquid dispenser is moved up, the pipette tips become detached from their respective heads. When the metal plate is subsequently moved back to its initial position, the pipette tips remain in place in their respective sockets.

Figure 17C:
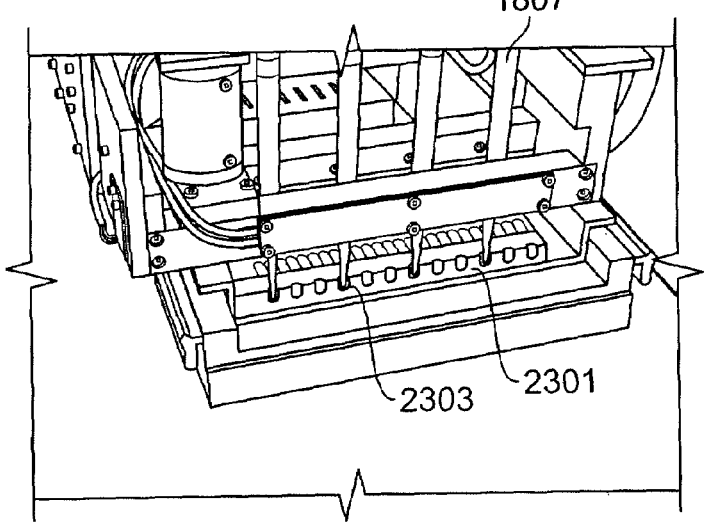

In an aligning role, shown in FIGS. 17A-17B, similar operations are performed except that the metal plate is moved sideways sufficiently to contact each pipette tip but not so far as to clamp any tip. The motion of the plate is such that the tips become aligned with respect to one another. FIG. 17C shows an outcome of aligning four pipette tips; the tips are positioned over four respective inlets 2303 of a microfluidic cartridge 2301, so that liquid can be loaded into the cartridge by interfacing the pipette tips with dedicated inlet holes, such as conical inlet holes, on the cartridge.

In certain embodiments, the liquid dispenser can also comprise one or more sensors 2001 (e.g., infra-red sensors) each of which detects the presence of a pipette tip 2005 in position beneath the dispense heads, such as in one or more holders in a rack as further described herein. This is important to ensure that the processor knows affirmatively that a pipette tip is present or missing. Since a pipette tip is picked up by application of mechanical force of a head against the pipette, and is also dispensed using mechanical motion of a stripper plate, sensing a pipette tip helps prevent mechanical errors such as having a head descend too far and become damaged. The embodiment in FIG. 18 shows 4 infrared sensors 2001 for detecting the presence of pipettes attached to the 4 pipette heads.

Such sensors can be mounted in close proximity to the pipette tip stripper described elsewhere herein. In FIG. 18, for example, an infra-red sensor 2001 can have an infra-red emitter 2003 (not shown, but on the reverse side of plate 2000) placed opposed to it, so that the presence of disposable pipette tip 1807 obstructs the line of sight between the emitter and the detector, thus enabling determination of the presence or absence of the pipette tip. The disposal pipettes are configured perpendicular to pipette stripper-alignment plate 1833 as further described herein.

Figure 18:
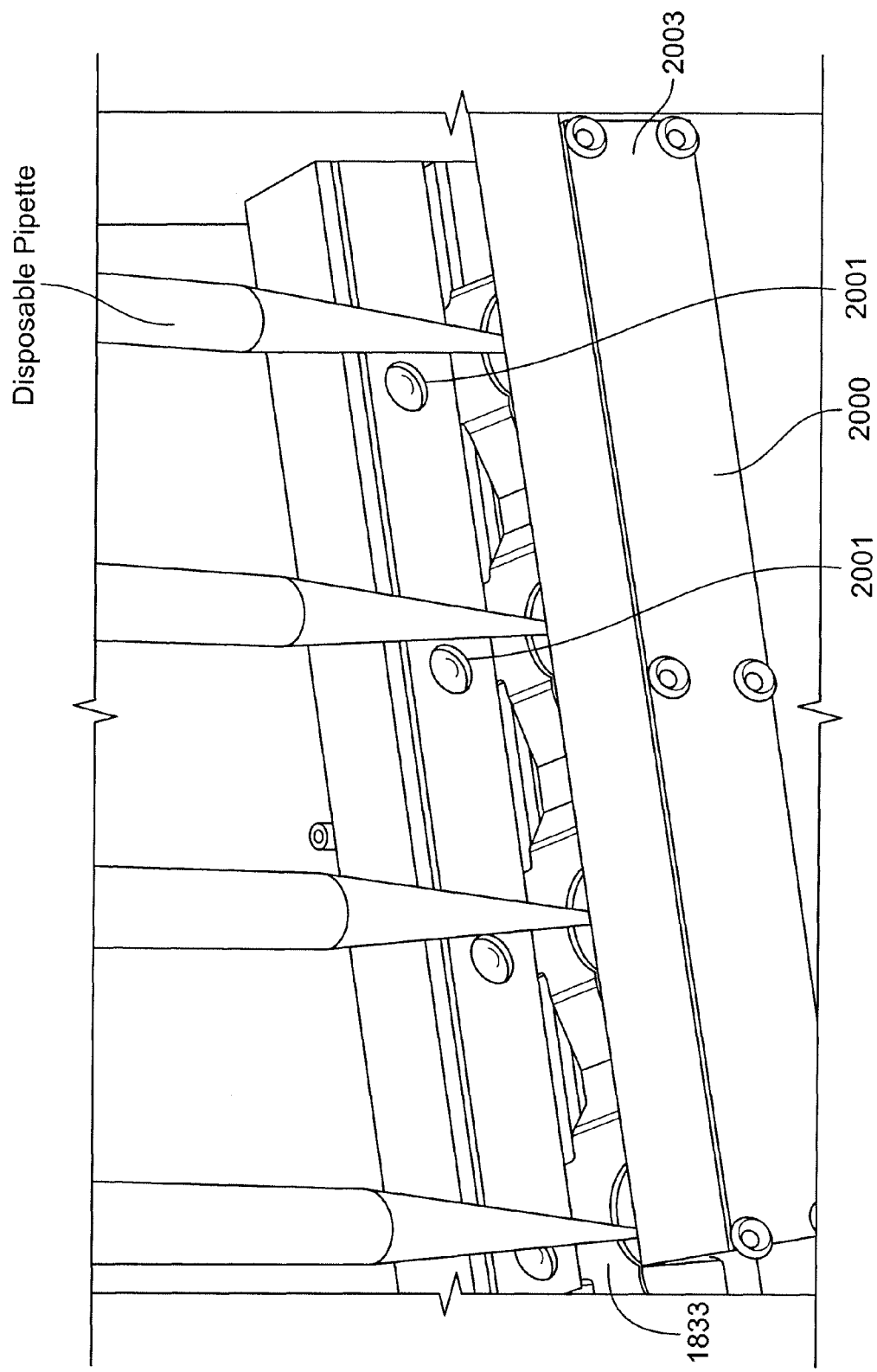
FIG. 18 shows a pipette tip stripper, and pipette tip sensors.

The embodiment shown in FIG. 18 has a stripper/alignment plate 1833 that is not flat but undulating. In other embodiments, the stripper plate can be flat, grooved, or have other shapes, such as having a wedge-shaped cross-section.

Sample Identification Verifier

Another aspect of the apparatus relates to a sample identification verifier configured to check the identity of each of the number of samples, and typically mounted on one face of the liquid dispenser, the face and location on the face being determined by other geometric features of the apparatus and its various components, as may be routinely optimized by those of skill in the art. Such sample identification verifiers can be optical character readers, bar code readers, or radio frequency tag readers, or other suitable readers, as available to one of ordinary skill in the art. A sample identification verifier can be mounted on the gantry to which the liquid dispenser is mounted, or attached to the liquid dispenser so that it moves in concert with the liquid dispenser. Alternatively, the sample identification verifier can be separately mounted and can move independently of the liquid dispenser.

Figure 19:
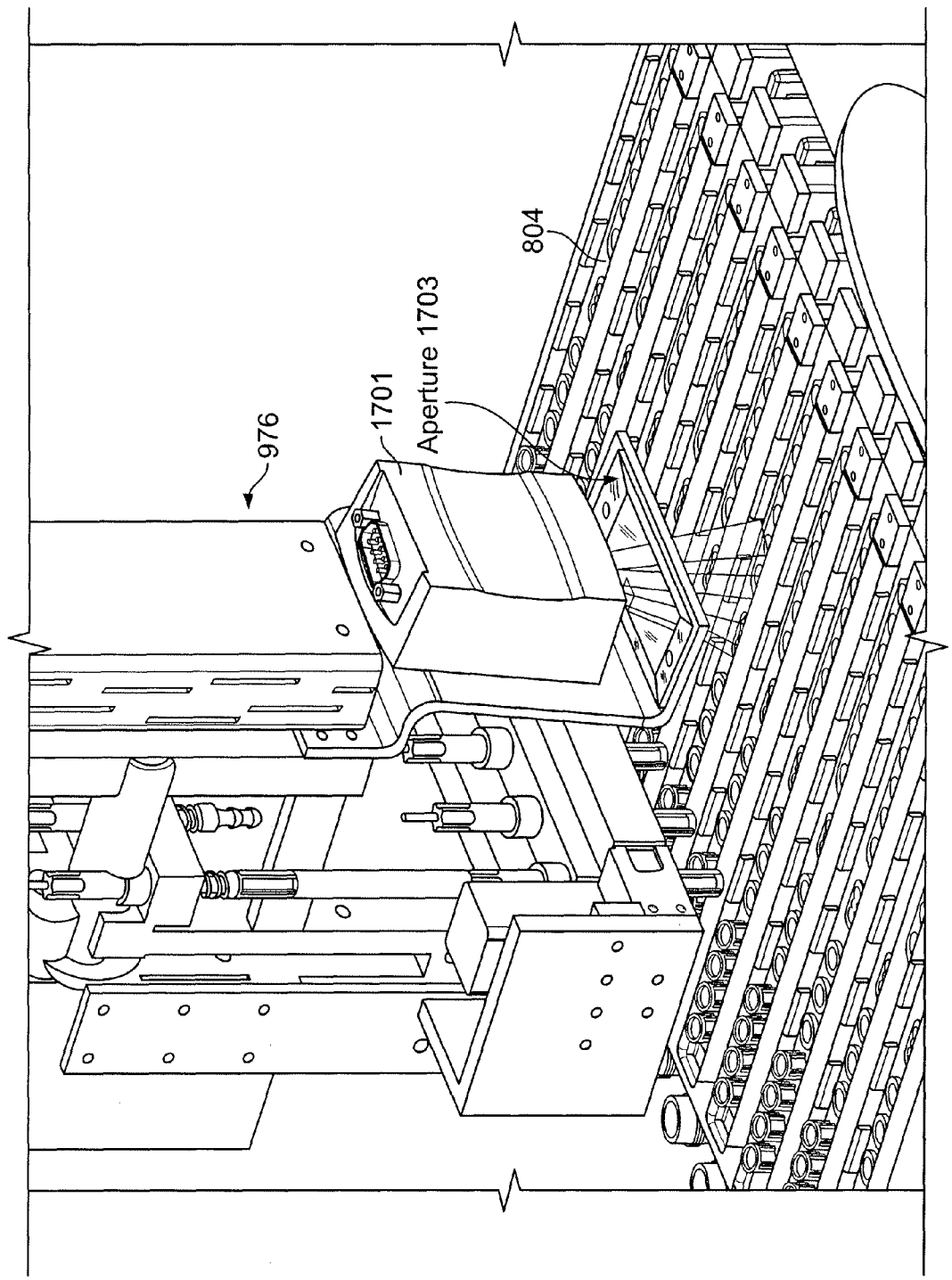
FIG. 19 shows a scanning read-head attached to a liquid dispense head, positioned over a number of reagent holders.
Figure 20:
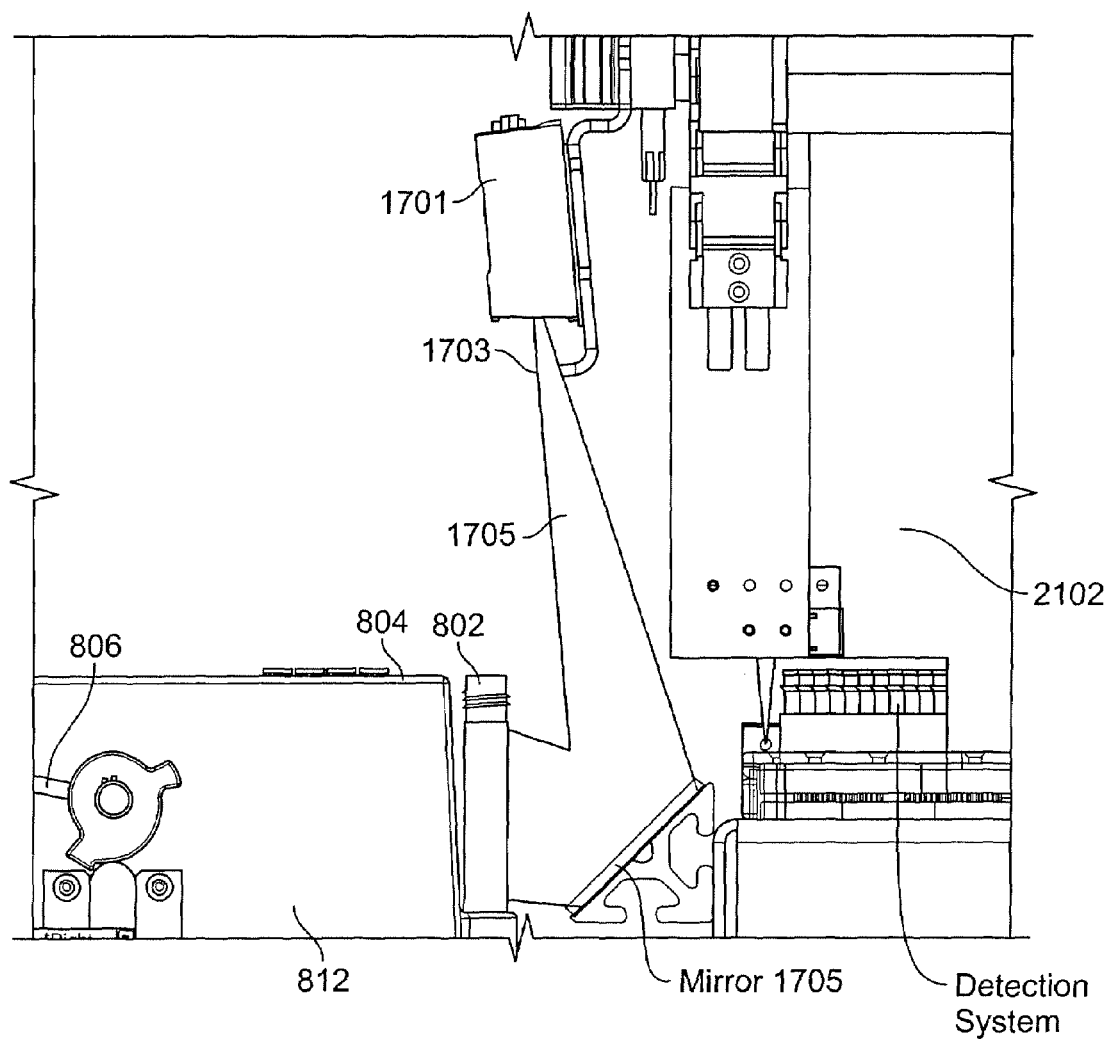
FIG. 20 shows a scanner in side view, positioned to read identifiers on one or more sample tubes.

In FIGS. 19 and 20, for example, sample identification verifier 1701 is a bar-code reader attached to the liquid dispenser. In FIG. 19, the dispense head is positioned over several reagent holders 804, mounted in a rack in a diagnostic apparatus. The sample identification verifier is similarly positioned, such that it can read labels situated on the tops of the various holders 804. Aperture 1703 determines the field of view of the verifier.

In the view of FIG. 20, the verifier is positioned to read identifying marks on sample tubes 802. The field of view 1705 of barcode scanner 1701 is non-linear, enabling it to detect light reflected by mirror 1705 from, e.g., a the barcoded clinical sample tube 802, in disposable rack 812. The barcode scanner reads the barcode on the clinical sample tube thus identifying the presence and specifics of the sample tube. Because of use of a mirror, the scanner is configured either to read a bar-code, or a 2-D barcode, printed in mirror image form (that is thus reflected into normal form by the mirror), or to read a mirror image of a normal bar-code and to convert the mirror image to unreflected form via a computer algorithm.

Figure 21:
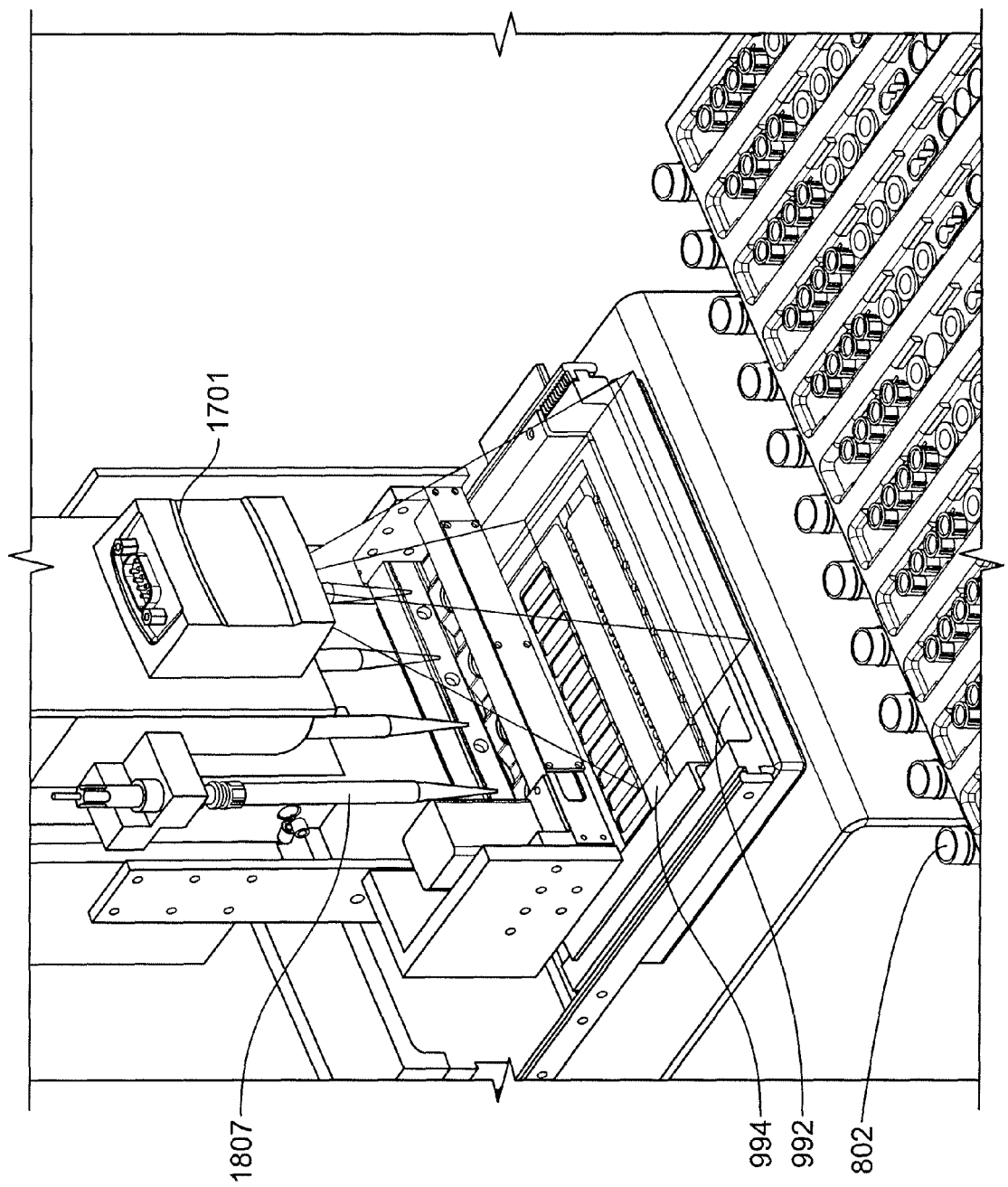
FIG. 21 shows a scanner positioned above a microfluidic cartridge.

In FIG. 21, the sample identification verifier is positioned to read indicia from a microfluidic cartridge 994, located in a receiving bay 992.

The verifier is typically mounted so that freedom of motion along the z-axis permits it to be readily positioned to read the sample tube, holder, and cartridge barcodes.

Sample identification verifier is configured to communicate details of labels that it has detected or read to a processor 980 or controller in the apparatus, thereby permitting sample identifying information to be associated with diagnostic results and other information relating to sample preparation, and extraction and amplification of nucleic acid therein.

Processor and Control

Control of automated motions of the liquid dispenser of the automated pipetting apparatus is via a suitably configured processor. The processor has been configured to execute instructions that deliver control signals to the various motors, and to receive signals from the various sensors, within the automated pipetting apparatus. Design and manufacture of such a processor is within the capability of one of ordinary skill in the art of laboratory automation systems, or apparatus control systems. The instructions executed by the processor can, similarly, be designed and implemented by one of ordinary skill in the art of computer programming. The instructions can take into account desired protocols of varying natures, depending on numbers of samples, locations of samples, and nature of target nucleotides, and cause motions of the liquid dispense head. The instructions can also take into account signals received from one or more sensors, in order to determine which of one or more next steps to execute, or whether to execute such steps at all or to instead, issue an error notification. The instructions may provide to a user a menu of pre-determined protocols to choose from and to execute, or may permit a user to design a new protocol, or modify an existing one.

Microfluidic Cartridge

As described elsewhere herein, the liquid dispenser can be configured to deliver quantities of solution containing one or more polynucleotide(s) in a form suitable for amplification to a microfluidic cartridge. Typically, such delivery occurs for multiple quantities of solution in parallel. A microfluidic cartridge compatible with such a process typically has a number of inlets, corresponding to a practical number of samples that are to be processed in parallel, for example, 2, 4, 6, 8, 10, 12, 16, or 24. Each inlet is situated in a lane of the cartridge, each lane further having channels that divert the respective samples to respective chambers within which an amplification such as PCR can be performed. The chambers typically can be isolated by one or more valves, during amplification. The chambers are also typically situated so that the progress of amplification can be monitored by one or more detectors. Exemplary configurations and manufactures of cartridges are described elsewhere, including but not limited to U.S. patent application Ser. No. 12/173,023, filed on Jul. 14, 2008, and Ser. No. 11/985,577, filed Nov. 14, 2007, both of which are incorporated herein by reference.

Typically, the inlet separation on the cartridge, or other receiving area, is chosen to correspond to the separation between adjacent pipette tips on the dispense heads of the liquid dispenser, or some convenient fraction or multiple thereof. Thus, for example, for a cartridge having an 8 mm separation between adjacent inlets, used in conjunction with a liquid dispenser having a 24 mm separation between the centers of the tips of adjacent pipette tips, the liquid dispenser can dispense samples into cartridge inlets that are separated by two inlets (e.g., a first and fourth inlets, numbering from a particular end of the cartridge). It would be understood that these dimensions and multiples are not limiting.

The apparatus having been described, it is illustrated by way of the following non-limiting examples.

EXAMPLES

Example 1

Exemplary Chemistry and Processes of Use

Chemistry Overview

The chemistry processes typically carried out with the apparatus described herein center around the detection and identification of organisms in a clinical specimen, by virtue of detecting nucleic acids from the organism in question. This involves isolation of nucleic acids from target organisms that are contained in a clinical specimen, followed by a process that will detect the presence of specific nucleic acid sequences. In addition to target detection, an internal positive control nucleic acid can be added to the collection buffer, and can thereby be taken through the entire extraction and detection process along with target nucleic acids. This control will monitor the effectiveness of the entire process and will minimize the risk of having false negative results.

Nucleic Acid Extraction and Purification

Nucleic acid extraction procedures begin with the addition of a clinical specimen to a prepared specimen collection solution. This can be done either at a specimen collection site, or at the testing site. Two collection solution formats can be available: one for body fluids, and one for swab specimens. Collection solutions used at collection sites will serve as specimen transport solutions, and therefore, this solution must maintain specimen and analyte integrity.

The extraction and purification procedure, which is entirely automated using a liquid dispenser as described herein, in conjunction with a suitable heater and separator, proceeds as follows:

Target organisms are lysed by heating the detergent-containing collection solution.

Magnetic beads, added to the specimen/collection solution mix, non-specifically bind all DNA that is released into the solution.

Magnetic beads are isolated and are washed to eliminate contaminants

DNA is released from the beads using high pH and heat.

DNA containing solution is removed and neutralized with a buffer

Nucleic Acid Amplification

Nucleic acids that have been captured by magnetic beads, washed, released in high pH, and neutralized with buffer, are added to a mixture of buffers, salts, and enzymes that have been lyophilized in a tube. The mixture is rapidly rehydrated, and then a portion of the solution is loaded onto a microfluidic cartridge. The cartridge is then loaded into the amplification instrument module, which consists of a heating unit capable of thermal cycling, and an optical detection system. Detection of target nucleic acids proceeds as follows:

The liquid is sealed in a reaction chamber.

Rapid thermal cycling is used to potentiate the Polymerase Chain Reaction (PCR), which is used to amplify specific target DNA.

Amplified DNA fluoresces, and can be detected by optical sensors.

A fluorescent probe "tail" is incorporated into each amplified piece of DNA

At a specific temperature, the probe adopts a conformation that produces fluorescence (this is termed a "scorpion" reaction).

Fluorescence is detected and monitored throughout the reaction.

Extraction and Amplification/Detection Process

Extensive bench-scale testing has been performed to optimize the nucleic acid extraction chemistry, including the collection buffer, the wash buffer formulation, the release solution formulation, and the PCR reagent mixes. The fully automated method of extraction, followed by 12-up PCR, was able to provide very high sensitivity consistently at 150 copies/sample.

Examplary target/sample combinations include: Chlamydia in Urine (50/50); Gonrorrhoea in Urine; GBS in Plasma.

Various detection chemistries such as Taqman, Scorpion, and SYBRg Green work reliably in the microfluidic cartridge.

Example 2

Exemplary Chemistry Processes Performed by an Automated Instrument

Sample Pre-Processing

For Urine Sample: Take 0.5 ml of urine and mix it with 0.5 ml of collection buffer. Filter the sample through a pre-filter (containing two membranes of 10 micron and 3 micron pore size).

For Plasma Sample: Take 0.5 ml of plasma and mix it with 0.5 ml of collection buffer.

For GBS swab samples: Take the swab sample and dip it in 1 ml of collection buffer.

For each type of sample, after it is mixed with the appropriate collection buffer (and filtered if applicable), the solution is placed in the external sample tube in the position specified for it in the rack.

The sample collection buffer contains 50 mM Tris pH 7, 1% Triton X-100, 20 mM Citrate, 20 mM Borate, 100 mM EDTA, plus 1,000 copies of positive control DNA.

Loading the Instrument and Starting Sample Processing

The following steps may be performed to initiate an analysis on samples in batch.
1. Load PCR tube containing PCR master mix in one of the specified snap-in location of the reagent holder.
2. Load PCR tube containing PCR probes and primers for the target analyte under consideration in the specified location of the reagent holder.
3. In case of two analyte test, load PCR tube containing probes and primers for second analyte in the specified location of the reagent holder.
4. Insert the reagent holder in a rack, typically a 12-holder rack, in the same lane as the sample tube under consideration.
5. Prepare and insert reagent holders for other samples in consideration.
6. Load the rack in one of the locations in the instrument.
7. Load a cartridge in the cartridge tray loading position. Typically the cartridge has the same number of lanes as the rack; thus a 12-sample cartridge is used in conjunction with a 12-holder rack.
8. Start operation.

Liquid Processing Steps

The following steps may be performed to carry out sample preparation. Herein the numbering of the pipette tips refers to those pipette tips that are stored in a reagent holder, for example, in a pipette sheath of such a holder. It would be understood that such operations could be performed multiply in parallel by a liquid dispenser as described elsewhere herein. References to a 'robot' herein are intended to mean an automated pipetting apparatus, such as embodiments further described herein.
1. Using Pipette tip #1, the robot transfers the clinical sample from the external sample tube to the process tube of the reagent holder.
2. Using the same pipette tip, the robot takes about 100 µl of sample, mixes the lyophilized enzyme and affinity beads, transfers the reagents to the process tube. Mixing is performed in the process tube by 5 suck and dispense operations.
3. The robot places pipette tip #1 at its designated location in the reagent holder.
4. Heat the process tube to 60° C. and maintain it for 10 minutes.

5. After 5 minute of lysis, the robot picks up pipette tip #1 and mixes the contents by 3 suck and dispense operations.
6. The robot places pipette tip #1 at its designated location in the reagent holder,
7. After 10 minutes of lysis, a magnet is moved up the side of the process tube to a middle height of the sample and held at that position for a minute to capture all the magnetic beads against the wall the tube.
8. The magnet is brought down slowly to slide the captured beads close to the bottom (but not the bottom) of the tube.
9. Using pipette tip #2, aspirate all the liquid and dump it into the waste tube.
10. Aspirate a second time to remove as much liquid as possible from the process tube.
11. Using the same pipette tip #2, withdraw 100 µl of wash buffer and dispense it in the process tube. During this dispense, the magnet is moved downwards, away from the process tube.
12. Perform 15 mix steps to thoroughly mix the magnetic beads with the wash buffer.
13. Wait for 30 seconds.
14. Move magnet up to capture the beads to the side and hold for 15 seconds.
15. Using pipette tip #2, aspirate wash buffer twice to remove as much liquid as possible and dump it back in the wash tube.
16. Move magnet down away from the process tube.
17. Place pipette tip # 2 in its specified location of the reagent holder.
18. Pick up a new pipette tip (tip #3) and withdraw 8-10 µl of release buffer and dispense it over the beads in the process tube.
19. Wait for 1 minute and then perform 45 mixes.
20. Heat the release solution to 85° C. and maintain temperature for 5 minutes.
21. Place pipette tip # 3 in its specified location of the reagent holder.
22. Bring magnet up the tube, capture all the beads against the tube wall and move it up and away from the bottom of the tube.
23. Pick up a new pipette tip (tip #4) and withdraw all the release buffer from the process tube and then withdraw 3-10 µl of neutralization buffer, mix it in the pipette tip and dispense it in the PCR tube. (In case of two analyte detections, dispense half of the neutralized DNA solution into first PCR tube and the rest of the solution in the second PCR tube.)
24. Using pipette tip #4, mix the neutralized DNA with the lyophilized reagents by 4-5 suck and dispense operations and withdraw the entire solution in the pipette tip.
25. Using pipette tip #4, load 6 µl of the final PCR solution in a lane of the 12-up cartridge.

Real-Time PCR

After all the appropriate PCR lanes of the PCR cartridge are loaded with final PCR solution, the tray containing the cartridge moves the cartridge into the PCR Analyzer. The cartridge is pressed by an optical detection read-head against the PCR heater. Heaters activate valves to close either ends of the PCR reactor and the real-time thermocycling process starts. After completing appropriate PCR cycles (~45 cycles), the analyzer decides whether the sample has the target DNA based on the output fluorescence data, and issues an indication of the same.

Example 3

Reagent Holder

An exemplary reagent holder consistent with the description herein has the following dimensions and capacities:
180 mm long×22 mm wide×100 mm tall;
Made from Polypropylene.
One snapped-in low binding 1.7 ml tube that functions as a process tube.
3 built-in tubes that function as receptacles for reagents, as follows:
  One tube containing 200-1000 µl of wash buffer (0.1 mM Tris, pH 8).
  One tube containing 200-1000 µl of release solution (40 mM NaOH).
  One tube containing 200-1000 µl of neutralization solution (330 mM Tris, pH 8.0).
One built-in tube that functions as a waste chamber (will hold ~4 ml of liquid waste).
3 receptacles to accept containers for solid reagents. Snap-in 0.3 ml or 0.65 ml PCR tubes (which are typically stored separately from the reagent holder) are placed in each of these locations, and contain, respectively:
  lyophilized sample preparation reagents (lysis enzyme mix and magnetic affinity beads).
  First lyophilized PCR master mix, probes and primers for a first target analyte detection.
  Second lyophilized PCR master mix, probes and primers for a second target analyte detection (only offered in select cases, such as detection of Chlamydia and Gonorrhea from urine).
4 pipette tips located in 4 respective sockets.
Pipette tip Sheath: The pipette tips have a sheath/drip tray underneath to help capture any drip from the pipette tips after being used, and also to prevent unwanted contamination of the instrument.
Handle and Flex-Lock allows easy insertion, removal, and positive location of strip in rack.
One or more labels: positioned upward facing to facilitate ease of reading by eye and/or, e.g., a bar-code reader, the one or more labels containing human and machine readable information pertaining to the analysis to be performed.

It is to be understood that these dimensions are exemplary. However, it is particularly desirable to ensure that a holder does not exceed these dimensions so that a rack and an apparatus that accommodates the reagent holder(s) does not become inconveniently large, and can be suitably situated in a laboratory, e.g., on a bench-top.

Example 4

Exemplary Foil-Sealing of Buffer Containing Reagent Tubes

Tubes containing buffers have to be sealed with high moisture vapor barrier materials in order to retain the liquid over a long period of time. Reagent holders may need to have a shelf life of 1-2 years, and as such, they should not lose more than say 10-15% of the liquid volume over the time period, to maintain required volume of liquid, and to maintain the concentration of various molecules present in the solution. Moreover, the materials used for construction of the tube as well as the sealing laminate should not react with the liquid buffer. Special plastic laminates may provide the moisture barrier but they may have to be very thick (more than 300 µm thick), causing the piercing force to go up tremendously, or of special, expensive polymer (such as Aclar). Aluminum foils, even a thin foil of a few hundred angstrom provides an effective moisture barrier but bare aluminum reacts with some liquid buffers, such as sodium hydroxide, even an aluminum foil with a sprayed coating of a non-reactive polymer may not be able to withstand the corrosive vapors over a long time. They may react through tiny pin holes present in the coating and may fail as a barrier over time.

For these reasons, aluminum foils with a laminate structure have been identified as a suitable barrier, exemplary properties of which are described below:
1. Sealing
   Heat seals to unitized polypropylene strip (sealing temp ~170-180° C.)
   No wrinkling, cracking and crazing of the foil after sealing
2. Moisture Vapor Transmission Rate (MVTR)
   Loss of less than 10% liquid (20 microliters from a volume of 200 microliter) for a period of 1 year stored at ambient temperature and pressure. (effective area of transport is ~63 mm$^2$); Approximate MVTR ~0.8 cc/m$^2$/day
3. Chemistry
   Ability to not react with 40 mM Sodium Hydroxide (pH<12.6): foil should have a plastic laminate at least 15 microns thick closer to the sealed fluid.
   Ability to not react with other buffers containing mild detergents
4. Puncture
   Ability to puncture using a p1000 pipette with a force less than 3 lb
   Before puncturing, a fully supported membrane 8 mm in diameter will not stretch more than 5 mm in the orthogonal direction
   After puncturing, the foil should not seal the pipette tip around the circumference of the pipette.
5. Other Features
   Pin-hole free
   No bubbles in case of multi-laminate structures.

Example 5

Illustrative Mechanism of Piercing Through a Plasticized Laminate and Withdrawing Liquid Buffer The aluminum laminate containing a plastic film described elsewhere herein serves well for not reacting with corrosive reagents such as buffers containing NaOH, and having the favorable properties of pierceability and acting as a moisture barrier. However, it presents some additional difficulties during piercing. The aluminum foil tends to burst into an irregular polygonal pattern bigger than the diameter of the pipette, whereas the plastic film tends to wrap around the pipette tip with minimal gap between the pipette and the plastic film. The diameter of the hole in the plastic film is similar to the maximum diameter of the pipette that had crossed through the laminate. This wrapping of the pipette causes difficulty in dispensing and pipetting operations unless there is a vent hole allowing pressures to equilibrate between outside of the tube and the air inside of the tube.

A strategy for successful pipetting of fluid is as follows:
1. Pierce through the laminate structure and have the pipette go close to the bottom of the reagent tube so that the hole created in the laminate is almost as big as the maximum diameter of the pipette (e.g., ~6 mm for a p1000 pipette)
2. Withdraw the pipette up a short distance so that a small annular vent hole is left between the pipette and the laminate. The p1000 pipette has a smallest outer diameter of 1 mm and maximum outer diameter of 6 mm and the conical section of the pipette is about 28 mm long. A vent hole thickness of a hundred microns is enough to create a reliable vent hole. This corresponds to the pipette inserted to a diameter of 5.8 mm, leaving an annulus of 0.1 mm around it.
3. Withdraw fluid from the tube. Note that the tube is designed to hold more fluid than is necessary to withdraw from it for a typical sample preparation procedure.

Example 6

Exemplary Foil Piercing and Dissolution of Lyophilized Reagents

The containers of lyophilized reagents provided in conjunction with a holder as described herein are typically sealed by a non-plasticized aluminum foil (i.e., not a laminate as is used to seal the reagent tubes). Aluminum foil bursts into an irregular polygonal pattern when pierced through a pipette and leaves an air vent even though the pipette is moved to the bottom of the tube. In order to save on reagents, it is desirable to dissolve the reagents and maximize the amount withdrawn from the tube. To accomplish this, a star-ridged (stellated) pattern is placed at the bottom of the container to maximize liquid volume withdrawn, and flow velocity in between the ridges.

Exemplary steps for dissolving and withdrawing fluid are as follows:
1. Pierce through the pipette and dispense the fluid away from the lyophilized material. If the pipette goes below the level of the lyophilized material, it will go into the pipette and may cause jamming of the liquid flow out of the pipette.
2. Let the lyophilized material dissolve for a few seconds.
3. Move pipette down touching the ridged-bottom of the tube. The pipette stops moving when it senses an opposition to its motion, such as by a force sensor described elsewhere herein.
4. Perform an adequate number of suck and spit operations (such as 4-10) to thoroughly mix the reagents with the liquid buffer.
5. Withdraw all the reagents and move pipette to dispense it into the next processing tube.

Example 7

Exemplary Force Sensing of the Pipette Head

Travel of the liquid dispenser along the z-axis is regulated by a force-sensor. A force sensor is interfaced with the pipette heads in such a way that any time the pipette head seats against the disposable pipette tip(s) or the picked pipettes are forced through a laminate cover of the reagent holder, or the pipette tip is forced against the bottom of the tubes in the reagent disposable, an upward force acts on the pipette head through the pipette holding nozzle or the pipette tip itself The entire head is pivoted at a lower point, and any force acting on the head causes a set-screw on the upper part of the head to press against a force sensor. This force sensor is calibrated for vertical displacement of the head against a non-moving surface. Using this calibration, it can be determined when to stop moving the head in the z-direction by detecting whether, for example, a pipette is properly seated or if a pipette tip has hit a tube bottom.

Example 8

Exemplary Alignment of Pipette Tips While Loading PCR Reagent Solutions Into a Microfluidic Cartridge The liquid dispenser is configured so that, when multiple pipette tips are attached simultaneously, the tips can dispense in parallel to multiple inlets on a microfluidic cartridge. In particular, this means that the spacing between the tips is exactly the same as, or the same as to within an acceptable tolerance, the spacing between the inlets on the cartridge. Larger volume pipette tips can be as long as 95 mm (for, e.g., a p1000 pipette). When 4 long pipette tips are sprung from the head, even a 1° misalignment during seating can cause the tip to be off-center by ~1.7 mm, which is sufficient for that tip to miss the desired inlet on the cartridge. As it is difficult to have perfect alignment all the time during pipetting of the tip both at its top where it is interfaced with the tip holder and its bottom, it becomes necessary to mechanically constrain all the tips at another location closer to the bottom. As described elsewhere herein, a stripper plate having a defined hole structure, can be used to align all the tips. The stripper plate holes clear all the 4 pipette tips when they are picked up. After the tips are properly seated, the stripper plate is moved horizontally, such as in the x-axis direction, using a motor to move all the pipettes against the notches provided in the stripper plate. Now all the pipettes land on the cartridge inlet holes with ease.

Example 9

Exemplary Apparatus Including an Automated Pipetting System

Described herein are exemplary specifications for the mechanical design of a system for carrying out PCR on multiple samples. In some embodiments, the system can be about 28.5 inches deep, or less, and about 43 inches wide, or less, and weight about 250 pounds or less. The system can be designed with a useful life of about 5 years (e.g., assuming 16,000 tests per year) and can be designed such that the sound level for this instrument (during operation) does not exceed 50 dB as measured 12 inches from the instrument in all ordinate directions. In some embodiments, the exterior of the system can be white with texture.

Referring to the overall system, in some embodiments, critical components of the system can remain orthogonal or parallel (as appropriate) to within 0.04 degrees. Exemplary critical components can include motion rails, pipettes, nozzles (e.g., axially as individual nozzles, linearly as an array of four nozzle centroids, or the like), lysis heaters, major edges of the installed cartridge holder in the reader drawer, the front face of the separation magnets, and the like.

In the following descriptions as with elsewhere herein, the X-axis (or X direction) refers to the axis extending from left to right when facing the front of the system, the Y-axis (or Y direction) refers to the axis extending from back to front when facing the front of the system, and the Z-axis (or Z direction) refers to the axis extending up from the bottom when facing the front of the system. As viewed from the top of the instrument, the centroid of the leftmost pipette nozzle on the Z-payload (as viewed from the front of the instrument) can be capable of unobstructed travel in the X direction from a point 80 mm from the outermost left baseplate edge to a point 608 mm from the outermost left baseplate edge and can be capable of unobstructed travel in the Y direction from a point 60 mm from the outermost front baseplate edge to a point 410 mm from the outermost front baseplate edge.

Still referring to the system, as viewed from the front of the instrument, the bottom-most face of the pipette nozzles on the Z-payload can be capable of unobstructed travel in the Y direction from a point 156 mm above the top surface of the baseplate to a point 256 mm above the top surface of the baseplate. The 1 ml pipette tips can be capable of penetrating the foil covers included on disposable reagent strips. This penetration may not create contamination, affect the associated chemistries, or damage the pipette tips. Motions can be executed in such a manner as to eliminate mechanical hysteresis, as needed. Gantry motions can be optimized to prevent cross lane contamination and carryover. The rack can align the reagent strips to a tolerance of +/−0.010 inches in the X and Y directions.

Referring now to the gantry, in some embodiments, the gantry can consist of a stepper-motor actuated, belt/screw-driven Cartesian robotic system. The gantry can be free to move, with or without attachments, above the modules that are forward of the rear facade and below the bottom-most horizontal face on the Z head, so long as the Z-payload is fully retracted. The gantry can be capable of travel speeds up to about 500 mm/sec in the X and Y directions and up to about 100 mm/sec in the Z direction. The accuracy and precision of the axis motions (e.g., with respect to the X, Y, and Z home sensors) can be 25 mm or better for each axis, and can be retained throughout the maintenance period. The axis drive belts may not leave residue in areas where PCR and samples are processed. The gantry can contain provisions for routing its own and all Z-payload wire harnesses back to the instrument. Belt tension on the X and Y axes can be set at 41.5+/−3.5 pounds.

Referring now to the Z-payload, the fluid head can have 4 pipette attachment nozzles located at 24 mm distances between adjacent centers. Such a distance is chosen to facilitate interfacing the pipette tips and inlets on a microfluidic cartridge, as well as between sample tubes, or reagent tubes, on adjacent holders. Exemplary pipette tips that the pipette nozzles can capture without leakage include Biorobotix tips PN23500048 (50 µL), PN23500049 (1.75 µL), and PN23500046 (1 ml). The Z payload can incorporate a stepper actuated stripper plate capable of removing pipette tips (e.g., the pipette tips described hereinabove). The system can include a pump and manifold system that includes software controlled aspiration, dispensing, and venting of individual fluid volumes within each of the four individual tips and simultaneous dispensing and venting on all tips. The pump and manifold system can have an accuracy and precision of about +/−2 µL per tip for volumes that are less than 20 µL and about +/−10% for volumes greater than or equal to 20 µL (e.g., when aspirating or dispensing in individual tips). The total pump stroke volume can be greater than about 8 µL and less than about 1250 µL. The minimum aspirate and dispense speed can be about 10 µL/sec to about 300 µL/sec. The centroid of the bottom-most face of each pipette tip can be axially aligned with the nozzle centroid of the pipette nozzles within 0.2 mm. The bottom-most pipette tip faces can be co-planar within 0.2 mm. The Z-payload can incorporate a Z axis force sensor capable of feedback to software for applied forces of between about 0 and 4 lbs. The Z-payload can incorporate a downward facing barcode reader capable of reading the system barcodes as described elsewhere herein.

Referring now to racks included in the system, disposable reagent strips (e.g., oriented orthogonally to the front of the instrument) can be contained in 2, 12-lane racks. The 12 reagent strips in a given rack can register and lock into the rack upon insertion by a user. The rack can contain an area for 12 sample lysis tubes and hold the tube bottoms co-planar, allowing the user to orient the bar code to face the rear of the instrument. Certain features, including those listed above, can allow the racks to be inserted and oriented in the instrument by a minimally trained user. Proper rack placement can be confirmed by feedback to the software. In some embodiments, the racks can be black and color fast (e.g, the color may not appreciably degrade with use or washing with a 10% bleach solution) and the rack material can be dimensionally stable within 0.1 mm over the operating temperature range of the system. The rack can be designed with provisions to allow the rack to be carried to and from the instrument and to minimize or eliminate the likelihood that the tubes held by the rack will spill when placed on a flat surface.

Example 10

Exemplary Pipette Tip Usage

Figure 22A:
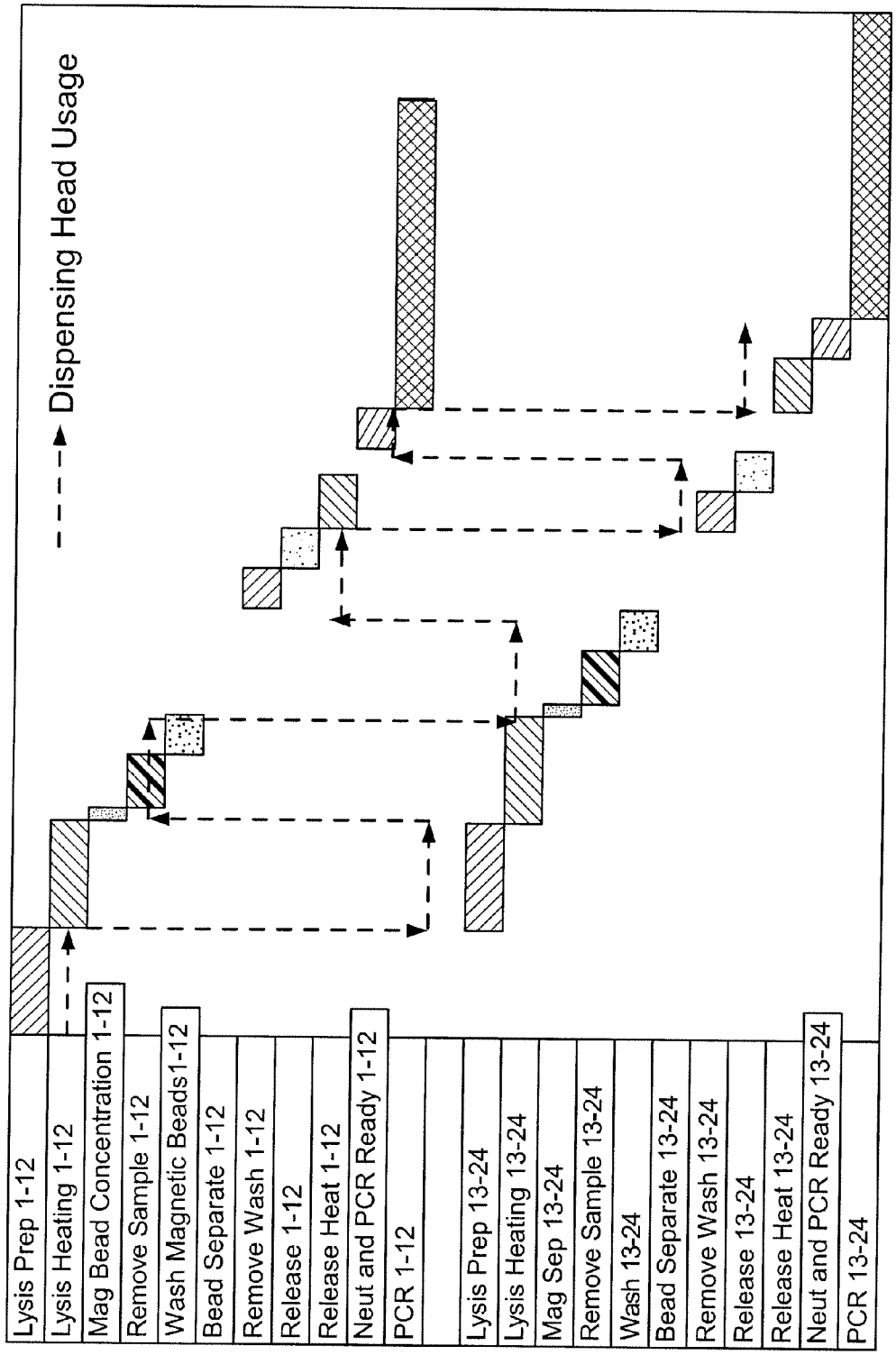
FIGS. 22A-22C show, schematically, pipette head usage during various preparatory processes.
Figure 22B:
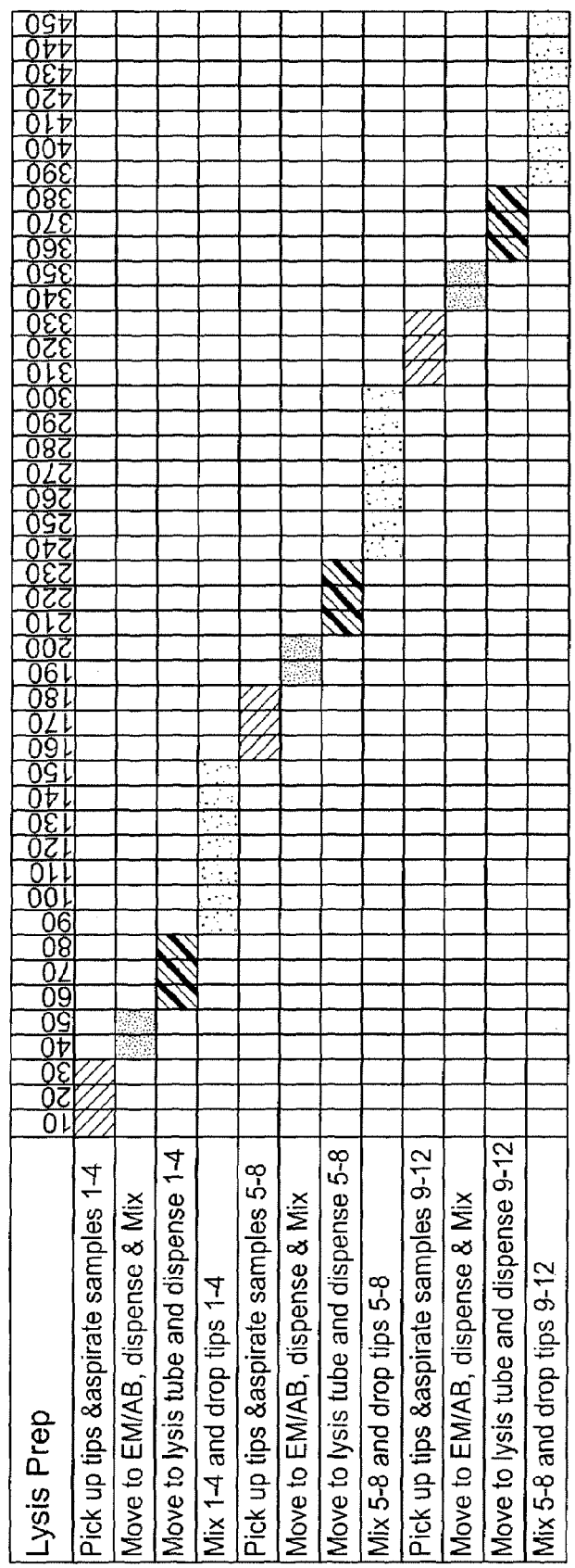
Figure 22C:
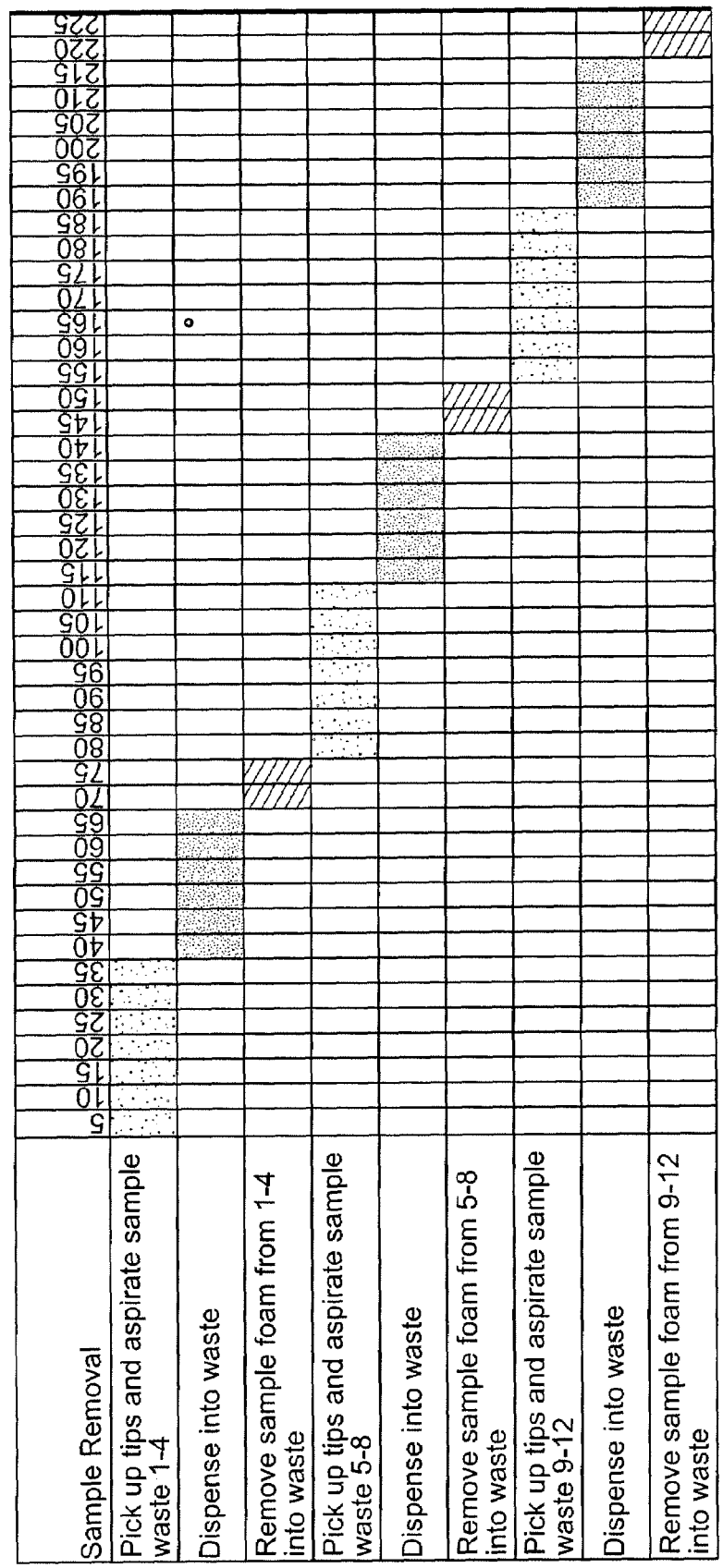

FIGS. 22A-22C show dispense head usage for pipetting operations on banks of 12 samples.

In FIG. 22A, operations on two racks, each containing 12 samples and corresponding reagent holders (labeled 1-12, and 13-24), are shown. The left hand side of the diagram itemizes the set of operations performed. Thus, e.g., "Lysis Prep 1-12" means perform lysis on samples 1-12. In this case, it is the same set of operations on each bank of 12 samples. The dashed line (with arrowheads) shows where liquid dispensing head is. Reading the diagram from left to right shows the order of operations. The dispense head can, e.g., alternate between performing operations on the two racks; the length of a shaded block indicates how long a step takes. In general, the sequence of operations is set up so that, while, e.g., an processing operation such as heating (that does not require the dispense head) is being carried out on one rack, the dispense head can be positioned over the other rack and carry out various liquid transfer operations.

FIG. 22B shows details of how one of the steps in FIG. 22A (Lysis prep.) is carried out on 12 samples, as positioned in a single rack. Numbers at the top of the chart represent time in seconds. The shaded blocks in the grid indicate the location of the dispense head. The operations are applied to the samples in batches of 4. Thus, there are 4 distinct operations to be performed on each sample. In the example shown, a complete sequence of operations on the first batch of 4 is carried out before starting the second batch. It would be understood by one of ordinary skill in the art, that such an approach is exemplary, and that other sequences of steps, or strategy, could be carried out, consistent with the overall goal.

FIG. 22C, laid out similarly to FIG. 22B, shows details of sample removal, expressed in terms of pipette tip aspiration and dispense operations.

The foregoing description is intended to illustrate various aspects of the present inventions. It is not intended that the examples presented herein limit the scope of the present inventions. The technology now being fully described, it will be apparent to one of ordinary skill in the art that many changes and modifications can be made thereto without departing from the spirit or scope of the appended claims.

What is claimed is:

1. A liquid dispenser, comprising:
   a gas manifold comprising a plurality of independently controllable manifold valves and a plurality of lines configured to distribute gas amongst the plurality of manifold valves;
   one or more pumps configured to provide gas to the gas manifold;
   a plurality of dispense heads each in fluid communication with the gas manifold and configured to receive gas from one of said manifold valves; and
   electrical connections configured to transmit control signals from an external controller to the gas manifold for independent operation of each of the plurality of manifold valves,
   wherein each of the plurality of manifold valves is configured to be individually regulated to selectably divert gas from the one or more pumps to one of the plurality of dispense heads.

2. The liquid dispenser of claim 1, having 4 dispense heads, wherein each head is configured to accept a pipette tip.

3. The liquid dispenser of claim 1, configured to aspirate or dispense fluid in connection with analysis or preparation of solutions of two or more samples.

4. The liquid dispenser of claim 1, wherein the liquid dispenser is configured to move in three dimensions through a mechanical connection to a gantry.

5. The liquid dispenser of claim 1, wherein the plurality of dispense heads are individually sprung.

6. The liquid dispenser of claim 1, wherein the manifold comprises at least n+1 manifold valves, wherein n is the number of dispense heads.

7. The liquid dispenser of claim 1, wherein no solution of a sample enters the manifold during normal operation of the dispenser.

8. The liquid dispenser of claim 1, configured to accept or dispense, in a single operation, an amount of 1.0 ml of fluid or less.

9. The liquid dispenser of claim 1, configured to accept or dispense, in a single operation, an amount of fluid in the range 10 nl-1 ml.

10. The liquid dispenser of claim 1, further comprising at least one of an individual pipette tip sensor, an encoder for the pump, a force sensor, a barcode sensor, and an image sensor.

11. The liquid dispenser of claim 4, wherein the mechanical connection to the gantry and the electrical connections are the only external connections to the liquid dispenser.

12. The liquid dispenser of claim 1, wherein the liquid dispenser is configured to dispense liquid into a process tube and a microfluidic cartridge.

13. The liquid dispenser of claim 1, wherein the plurality of manifold valves comprise solenoid valves.

14. The liquid dispenser of claim 1, wherein the manifold further comprises at least one valve configured to vent the one or more pumps.

15. The liquid dispenser of claim 1, further comprising one or more sensors configured to sense when vertical motion of the liquid dispenser is obstructed.

16. The liquid dispenser of claim 1, further comprising a printed circuit board configured to control operation of the manifold.

17. A method of dispensing a liquid using the liquid dispenser of claim 1, the liquid dispenser comprising a manifold comprising a plurality of independently controllable manifold valves, a pump in fluid communication with the manifold, and a plurality of dispense heads in fluid communication with the manifold, each dispense head configured to accept a pipette tip, the method comprising:

transmitting control signals to the gas manifold to independently control each of the plurality of manifold valves;

operating one of the plurality of manifold valves individually to selectably divert gas from the one or more pumps to one of the plurality of dispense heads; and changing a gas pressure in the one of the plurality of dispense heads in order to draw a liquid into or out of a pipette tip attached to the one of the plurality of dispense heads.

18. The method of claim 17, wherein the plurality of manifold valves comprise a plurality of solenoid valves, and wherein transmitting control signals to the gas manifold comprises sending a control signal to one of the plurality of solenoid valves.

19. The method of claim 17, wherein operating one of the plurality of manifold valves comprises opening or closing the one of the plurality of manifold valves to regulate gas flow to a dispense head valve associated with one of the plurality of dispense heads.

20. The method of claim 17, wherein changing a gas pressure in the one of the plurality of dispense heads comprises dispensing solutions of two or more samples into a process tube or a microfluidic cartridge.

* * * * *